US012623080B2

(12) United States Patent
Dumény

(10) Patent No.: US 12,623,080 B2
(45) Date of Patent: May 12, 2026

(54) NEUROMODULATION SYSTEM

(71) Applicant: Onward Medical N.V., Eindhoven (NL)

(72) Inventor: Yoann Dumény, Lausanne (CH)

(73) Assignee: Onward Medical N.V., Eindhoven (NL)

( * ) Notice: Subject to any disclaimer, the term of this patent is extended or adjusted under 35 U.S.C. 154(b) by 353 days.

(21) Appl. No.: 18/339,085

(22) Filed: Jun. 21, 2023

(65) Prior Publication Data

US 2024/0424302 A1     Dec. 26, 2024

(51) Int. Cl.
*A61N 1/36* (2006.01)
*A61N 1/372* (2006.01)

(52) U.S. Cl.
CPC ...... *A61N 1/36146* (2013.01); *A61N 1/37211* (2013.01)

(58) Field of Classification Search
CPC ............ A61N 1/36146; A61N 1/37211; A61N 1/36125; A61N 1/37235; A61N 1/36003;
(Continued)

(56) References Cited

U.S. PATENT DOCUMENTS 2,868,343 A     1/1959   Sproul
3,543,761 A     12/1970  Bradley
(Continued)

FOREIGN PATENT DOCUMENTS

AU     2012204526 B2   5/2016
CA        2649663 A1   11/2007
(Continued)

OTHER PUBLICATIONS

Wessels, M. et al., "Body Weight-Supported Gait Training for Restoration of Walking in People With an Incomplete Spinal Cord Injury: A Systematic Review", Journal of Rehabilitation Medicine, (2010), vol. 42, No. 6, pp. 513-519.
(Continued)

*Primary Examiner* — Brian T Gedeon
(74) *Attorney, Agent, or Firm* — Finnegan, Henderson, Farabow, Garrett & Dunner LLP

(57)     ABSTRACT

Embodiments of the present disclosure may include a neuromodulation system. The neuromodulation system can include an implantable pulse generator configured to provide neuromodulation to a patient based on a sequence of neuromodulation programs. The implantable pulse generator can include alternately accessible memories. The alternately accessible memories can enable the implantable pulse generator to store a second neuromodulation program while providing neuromodulation according to a first neuromodulation program. The IPG can then transition from providing stimulation according to the first neuromodulation program to providing stimulation according to the second neuromodulation program without stopping stimulation. The neuromodulation system can include a parameter memory. Stimulation parameter updates can be written to the parameter memory. The value of the parameter memory can be used to determine the next stimulation pulse. The IPG can accordingly support pulse-to-pulse changes in stimulation parameters.

23 Claims, 5 Drawing Sheets

Pulse Generator 200

(58) Field of Classification Search
CPC . A61N 1/36007; A61N 1/3601; A61N 1/3605
See application file for complete search history.

(56) References Cited

U.S. PATENT DOCUMENTS

| | | | |
|---|---|---|---|
| 3,650,277 | A | 3/1972 | Sjostrand et al. |
| 3,653,518 | A | 4/1972 | Polen |
| 3,662,758 | A | 5/1972 | Glover |
| 3,724,467 | A | 4/1973 | Avery et al. |
| 4,044,774 | A | 8/1977 | Corbin et al. |
| 4,102,344 | A | 7/1978 | Conway et al. |
| 4,141,365 | A | 2/1979 | Fischell et al. |
| 4,285,347 | A | 8/1981 | Hess |
| 4,303,904 | A | 12/1981 | Chasek |
| 4,340,063 | A | 7/1982 | Maurer |
| 4,340,216 | A | 7/1982 | Murphy |
| 4,356,902 | A | 11/1982 | Murphy |
| 4,379,462 | A | 4/1983 | Borkan et al. |
| 4,398,537 | A | 8/1983 | Holmbo |
| 4,402,501 | A | 9/1983 | Lohman |
| 4,410,175 | A | 10/1983 | Shamp |
| 4,414,986 | A | 11/1983 | Dickhudt et al. |
| 4,538,624 | A | 9/1985 | Tarjan |
| 4,549,556 | A | 10/1985 | Tarjan et al. |
| 4,559,948 | A | 12/1985 | Liss et al. |
| 4,569,352 | A | 2/1986 | Petrofsky et al. |
| 4,573,481 | A | 3/1986 | Bullara |
| 4,574,789 | A | 3/1986 | Forster |
| 4,724,842 | A | 2/1988 | Charters |
| 4,742,054 | A | 5/1988 | Naftchi |
| 4,784,420 | A | 11/1988 | Makino et al. |
| 4,798,982 | A | 1/1989 | Voorman |
| 4,800,898 | A | 1/1989 | Hess et al. |
| 4,934,368 | A | 6/1990 | Lynch |
| 4,969,452 | A | 11/1990 | Petrofsky et al. |
| 5,002,053 | A | 3/1991 | Garcia-Rill et al. |
| 5,018,631 | A | 5/1991 | Reimer |
| 5,031,618 | A | 7/1991 | Mullett |
| 5,066,272 | A | 11/1991 | Eaton et al. |
| 5,081,989 | A | 1/1992 | Graupe et al. |
| 5,121,754 | A | 6/1992 | Mullett |
| 5,284,151 | A | 2/1994 | Onoda |
| 5,337,908 | A | 8/1994 | Beck, Jr. |
| 5,344,439 | A | 9/1994 | Otten |
| 5,348,544 | A | 9/1994 | Sweeney et al. |
| 5,354,320 | A | 10/1994 | Schaldach et al. |
| 5,366,813 | A | 11/1994 | Berlin |
| 5,374,285 | A | 12/1994 | Vaiani et al. |
| 5,417,719 | A | 5/1995 | Hull et al. |
| 5,421,783 | A | 6/1995 | Kockelman et al. |
| 5,441,465 | A | 8/1995 | Hefner et al. |
| 5,443,486 | A | 8/1995 | Hrdlicka et al. |
| 5,476,441 | A | 12/1995 | Durfee et al. |
| 5,553,270 | A * | 9/1996 | Rosenbluth ......... G06F 12/0859 |
| | | | 711/E12.051 |
| 5,562,718 | A | 10/1996 | Palermo |
| 5,571,141 | A | 11/1996 | McNeil et al. |
| 5,584,818 | A | 12/1996 | Morrison |
| 5,601,527 | A | 2/1997 | Selkowitz |
| 5,626,540 | A | 5/1997 | Hall |
| 5,630,836 | A | 5/1997 | Prem et al. |
| 5,643,330 | A | 7/1997 | Holsheimer et al. |
| 5,643,332 | A | 7/1997 | Stein |
| 5,667,461 | A | 9/1997 | Hall |
| 5,733,322 | A | 3/1998 | Starkebaum |
| 5,788,606 | A | 8/1998 | Rich |
| 5,814,018 | A | 9/1998 | Elson et al. |
| 5,819,962 | A | 10/1998 | Okubo et al. |
| 5,876,425 | A | 3/1999 | Gord et al. |
| 5,877,183 | A | 3/1999 | Cincotta |
| 5,948,004 | A | 9/1999 | Weijand et al. |
| 5,958,933 | A | 9/1999 | Naftchi |
| 5,983,141 | A | 11/1999 | Sluijter et al. |
| 5,984,368 | A | 11/1999 | Cain |
| 6,052,624 | A | 4/2000 | Mann |
| 6,058,331 | A | 5/2000 | King |
| 6,066,163 | A | 5/2000 | John |
| 6,080,087 | A | 6/2000 | Bingham |
| 6,104,957 | A | 8/2000 | Alo et al. |
| 6,115,634 | A | 9/2000 | Donders et al. |
| 6,122,548 | A | 9/2000 | Starkebaum et al. |
| 6,139,475 | A | 10/2000 | Bessler et al. |
| 6,168,948 | B1 | 1/2001 | Anderson et al. |
| 6,182,843 | B1 | 2/2001 | Tax et al. |
| 6,188,927 | B1 | 2/2001 | Lu et al. |
| 6,236,892 | B1 | 5/2001 | Feler |
| 6,280,640 | B1 | 8/2001 | Hurwitz et al. |
| 6,281,207 | B1 | 8/2001 | Richter et al. |
| 6,308,103 | B1 | 10/2001 | Gielen |
| 6,309,401 | B1 | 10/2001 | Redko et al. |
| 6,319,241 | B1 | 11/2001 | King et al. |
| D454,139 | S | 3/2002 | Feldcamp |
| 6,463,327 | B1 | 10/2002 | Lurie et al. |
| 6,464,208 | B1 | 10/2002 | Smith |
| 6,470,213 | B1 | 10/2002 | Alley |
| 6,490,486 | B1 | 12/2002 | Bradley |
| 6,500,110 | B1 | 12/2002 | Davey et al. |
| 6,503,231 | B1 | 1/2003 | Prausnitz et al. |
| 6,505,074 | B2 | 1/2003 | Boveja et al. |
| 6,516,227 | B1 | 2/2003 | Meadows et al. |
| 6,551,849 | B1 | 4/2003 | Kenney |
| 6,587,724 | B2 | 7/2003 | Mann |
| 6,662,053 | B2 | 12/2003 | Borkan |
| 6,666,831 | B1 | 12/2003 | Edgerton et al. |
| 6,685,729 | B2 | 2/2004 | Gonzalez |
| 6,748,276 | B1 | 6/2004 | Daignault, Jr. et al. |
| 6,819,956 | B2 | 11/2004 | Dilorenzo |
| 6,839,594 | B2 | 1/2005 | Cohen et al. |
| 6,862,479 | B1 | 3/2005 | Whitehurst et al. |
| 6,871,099 | B1 | 3/2005 | Whitehurst et al. |
| 6,878,112 | B2 | 4/2005 | Linberg et al. |
| 6,892,098 | B2 | 5/2005 | Ayal et al. |
| 6,895,280 | B2 | 5/2005 | Meadows et al. |
| 6,895,283 | B2 | 5/2005 | Erickson et al. |
| 6,901,292 | B2 | 5/2005 | Hrdlicka et al. |
| 6,937,891 | B2 | 8/2005 | Leinders et al. |
| 6,950,706 | B2 | 9/2005 | Rodriguez et al. |
| 6,975,907 | B2 | 12/2005 | Zanakis et al. |
| 6,978,181 | B1 | 12/2005 | Snell |
| 6,988,006 | B2 | 1/2006 | King et al. |
| 6,999,820 | B2 | 2/2006 | Jordan |
| 7,010,749 | B2 | 3/2006 | Hasha et al. |
| 7,020,521 | B1 | 3/2006 | Brewer et al. |
| 7,024,247 | B2 | 4/2006 | Gliner et al. |
| 7,035,690 | B2 | 4/2006 | Goetz |
| 7,047,084 | B2 | 5/2006 | Erickson et al. |
| 7,065,408 | B2 | 6/2006 | Herman et al. |
| 7,096,070 | B1 | 8/2006 | Jenkins et al. |
| 7,099,718 | B1 | 8/2006 | Thacker et al. |
| 7,110,820 | B2 | 9/2006 | Tcheng et al. |
| 7,125,388 | B1 | 10/2006 | Reinkensmeyer et al. |
| 7,127,287 | B2 | 10/2006 | Duncan et al. |
| 7,127,296 | B2 | 10/2006 | Bradley |
| 7,127,297 | B2 | 10/2006 | Law et al. |
| 7,135,497 | B1 | 11/2006 | Zeman et al. |
| 7,146,221 | B2 | 12/2006 | Krulevitch et al. |
| 7,149,773 | B2 | 12/2006 | Haller et al. |
| 7,153,242 | B2 | 12/2006 | Goffer |
| 7,184,837 | B2 | 2/2007 | Goetz |
| 7,200,443 | B2 | 4/2007 | Faul |
| 7,209,787 | B2 | 4/2007 | Dilorenzo |
| 7,228,179 | B2 | 6/2007 | Campen et al. |
| 7,239,920 | B1 | 7/2007 | Thacker et al. |
| 7,251,529 | B2 | 7/2007 | Greenwood-Van Meerveld |
| 7,252,090 | B2 | 8/2007 | Goetz |
| 7,313,440 | B2 | 12/2007 | Miesel |
| 7,324,853 | B2 | 1/2008 | Ayal et al. |
| 7,330,760 | B2 | 2/2008 | Heruth et al. |
| 7,330,762 | B2 | 2/2008 | Boveja et al. |
| 7,337,005 | B2 | 2/2008 | Kim et al. |
| 7,337,006 | B2 | 2/2008 | Kim et al. |
| 7,340,298 | B1 | 3/2008 | Barbut |
| 7,377,006 | B2 | 5/2008 | Genoa et al. |
| 7,381,192 | B2 | 6/2008 | Brodard et al. |

(56) References Cited

U.S. PATENT DOCUMENTS

| | | | |
|---|---|---|---|
| 7,415,309 B2 | 8/2008 | McIntyre | |
| 7,450,992 B1 * | 11/2008 | Cameron | A61N 1/0551 |
| | | | 607/46 |
| 7,463,927 B1 | 12/2008 | Chaouat | |
| 7,463,928 B2 | 12/2008 | Lee et al. | |
| 7,467,016 B2 | 12/2008 | Colborn | |
| 7,493,170 B1 | 2/2009 | Segel et al. | |
| 7,496,404 B2 | 2/2009 | Meadows et al. | |
| 7,502,652 B2 | 3/2009 | Gaunt et al. | |
| 7,536,226 B2 | 5/2009 | Williams et al. | |
| D594,024 S | 6/2009 | King | |
| D595,308 S | 6/2009 | King | |
| 7,544,185 B2 | 6/2009 | Bengtsson | |
| 7,565,195 B1 | 7/2009 | Kroll et al. | |
| 7,584,000 B2 | 9/2009 | Erickson | |
| 7,590,454 B2 | 9/2009 | Garabedian et al. | |
| 7,603,178 B2 | 10/2009 | North et al. | |
| 7,620,502 B2 | 11/2009 | Selifonov et al. | |
| 7,628,750 B2 | 12/2009 | Cohen et al. | |
| 7,647,115 B2 | 1/2010 | Levin et al. | |
| 7,660,636 B2 | 2/2010 | Castel et al. | |
| 7,697,995 B2 | 4/2010 | Cross, Jr. et al. | |
| 7,725,193 B1 | 5/2010 | Chu | |
| 7,729,781 B2 | 6/2010 | Swoyer et al. | |
| 7,734,340 B2 | 6/2010 | De Ridder | |
| 7,734,351 B2 | 6/2010 | Testerman et al. | |
| 7,742,037 B2 | 6/2010 | Sako et al. | |
| 7,769,463 B2 | 8/2010 | Katsnelson | |
| 7,769,464 B2 | 8/2010 | Gerber et al. | |
| 7,780,617 B2 | 8/2010 | Tornatore et al. | |
| 7,797,057 B2 | 9/2010 | Harris | |
| 7,801,600 B1 | 9/2010 | Carbunaru et al. | |
| 7,801,601 B2 | 9/2010 | Maschino et al. | |
| 7,813,803 B2 | 10/2010 | Heruth et al. | |
| 7,813,809 B2 | 10/2010 | Strother et al. | |
| 7,840,270 B2 | 11/2010 | Ignagni et al. | |
| 7,856,264 B2 | 12/2010 | Firlik et al. | |
| 7,861,872 B2 | 1/2011 | Ng et al. | |
| 7,877,146 B2 | 1/2011 | Rezai et al. | |
| 7,890,182 B2 | 2/2011 | Parramon et al. | |
| D638,439 S | 5/2011 | Cavanaugh et al. | |
| 7,949,395 B2 | 5/2011 | Kuzma | |
| 7,949,403 B2 | 5/2011 | Palermo et al. | |
| 7,987,000 B2 | 7/2011 | Moffitt et al. | |
| 7,991,465 B2 | 8/2011 | Bartic et al. | |
| 8,019,427 B2 | 9/2011 | Moffitt | |
| 8,050,773 B2 | 11/2011 | Zhu | |
| 8,063,087 B2 | 11/2011 | Chow et al. | |
| 8,100,815 B2 | 1/2012 | Balaker et al. | |
| 8,108,051 B2 | 1/2012 | Cross, Jr. et al. | |
| 8,108,052 B2 | 1/2012 | Boling | |
| D656,153 S | 3/2012 | Imamura et al. | |
| 8,131,358 B2 | 3/2012 | Moffitt et al. | |
| 8,135,473 B2 | 3/2012 | Miesel et al. | |
| 8,155,750 B2 | 4/2012 | Jaax et al. | |
| 8,168,481 B2 | 5/2012 | Hanaoka et al. | |
| 8,170,660 B2 | 5/2012 | Dacey, Jr. et al. | |
| 8,190,262 B2 | 5/2012 | Gerber et al. | |
| 8,195,304 B2 | 6/2012 | Strother et al. | |
| 8,214,048 B1 | 7/2012 | Whitehurst et al. | |
| 8,224,453 B2 | 7/2012 | De Ridder | |
| 8,229,565 B2 | 7/2012 | Kim et al. | |
| 8,238,666 B2 | 8/2012 | Besley et al. | |
| 8,239,038 B2 | 8/2012 | Wolf, II | |
| 8,260,436 B2 | 9/2012 | Gerber et al. | |
| 8,265,770 B2 | 9/2012 | Toy et al. | |
| 8,271,099 B1 | 9/2012 | Swanson | |
| 8,295,936 B2 | 10/2012 | Wahlstrand et al. | |
| 8,311,644 B2 | 11/2012 | Moffitt et al. | |
| 8,326,569 B2 | 12/2012 | Lee et al. | |
| 8,332,029 B2 | 12/2012 | Glukhovsky et al. | |
| 8,332,047 B2 | 12/2012 | Libbus et al. | |
| 8,332,053 B1 | 12/2012 | Patterson et al. | |
| 8,346,366 B2 | 1/2013 | Arle et al. | |
| 8,352,036 B2 | 1/2013 | Dimarco et al. | |
| 8,355,791 B2 | 1/2013 | Moffitt | |
| 8,355,797 B2 | 1/2013 | Caparso et al. | |
| 8,364,273 B2 | 1/2013 | De Ridder | |
| 8,369,961 B2 | 2/2013 | Christman et al. | |
| 8,374,696 B2 | 2/2013 | Sanchez et al. | |
| D677,674 S | 3/2013 | Rampson et al. | |
| 8,407,576 B1 | 3/2013 | Yin et al. | |
| 8,412,345 B2 | 4/2013 | Moffitt | |
| 8,428,728 B2 | 4/2013 | Sachs | |
| 8,442,655 B2 | 5/2013 | Moffitt et al. | |
| 8,452,406 B2 | 5/2013 | Arcot-Krishnamurthy et al. | |
| D684,991 S | 6/2013 | Wenz et al. | |
| D684,996 S | 6/2013 | Wenz et al. | |
| 8,463,400 B2 | 6/2013 | Hegi et al. | |
| D688,259 S | 8/2013 | Pearcy et al. | |
| D689,086 S | 9/2013 | Philopoulos | |
| 8,543,200 B2 | 9/2013 | Lane et al. | |
| D691,154 S | 10/2013 | Talbot et al. | |
| D691,172 S | 10/2013 | Wujcik et al. | |
| 8,588,884 B2 | 11/2013 | Hegde et al. | |
| D694,763 S | 12/2013 | Edwards et al. | |
| 8,626,300 B2 | 1/2014 | Demarais et al. | |
| 8,630,717 B2 | 1/2014 | Olson et al. | |
| 8,700,145 B2 | 4/2014 | Kilgard et al. | |
| 8,712,546 B2 | 4/2014 | Kim et al. | |
| D705,241 S | 5/2014 | Chen et al. | |
| D707,235 S | 6/2014 | Arnold et al. | |
| 8,740,825 B2 | 6/2014 | Ehrenreich et al. | |
| 8,750,957 B2 | 6/2014 | Tang et al. | |
| RE45,030 E | 7/2014 | Stevenson et al. | |
| 8,766,928 B2 | 7/2014 | Weeldreyer et al. | |
| 8,768,472 B2 | 7/2014 | Fang et al. | |
| 8,768,481 B2 | 7/2014 | Lane | |
| 8,805,542 B2 | 8/2014 | Tai et al. | |
| 8,836,368 B2 | 9/2014 | Afshar et al. | |
| 8,847,548 B2 | 9/2014 | Kesler et al. | |
| 8,849,410 B2 | 9/2014 | Walker et al. | |
| 8,849,418 B2 | 9/2014 | Daglow | |
| 8,897,870 B2 | 11/2014 | De Ridder | |
| 8,903,502 B2 | 12/2014 | Perryman et al. | |
| D721,722 S | 1/2015 | Lee | |
| 8,957,549 B2 | 2/2015 | Kesler et al. | |
| D735,231 S | 7/2015 | Omiya | |
| 9,072,891 B1 | 7/2015 | Rao | |
| 9,079,039 B2 | 7/2015 | Carlson et al. | |
| 9,101,769 B2 | 8/2015 | Edgerton et al. | |
| D737,840 S | 9/2015 | Omiya | |
| 9,192,768 B2 | 11/2015 | Yokoi et al. | |
| 9,205,259 B2 | 12/2015 | Kim et al. | |
| 9,205,260 B2 | 12/2015 | Kim et al. | |
| 9,205,261 B2 | 12/2015 | Kim et al. | |
| 9,248,291 B2 | 2/2016 | Mashiach | |
| D750,664 S | 3/2016 | Chen et al. | |
| 9,272,139 B2 | 3/2016 | Hamilton et al. | |
| 9,272,143 B2 | 3/2016 | Libbus et al. | |
| 9,283,391 B2 | 3/2016 | Ahmed | |
| 9,314,630 B2 | 4/2016 | Levin et al. | |
| D758,398 S | 6/2016 | Yu et al. | |
| 9,358,384 B2 | 6/2016 | Dubuclet | |
| D760,753 S | 7/2016 | Cheng et al. | |
| D762,234 S | 7/2016 | Li et al. | |
| 9,393,409 B2 | 7/2016 | Edgerton et al. | |
| D763,273 S | 8/2016 | Hwang et al. | |
| 9,409,023 B2 | 8/2016 | Burdick et al. | |
| 9,409,030 B2 | 8/2016 | Perryman et al. | |
| 9,415,218 B2 | 8/2016 | Edgerton et al. | |
| 9,421,365 B2 | 8/2016 | Sumners et al. | |
| D769,302 S | 10/2016 | Rodriguez | |
| D770,468 S | 11/2016 | Carlson et al. | |
| D770,470 S | 11/2016 | Jin | |
| 9,520,887 B1 | 12/2016 | Zhuang et al. | |
| D780,768 S | 3/2017 | Carlson et al. | |
| 9,592,358 B2 | 3/2017 | Miller et al. | |
| 9,592,385 B2 | 3/2017 | Kaula et al. | |
| 9,597,517 B2 | 3/2017 | Moffitt | |
| D783,032 S | 4/2017 | Cashner et al. | |
| 9,610,442 B2 | 4/2017 | Yoo et al. | |
| D788,134 S | 5/2017 | Wong et al. | |
| 9,639,982 B2 | 5/2017 | Craik et al. | |

(56) References Cited

U.S. PATENT DOCUMENTS

| | | |
|---|---|---|
| 9,656,076 B2 | 5/2017 | Trier et al. |
| D789,963 S | 6/2017 | Agashiwala et al. |
| D794,667 S | 8/2017 | Havaldar et al. |
| 9,717,908 B2 | 8/2017 | Karunasiri |
| 9,724,513 B2 | 8/2017 | Lane et al. |
| 9,802,052 B2 | 10/2017 | Marnfeldt |
| 9,812,875 B2 | 11/2017 | Nejatali et al. |
| D806,717 S | 1/2018 | Bae et al. |
| 9,895,545 B2 | 2/2018 | Rao et al. |
| D816,708 S | 5/2018 | Riedel et al. |
| D819,681 S | 6/2018 | Fung et al. |
| 9,993,642 B2 | 6/2018 | Gerasimenko et al. |
| 10,092,750 B2 | 10/2018 | Edgerton et al. |
| D834,601 S | 11/2018 | Felt |
| 10,124,166 B2 | 11/2018 | Edgerton et al. |
| 10,137,299 B2 | 11/2018 | Lu et al. |
| D839,278 S | 1/2019 | Carlson et al. |
| D839,914 S | 2/2019 | Lee et al. |
| D841,017 S | 2/2019 | Bathla |
| D843,388 S | 3/2019 | Protzman et al. |
| 10,406,366 B2 | 9/2019 | Westlund et al. |
| 10,449,371 B2 | 10/2019 | Serrano Carmona |
| D874,491 S | 2/2020 | Kuo et al. |
| D874,507 S | 2/2020 | Martell et al. |
| D875,108 S | 2/2020 | Chitalia et al. |
| D875,752 S | 2/2020 | Nelson et al. |
| D877,753 S | 3/2020 | Chitalia et al. |
| 10,751,533 B2 | 8/2020 | Edgerton et al. |
| 10,758,732 B1 | 9/2020 | Heldman |
| 10,773,074 B2 | 9/2020 | Liu et al. |
| 10,799,701 B2 | 10/2020 | Lee |
| 10,806,927 B2 | 10/2020 | Edgerton et al. |
| 10,806,935 B2 | 10/2020 | Rao et al. |
| D904,437 S | 12/2020 | Chitalia et al. |
| D905,701 S | 12/2020 | Feng et al. |
| 10,881,853 B2 | 1/2021 | Edgerton et al. |
| 10,898,719 B2 | 1/2021 | Pivonka et al. |
| D912,074 S | 3/2021 | Giannino et al. |
| D926,784 S | 8/2021 | Carlson et al. |
| D928,188 S | 8/2021 | Giannino et al. |
| 11,097,122 B2 | 8/2021 | Lu |
| 11,123,312 B2 | 9/2021 | Lu et al. |
| 11,129,983 B2 | 9/2021 | Lo et al. |
| D939,549 S | 12/2021 | Miyai et al. |
| D947,216 S | 3/2022 | Leininger |
| 11,266,850 B2 | 3/2022 | Prouza et al. |
| 11,298,533 B2 | 4/2022 | Edgerton et al. |
| D962,245 S | 8/2022 | Thompson et al. |
| 11,400,284 B2 | 8/2022 | Gerasimenko et al. |
| 11,491,336 B2 | 11/2022 | Scheltienne et al. |
| 11,511,116 B2 | 11/2022 | Wagner et al. |
| 11,515,733 B2 | 11/2022 | Babakhani et al. |
| 11,638,820 B2 | 5/2023 | Edgerton et al. |
| 11,691,015 B2 | 7/2023 | Minassian et al. |
| D1,008,290 S | 12/2023 | Stapfer |
| D1,008,291 S | 12/2023 | Stapfer |
| D1,010,666 S | 1/2024 | Cai et al. |
| 11,911,621 B2 | 2/2024 | Ganty et al. |
| 11,944,814 B2 | 4/2024 | Lo et al. |
| 11,957,910 B2 | 4/2024 | Edgerton et al. |
| 11,986,653 B2 | 5/2024 | Lo et al. |
| 11,992,684 B2 | 5/2024 | Minassian et al. |
| 12,018,135 B2 | 6/2024 | Scher et al. |
| 12,023,492 B2 | 7/2024 | Edgerton et al. |
| 12,076,301 B2 | 9/2024 | Lu et al. |
| D1,044,827 S | 10/2024 | Tabrizi et al. |
| 12,201,833 B2 | 1/2025 | Edgerton et al. |
| 12,268,878 B2 | 4/2025 | Phillips et al. |
| 12,415,079 B2 | 9/2025 | Scheltienne et al. |
| 2001/0016266 A1 | 8/2001 | Okazaki et al. |
| 2001/0032992 A1 | 10/2001 | Wendt |
| 2002/0042814 A1 | 4/2002 | Fukasawa et al. |
| 2002/0050456 A1 | 5/2002 | Sheppard, Jr. et al. |
| 2002/0052539 A1 | 5/2002 | Haller et al. |
| 2002/0055779 A1 | 5/2002 | Andrews |
| 2002/0083240 A1 | 6/2002 | Hoese et al. |
| 2002/0111661 A1 | 8/2002 | Cross et al. |
| 2002/0115945 A1 | 8/2002 | Herman et al. |
| 2002/0123672 A1 | 9/2002 | Christophersom et al. |
| 2002/0138512 A1 | 9/2002 | Buresh et al. |
| 2002/0173505 A1 | 11/2002 | Skogvall |
| 2002/0175931 A1 | 11/2002 | Holtz et al. |
| 2002/0187260 A1 | 12/2002 | Sheppard, Jr. et al. |
| 2002/0188332 A1 | 12/2002 | Lurie et al. |
| 2002/0193843 A1 | 12/2002 | Hill et al. |
| 2003/0032992 A1 | 2/2003 | Thacker et al. |
| 2003/0078633 A1 | 4/2003 | Firlik et al. |
| 2003/0093021 A1 | 5/2003 | Goffer |
| 2003/0093131 A1 | 5/2003 | Loeb et al. |
| 2003/0097166 A1 | 5/2003 | Krulevitch et al. |
| 2003/0100933 A1 | 5/2003 | Ayal et al. |
| 2003/0113725 A1 | 6/2003 | Small et al. |
| 2003/0114894 A1 | 6/2003 | Dar et al. |
| 2003/0114899 A1 | 6/2003 | Woods et al. |
| 2003/0135253 A1 | 7/2003 | Kokones et al. |
| 2003/0139422 A1 | 7/2003 | Teng |
| 2003/0145759 A1 | 8/2003 | Rodnunsky |
| 2003/0158583 A1 | 8/2003 | Burnett et al. |
| 2003/0199116 A1 | 10/2003 | Tai et al. |
| 2003/0200323 A1 | 10/2003 | Dold et al. |
| 2003/0208248 A1 | 11/2003 | Carter et al. |
| 2003/0220679 A1 | 11/2003 | Han |
| 2003/0233137 A1 | 12/2003 | Paul, Jr. |
| 2004/0039425 A1 | 2/2004 | Greenwood-Van Meerveld |
| 2004/0044380 A1 | 3/2004 | Bruninga et al. |
| 2004/0082979 A1 | 4/2004 | Tong et al. |
| 2004/0087286 A1 | 5/2004 | Inoue et al. |
| 2004/0088015 A1 | 5/2004 | Casavant et al. |
| 2004/0111118 A1 | 6/2004 | Hill et al. |
| 2004/0111126 A1 | 6/2004 | Tanagho et al. |
| 2004/0121528 A1 | 6/2004 | Krulevitch et al. |
| 2004/0122483 A1 | 6/2004 | Nathan et al. |
| 2004/0127954 A1 | 7/2004 | McDonald |
| 2004/0133248 A1 | 7/2004 | Frei et al. |
| 2004/0138518 A1 | 7/2004 | Rise et al. |
| 2004/0172027 A1 | 9/2004 | Speitling et al. |
| 2004/0172097 A1 | 9/2004 | Brodard et al. |
| 2004/0181263 A1 | 9/2004 | Balzer et al. |
| 2004/0192082 A1 | 9/2004 | Wagner et al. |
| 2004/0192834 A1 | 9/2004 | Nakayoshi et al. |
| 2004/0243204 A1 | 12/2004 | Maghribi et al. |
| 2004/0267320 A1 | 12/2004 | Taylor et al. |
| 2005/0004622 A1 | 1/2005 | Cullen et al. |
| 2005/0043775 A1 | 2/2005 | John et al. |
| 2005/0061315 A1 | 3/2005 | Lee et al. |
| 2005/0070982 A1 | 3/2005 | Heruth et al. |
| 2005/0075662 A1 | 4/2005 | Pedersen et al. |
| 2005/0075669 A1 | 4/2005 | King |
| 2005/0075678 A1 | 4/2005 | Faul |
| 2005/0075693 A1 | 4/2005 | Toy et al. |
| 2005/0080460 A1 | 4/2005 | Wang et al. |
| 2005/0090756 A1 | 4/2005 | Wolf et al. |
| 2005/0101827 A1 | 5/2005 | Delisle |
| 2005/0102007 A1 | 5/2005 | Ayal et al. |
| 2005/0113878 A1 | 5/2005 | Gerber |
| 2005/0113882 A1 | 5/2005 | Cameron et al. |
| 2005/0119713 A1 | 6/2005 | Whitehurst et al. |
| 2005/0125045 A1 | 6/2005 | Brighton et al. |
| 2005/0203588 A1 | 9/2005 | King |
| 2005/0205961 A1 | 9/2005 | Doong |
| 2005/0209655 A1 | 9/2005 | Bradley et al. |
| 2005/0231186 A1 | 10/2005 | Saavedra Barrera et al. |
| 2005/0239612 A1 | 10/2005 | Keiser |
| 2005/0246004 A1 | 11/2005 | Cameron et al. |
| 2005/0253273 A1 | 11/2005 | Tai et al. |
| 2005/0277999 A1 | 12/2005 | Strother et al. |
| 2005/0278000 A1 | 12/2005 | Strother et al. |
| 2006/0003090 A1 | 1/2006 | Rodger et al. |
| 2006/0007983 A1 | 1/2006 | Tai et al. |
| 2006/0015153 A1 | 1/2006 | Gliner et al. |
| 2006/0015470 A1 | 1/2006 | Lauer et al. |
| 2006/0016266 A1 | 1/2006 | Weise et al. |
| 2006/0018360 A1 | 1/2006 | Tai et al. |
| 2006/0041225 A1 | 2/2006 | Wallace et al. |

(56) References Cited

U.S. PATENT DOCUMENTS

| | | |
|---|---|---|
| 2006/0041295 A1 | 2/2006 | Osypka |
| 2006/0047325 A1 | 3/2006 | Thimineur et al. |
| 2006/0075339 A1 | 4/2006 | Tomita et al. |
| 2006/0082626 A1 | 4/2006 | Oikawa et al. |
| 2006/0089696 A1 | 4/2006 | Olsen et al. |
| 2006/0095088 A1 | 5/2006 | De Ridder |
| 2006/0100671 A1 | 5/2006 | Ridder |
| 2006/0111754 A1 | 5/2006 | Rezai et al. |
| 2006/0122678 A1 | 6/2006 | Olsen et al. |
| 2006/0142337 A1 | 6/2006 | Ikeura et al. |
| 2006/0142816 A1 | 6/2006 | Fruitman et al. |
| 2006/0142822 A1 | 6/2006 | Tulgar |
| 2006/0149333 A1 | 7/2006 | Tanagho et al. |
| 2006/0149337 A1 | 7/2006 | John |
| 2006/0189453 A1 | 8/2006 | Leblond |
| 2006/0189839 A1 | 8/2006 | Laniado et al. |
| 2006/0195153 A1 | 8/2006 | Diubaldi et al. |
| 2006/0239482 A1 | 10/2006 | Hatoum |
| 2006/0241356 A1 | 10/2006 | Flaherty |
| 2006/0282127 A1 | 12/2006 | Zealear |
| 2007/0004567 A1 | 1/2007 | Shetty et al. |
| 2007/0009968 A1 | 1/2007 | Cunningham et al. |
| 2007/0016097 A1 | 1/2007 | Farquhar et al. |
| 2007/0016266 A1 | 1/2007 | Paul |
| 2007/0016268 A1 | 1/2007 | Carter et al. |
| 2007/0016329 A1 | 1/2007 | Herr et al. |
| 2007/0021513 A1 | 1/2007 | Agee et al. |
| 2007/0027495 A1 | 2/2007 | Gerber |
| 2007/0047852 A1 | 3/2007 | Sharp et al. |
| 2007/0049814 A1 | 3/2007 | Muccio |
| 2007/0055318 A1 | 3/2007 | Forsberg et al. |
| 2007/0055337 A1 | 3/2007 | Tanrisever |
| 2007/0060954 A1 | 3/2007 | Cameron et al. |
| 2007/0060980 A1 | 3/2007 | Strother et al. |
| 2007/0067003 A1 | 3/2007 | Sanchez et al. |
| 2007/0073357 A1 | 3/2007 | Rooney et al. |
| 2007/0083240 A1 | 4/2007 | Peterson et al. |
| 2007/0100389 A1 | 5/2007 | Jaax et al. |
| 2007/0121702 A1 | 5/2007 | Laguardia et al. |
| 2007/0121709 A1 | 5/2007 | Ittogi |
| 2007/0129769 A1 | 6/2007 | Bourget et al. |
| 2007/0142874 A1 | 6/2007 | John |
| 2007/0142878 A1 | 6/2007 | Krulevitch et al. |
| 2007/0150023 A1 | 6/2007 | Ignagni et al. |
| 2007/0150034 A1 | 6/2007 | Rooney et al. |
| 2007/0156172 A1 | 7/2007 | Alvarado |
| 2007/0156179 A1 | 7/2007 | S.E. |
| 2007/0156200 A1 | 7/2007 | Kornet et al. |
| 2007/0168008 A1 | 7/2007 | Olsen |
| 2007/0179534 A1 | 8/2007 | Firlik et al. |
| 2007/0179579 A1 | 8/2007 | Feler et al. |
| 2007/0191709 A1 | 8/2007 | Swanson |
| 2007/0208381 A1 | 9/2007 | Hill et al. |
| 2007/0233204 A1 | 10/2007 | Lima et al. |
| 2007/0250119 A1 | 10/2007 | Tyler et al. |
| 2007/0255372 A1 | 11/2007 | Metzler et al. |
| 2007/0265621 A1 | 11/2007 | Matthis et al. |
| 2007/0265679 A1 | 11/2007 | Bradley et al. |
| 2007/0265691 A1 | 11/2007 | Swanson |
| 2007/0276449 A1 | 11/2007 | Gunter et al. |
| 2007/0276450 A1 | 11/2007 | Meadows et al. |
| 2007/0282378 A1 | 12/2007 | Huang et al. |
| 2007/0293910 A1 | 12/2007 | Strother et al. |
| 2008/0002227 A1 | 1/2008 | Tsujimoto |
| 2008/0004674 A1 | 1/2008 | King et al. |
| 2008/0009927 A1 | 1/2008 | Vilims |
| 2008/0021513 A1 | 1/2008 | Thacker et al. |
| 2008/0027346 A1 | 1/2008 | Litt et al. |
| 2008/0046049 A1 | 2/2008 | Skubitz et al. |
| 2008/0051851 A1 | 2/2008 | Lin |
| 2008/0071325 A1 | 3/2008 | Bradley |
| 2008/0077192 A1 | 3/2008 | Harry et al. |
| 2008/0092911 A1 | 4/2008 | Schulman et al. |
| 2008/0103579 A1 | 5/2008 | Gerber |
| 2008/0105185 A1 | 5/2008 | Kuhlman |
| 2008/0127031 A1 | 5/2008 | Olsson et al. |
| 2008/0140152 A1 | 6/2008 | Imran et al. |
| 2008/0140162 A1 | 6/2008 | Goetz et al. |
| 2008/0140169 A1 | 6/2008 | Imran |
| 2008/0147143 A1 | 6/2008 | Popovic et al. |
| 2008/0154329 A1 | 6/2008 | Pyles et al. |
| 2008/0183097 A1 | 7/2008 | Leyde et al. |
| 2008/0183224 A1 | 7/2008 | Barolat |
| 2008/0200749 A1 | 8/2008 | Zheng et al. |
| 2008/0202940 A1 | 8/2008 | Jiang et al. |
| 2008/0207985 A1 | 8/2008 | Farone |
| 2008/0208287 A1 | 8/2008 | Palermo et al. |
| 2008/0215113 A1 | 9/2008 | Pawlowicz |
| 2008/0221653 A1 | 9/2008 | Agrawal et al. |
| 2008/0224226 A1 | 9/2008 | Suzuki et al. |
| 2008/0228241 A1 | 9/2008 | Sachs |
| 2008/0228250 A1 | 9/2008 | Mironer |
| 2008/0234121 A1 | 9/2008 | Kim et al. |
| 2008/0234791 A1 | 9/2008 | Arle et al. |
| 2008/0255582 A1 | 10/2008 | Harris |
| 2008/0269854 A1 | 10/2008 | Hegland et al. |
| 2008/0275129 A1 | 11/2008 | Lundstedt et al. |
| 2008/0279896 A1 | 11/2008 | Heinen et al. |
| 2008/0287268 A1 | 11/2008 | Hidler |
| 2008/0294211 A1 | 11/2008 | Moffitt |
| 2008/0294226 A1 | 11/2008 | Moffitt et al. |
| 2008/0318733 A1 | 12/2008 | Osler-Weppenaar |
| 2009/0005844 A1 | 1/2009 | Swoyer et al. |
| 2009/0012436 A1 | 1/2009 | Lanfermann et al. |
| 2009/0024186 A1 | 1/2009 | Brockway |
| 2009/0024997 A1 | 1/2009 | Kobayashi |
| 2009/0093854 A1 | 4/2009 | Leung et al. |
| 2009/0112281 A1 | 4/2009 | Miyazawa et al. |
| 2009/0118365 A1 | 5/2009 | Benson, III et al. |
| 2009/0131995 A1 | 5/2009 | Sloan et al. |
| 2009/0157141 A1 | 6/2009 | Chiao et al. |
| 2009/0198305 A1 | 8/2009 | Naroditsky et al. |
| 2009/0204173 A1 | 8/2009 | Fang et al. |
| 2009/0227925 A1 | 9/2009 | Mcbean et al. |
| 2009/0229166 A1 | 9/2009 | Sawrie |
| 2009/0254151 A1 | 10/2009 | Anderson et al. |
| 2009/0270960 A1 | 10/2009 | Zhao et al. |
| 2009/0281529 A1 | 11/2009 | Carriazo |
| 2009/0281599 A1 | 11/2009 | Thacker et al. |
| 2009/0293270 A1 | 12/2009 | Brindley et al. |
| 2009/0299166 A1 | 12/2009 | Nishida et al. |
| 2009/0299167 A1 | 12/2009 | Seymour |
| 2009/0306491 A1 | 12/2009 | Haggers |
| 2009/0312165 A1 | 12/2009 | Rempe |
| 2010/0004715 A1 | 1/2010 | Fahey |
| 2010/0006737 A1 | 1/2010 | Colombo et al. |
| 2010/0008782 A1 | 1/2010 | Danescu et al. |
| 2010/0010646 A1 | 1/2010 | Drew et al. |
| 2010/0016732 A1 | 1/2010 | Wells et al. |
| 2010/0023069 A1 | 1/2010 | Moffitt et al. |
| 2010/0023070 A1 | 1/2010 | Moffitt et al. |
| 2010/0023103 A1 | 1/2010 | Elborno |
| 2010/0029040 A1 | 2/2010 | Nomoto |
| 2010/0042193 A1 | 2/2010 | Slavin |
| 2010/0048358 A1 | 2/2010 | Tchao et al. |
| 2010/0057177 A1 | 3/2010 | Moffitt et al. |
| 2010/0063568 A1 | 3/2010 | Staunton et al. |
| 2010/0070007 A1 | 3/2010 | Parker et al. |
| 2010/0070010 A1 | 3/2010 | Simpson |
| 2010/0087782 A1 | 4/2010 | Ghaffari et al. |
| 2010/0094800 A1 | 4/2010 | Sharp |
| 2010/0114205 A1 | 5/2010 | Donofrio et al. |
| 2010/0114239 A1 | 5/2010 | Mcdonald, III |
| 2010/0116526 A1 | 5/2010 | Arora et al. |
| 2010/0125313 A1 | 5/2010 | Lee et al. |
| 2010/0137238 A1 | 6/2010 | Gan et al. |
| 2010/0137938 A1 | 6/2010 | Kishawi et al. |
| 2010/0137943 A1 | 6/2010 | Zhu |
| 2010/0145428 A1 | 6/2010 | Cameron et al. |
| 2010/0152811 A1 | 6/2010 | Flaherty |
| 2010/0166546 A1 | 7/2010 | Mahan et al. |
| 2010/0168820 A1 | 7/2010 | Maniak et al. |
| 2010/0179562 A1 | 7/2010 | Linker et al. |
| 2010/0185253 A1 | 7/2010 | Dimarco et al. |

(56)         References Cited

U.S. PATENT DOCUMENTS

| | | |
|---|---|---|
| 2010/0191307 A1 | 7/2010 | Fang et al. |
| 2010/0198298 A1 | 8/2010 | Glukhovsky et al. |
| 2010/0217355 A1 | 8/2010 | Tass et al. |
| 2010/0217418 A1 | 8/2010 | Fontanot |
| 2010/0228310 A1 | 9/2010 | Shuros et al. |
| 2010/0241121 A1 | 9/2010 | Logan et al. |
| 2010/0241191 A1 | 9/2010 | Testerman et al. |
| 2010/0268299 A1 | 10/2010 | Farone |
| 2010/0274312 A1 | 10/2010 | Alataris et al. |
| 2010/0279606 A1 | 11/2010 | Hillan et al. |
| 2010/0280570 A1 | 11/2010 | Sturm et al. |
| 2010/0298905 A1 | 11/2010 | Simon |
| 2010/0298910 A1 | 11/2010 | Carbunaru et al. |
| 2010/0305660 A1 | 12/2010 | Hegi et al. |
| 2010/0312304 A1 | 12/2010 | York et al. |
| 2010/0318168 A1 | 12/2010 | Bighetti |
| 2010/0324699 A1 | 12/2010 | Herr et al. |
| 2010/0331925 A1 | 12/2010 | Peterson |
| 2011/0006793 A1 | 1/2011 | Peschke et al. |
| 2011/0009919 A1 | 1/2011 | Carbunaru et al. |
| 2011/0016081 A1 | 1/2011 | Basak et al. |
| 2011/0029040 A1 | 2/2011 | Walker et al. |
| 2011/0029044 A1 | 2/2011 | Hyde et al. |
| 2011/0034277 A1 | 2/2011 | Brandes |
| 2011/0034912 A1 | 2/2011 | De Graff et al. |
| 2011/0034977 A1 | 2/2011 | Janik et al. |
| 2011/0040349 A1 | 2/2011 | Graupe |
| 2011/0054567 A1 | 3/2011 | Lane et al. |
| 2011/0054568 A1 | 3/2011 | Lane et al. |
| 2011/0054570 A1 | 3/2011 | Lane |
| 2011/0054579 A1 | 3/2011 | Kumar et al. |
| 2011/0060461 A1 | 3/2011 | Velliste et al. |
| 2011/0077660 A1 | 3/2011 | Janik et al. |
| 2011/0082515 A1 | 4/2011 | Libbus et al. |
| 2011/0084489 A1 | 4/2011 | Kaplan |
| 2011/0093043 A1 | 4/2011 | Torgerson et al. |
| 2011/0112601 A1 | 5/2011 | Meadows et al. |
| 2011/0112611 A1 | 5/2011 | Aghassian |
| 2011/0118815 A1 | 5/2011 | Kuzma et al. |
| 2011/0125203 A1 | 5/2011 | Simon et al. |
| 2011/0130804 A1 | 6/2011 | Lin et al. |
| 2011/0152967 A1 | 6/2011 | Simon et al. |
| 2011/0160810 A1 | 6/2011 | Griffith |
| 2011/0166546 A1 | 7/2011 | Jaax et al. |
| 2011/0184482 A1 | 7/2011 | Eberman et al. |
| 2011/0184488 A1 | 7/2011 | De Ridder |
| 2011/0184489 A1 | 7/2011 | Nicolelis et al. |
| 2011/0201944 A1 | 8/2011 | Higgins et al. |
| 2011/0202107 A1 | 8/2011 | Sunagawa et al. |
| 2011/0208265 A1 | 8/2011 | Erickson et al. |
| 2011/0213266 A1 | 9/2011 | Williams et al. |
| 2011/0218590 A1 | 9/2011 | Degiorgio et al. |
| 2011/0218594 A1 | 9/2011 | Doron et al. |
| 2011/0224153 A1 | 9/2011 | Levitt et al. |
| 2011/0224665 A1 | 9/2011 | Crosby et al. |
| 2011/0224752 A1 | 9/2011 | Rolston et al. |
| 2011/0224753 A1 | 9/2011 | Palermo et al. |
| 2011/0224755 A1 | 9/2011 | Arie et al. |
| 2011/0224757 A1 | 9/2011 | Zdeblick et al. |
| 2011/0230101 A1 | 9/2011 | Tang et al. |
| 2011/0230701 A1 | 9/2011 | Simon et al. |
| 2011/0230702 A1 | 9/2011 | Honour |
| 2011/0230747 A1 | 9/2011 | Rogers et al. |
| 2011/0230808 A1 | 9/2011 | Lisowski |
| 2011/0231326 A1 | 9/2011 | Marino |
| 2011/0237221 A1 | 9/2011 | Prakash et al. |
| 2011/0237921 A1 | 9/2011 | Askin et al. |
| 2011/0245734 A1 | 10/2011 | Wagner et al. |
| 2011/0260126 A1 | 10/2011 | Willis |
| 2011/0270360 A1 | 11/2011 | Harris et al. |
| 2011/0276107 A1 | 11/2011 | Simon et al. |
| 2011/0288609 A1 | 11/2011 | Tehrani et al. |
| 2011/0295100 A1 | 12/2011 | Hegde et al. |
| 2012/0006793 A1 | 1/2012 | Swanson |
| 2012/0011222 A1 | 1/2012 | Yasukawa et al. |
| 2012/0011950 A1 | 1/2012 | Kracke |
| 2012/0013041 A1 | 1/2012 | Cao et al. |
| 2012/0013126 A1 | 1/2012 | Molloy |
| 2012/0016448 A1 | 1/2012 | Lee |
| 2012/0016453 A1 | 1/2012 | Feler et al. |
| 2012/0018249 A1 | 1/2012 | Mehr |
| 2012/0022371 A1 | 1/2012 | Summerton |
| 2012/0022551 A1 | 1/2012 | Staunton et al. |
| 2012/0029528 A1 | 2/2012 | Macdonald et al. |
| 2012/0035684 A1 | 2/2012 | Thompson et al. |
| 2012/0036552 A1 | 2/2012 | Dare et al. |
| 2012/0041518 A1 | 2/2012 | Kim et al. |
| 2012/0052432 A1 | 3/2012 | Matsuura |
| 2012/0053645 A1 | 3/2012 | Ayanoor-Vitikkate et al. |
| 2012/0059432 A1 | 3/2012 | Emborg et al. |
| 2012/0071250 A1 | 3/2012 | O'Neil et al. |
| 2012/0071950 A1 | 3/2012 | Archer |
| 2012/0083709 A1 | 4/2012 | Parker et al. |
| 2012/0101326 A1 | 4/2012 | Simon et al. |
| 2012/0109251 A1 | 5/2012 | Lebedev et al. |
| 2012/0109295 A1 | 5/2012 | Fan |
| 2012/0116476 A1 | 5/2012 | Kothandaraman |
| 2012/0116478 A1 | 5/2012 | Buhlmann et al. |
| 2012/0123223 A1 | 5/2012 | Freeman et al. |
| 2012/0123293 A1 | 5/2012 | Shah et al. |
| 2012/0126392 A1 | 5/2012 | Kalvesten et al. |
| 2012/0136408 A1 | 5/2012 | Grill et al. |
| 2012/0143281 A1 | 6/2012 | Birkill et al. |
| 2012/0161531 A1 | 6/2012 | Kim |
| 2012/0161721 A1 | 6/2012 | Neethimanickam |
| 2012/0165899 A1 | 6/2012 | Gliner |
| 2012/0168397 A1 | 7/2012 | Lim et al. |
| 2012/0172222 A1 | 7/2012 | Artigas Puerto |
| 2012/0172246 A1 | 7/2012 | Nguyen et al. |
| 2012/0172510 A1 | 7/2012 | Esseghir et al. |
| 2012/0172946 A1 | 7/2012 | Alataris et al. |
| 2012/0179222 A1 | 7/2012 | Jaax et al. |
| 2012/0185020 A1 | 7/2012 | Simon et al. |
| 2012/0197338 A1 | 8/2012 | Su et al. |
| 2012/0203055 A1 | 8/2012 | Pletnev |
| 2012/0203131 A1 | 8/2012 | Dilorenzo |
| 2012/0203246 A1 | 8/2012 | Staunton et al. |
| 2012/0221073 A1 | 8/2012 | Southwell et al. |
| 2012/0232615 A1 | 9/2012 | Barolat et al. |
| 2012/0252380 A1 | 10/2012 | Kawakita |
| 2012/0252874 A1 | 10/2012 | Feinstein et al. |
| 2012/0259380 A1 | 10/2012 | Pyles |
| 2012/0265269 A1 | 10/2012 | Lui |
| 2012/0271315 A1 | 10/2012 | Pianca et al. |
| 2012/0271372 A1 | 10/2012 | Osorio |
| 2012/0277824 A1 | 11/2012 | Li |
| 2012/0277834 A1 | 11/2012 | Mercanzini et al. |
| 2012/0283697 A1 | 11/2012 | Kim et al. |
| 2012/0283797 A1 | 11/2012 | De Ridder |
| 2012/0302821 A1 | 11/2012 | Burnett |
| 2012/0310305 A1 | 12/2012 | Kaula et al. |
| 2012/0310315 A1 | 12/2012 | Savage et al. |
| 2012/0330321 A1 | 12/2012 | Johnson et al. |
| 2012/0330391 A1 | 12/2012 | Bradley et al. |
| 2013/0006322 A1 | 1/2013 | Tai |
| 2013/0006793 A1 | 1/2013 | O'Sullivan et al. |
| 2013/0012853 A1 | 1/2013 | Brown |
| 2013/0013041 A1 | 1/2013 | Glukhovsky et al. |
| 2013/0023972 A1 | 1/2013 | Kuzma et al. |
| 2013/0026640 A1 | 1/2013 | Ito et al. |
| 2013/0030312 A1 | 1/2013 | Keel et al. |
| 2013/0030319 A1 | 1/2013 | Hettrick et al. |
| 2013/0030501 A1 | 1/2013 | Feler et al. |
| 2013/0032508 A1 | 2/2013 | Azuma |
| 2013/0035745 A1 | 2/2013 | Ahmed et al. |
| 2013/0041235 A1 | 2/2013 | Rogers et al. |
| 2013/0053734 A1 | 2/2013 | Barriskill et al. |
| 2013/0053922 A1 | 2/2013 | Ahmed et al. |
| 2013/0066392 A1 | 3/2013 | Simon et al. |
| 2013/0066411 A1 | 3/2013 | Thacker et al. |
| 2013/0085317 A1 | 4/2013 | Feinstein |
| 2013/0085361 A1 | 4/2013 | Mercanzini et al. |
| 2013/0096640 A1 | 4/2013 | Passover |
| 2013/0096661 A1 | 4/2013 | Greenberg et al. |

(56)  References Cited

U.S. PATENT DOCUMENTS

| | | |
|---|---|---|
| 2013/0096662 A1 | 4/2013 | Swanson |
| 2013/0110196 A1 | 5/2013 | Alataris et al. |
| 2013/0116604 A1 | 5/2013 | Marilla et al. |
| 2013/0116751 A1 | 5/2013 | Moffitt et al. |
| 2013/0123568 A1 | 5/2013 | Hamilton et al. |
| 2013/0123659 A1 | 5/2013 | Bartol et al. |
| 2013/0138167 A1 | 5/2013 | Bradley et al. |
| 2013/0150915 A1 | 6/2013 | Kane et al. |
| 2013/0154373 A1 | 6/2013 | Lisuwandi et al. |
| 2013/0158444 A1 | 6/2013 | Herr et al. |
| 2013/0165991 A1 | 6/2013 | Kim et al. |
| 2013/0190143 A1 | 7/2013 | Greenhill et al. |
| 2013/0197408 A1 | 8/2013 | Goldfarb et al. |
| 2013/0204324 A1 | 8/2013 | Thacker et al. |
| 2013/0211477 A1 | 8/2013 | Cullen et al. |
| 2013/0226263 A1 | 8/2013 | Kelly et al. |
| 2013/0237948 A1 | 9/2013 | Donders et al. |
| 2013/0245712 A1 | 9/2013 | Simon et al. |
| 2013/0253222 A1 | 9/2013 | Nakao |
| 2013/0253229 A1 | 9/2013 | Sawant et al. |
| 2013/0253299 A1 | 9/2013 | Weber et al. |
| 2013/0253611 A1 | 9/2013 | Lee et al. |
| 2013/0268016 A1 | 10/2013 | Xi et al. |
| 2013/0268020 A1 | 10/2013 | Rosenberg et al. |
| 2013/0268021 A1 | 10/2013 | Moffitt |
| 2013/0268041 A1 | 10/2013 | Schulte et al. |
| 2013/0281890 A1 | 10/2013 | Mishelevich |
| 2013/0289446 A1 | 10/2013 | Stone et al. |
| 2013/0289650 A1 | 10/2013 | Karlsson et al. |
| 2013/0289664 A1 | 10/2013 | Johanek |
| 2013/0289667 A1 | 10/2013 | Wacnik et al. |
| 2013/0296965 A1 | 11/2013 | Mokelke et al. |
| 2013/0303873 A1 | 11/2013 | Voros et al. |
| 2013/0304159 A1 | 11/2013 | Simon et al. |
| 2013/0310211 A1 | 11/2013 | Wilton et al. |
| 2013/0310911 A1 | 11/2013 | Tai et al. |
| 2013/0325081 A1 | 12/2013 | Karst et al. |
| 2013/0325083 A1 | 12/2013 | Bharmi et al. |
| 2013/0345780 A1 | 12/2013 | Tabada et al. |
| 2014/0005753 A1 | 1/2014 | Carbunaru |
| 2014/0031893 A1 | 1/2014 | Walker et al. |
| 2014/0031895 A1 | 1/2014 | Rahimi et al. |
| 2014/0046407 A1 | 2/2014 | Ben-Ezra et al. |
| 2014/0053401 A1 | 2/2014 | Kuzma et al. |
| 2014/0058292 A1 | 2/2014 | Alford et al. |
| 2014/0058490 A1 | 2/2014 | Dimarco |
| 2014/0059499 A1 | 2/2014 | Kim et al. |
| 2014/0066950 A1 | 3/2014 | Macdonald et al. |
| 2014/0067007 A1 | 3/2014 | Drees et al. |
| 2014/0067013 A1 | 3/2014 | Kaula et al. |
| 2014/0067354 A1 | 3/2014 | Kaula et al. |
| 2014/0074190 A1 | 3/2014 | Griffith |
| 2014/0081011 A1 | 3/2014 | Vaught et al. |
| 2014/0081071 A1 | 3/2014 | Simon et al. |
| 2014/0081345 A1 | 3/2014 | Hershey |
| 2014/0087922 A1 | 3/2014 | Bayerlein et al. |
| 2014/0088674 A1 | 3/2014 | Bradley |
| 2014/0100491 A1 | 4/2014 | Hu et al. |
| 2014/0100633 A1 | 4/2014 | Mann et al. |
| 2014/0107397 A1 | 4/2014 | Simon et al. |
| 2014/0107398 A1 | 4/2014 | Simon et al. |
| 2014/0114374 A1 | 4/2014 | Rooney et al. |
| 2014/0114385 A1 | 4/2014 | Nijhuis et al. |
| 2014/0124713 A1 | 5/2014 | Majumdar et al. |
| 2014/0142652 A1 | 5/2014 | Francois et al. |
| 2014/0163640 A1 | 6/2014 | Edgerton et al. |
| 2014/0171961 A1 | 6/2014 | Lacey et al. |
| 2014/0172045 A1 | 6/2014 | Yip et al. |
| 2014/0172055 A1 | 6/2014 | Venancio |
| 2014/0180361 A1 | 6/2014 | Burdick et al. |
| 2014/0201905 A1 | 7/2014 | Glukhovsky |
| 2014/0213842 A1 | 7/2014 | Simon et al. |
| 2014/0213844 A1 | 7/2014 | Pilla et al. |
| 2014/0228905 A1 | 8/2014 | Bolea |
| 2014/0236257 A1 | 8/2014 | Parker et al. |
| 2014/0243923 A1 | 8/2014 | Doan et al. |
| 2014/0277271 A1 | 9/2014 | Chan et al. |
| 2014/0296752 A1 | 10/2014 | Edgerton et al. |
| 2014/0303685 A1 | 10/2014 | Rosenberg et al. |
| 2014/0303901 A1 | 10/2014 | Sadeh |
| 2014/0316484 A1 | 10/2014 | Edgerton et al. |
| 2014/0316503 A1 | 10/2014 | Tai et al. |
| 2014/0324118 A1 | 10/2014 | Simon et al. |
| 2014/0330067 A1 | 11/2014 | Jordan |
| 2014/0330335 A1 | 11/2014 | Errico et al. |
| 2014/0336722 A1 | 11/2014 | Rocon De Lima et al. |
| 2014/0339909 A1 | 11/2014 | Sugawara |
| 2014/0343623 A1 | 11/2014 | Alves et al. |
| 2014/0344740 A1 | 11/2014 | Kaula et al. |
| 2014/0357936 A1 | 12/2014 | Simon et al. |
| 2014/0359521 A1 | 12/2014 | Lin et al. |
| 2014/0371830 A1 | 12/2014 | Howard et al. |
| 2015/0005167 A1 | 1/2015 | Jung et al. |
| 2015/0005840 A1 | 1/2015 | Pal et al. |
| 2015/0012061 A1 | 1/2015 | Chen |
| 2015/0022143 A1 | 1/2015 | Kim |
| 2015/0032187 A1 | 1/2015 | Ranu et al. |
| 2015/0051674 A1 | 2/2015 | Barner et al. |
| 2015/0057717 A1 | 2/2015 | Wu et al. |
| 2015/0065559 A1 | 3/2015 | Feinstein et al. |
| 2015/0066111 A1 | 3/2015 | Blum et al. |
| 2015/0074997 A1 | 3/2015 | Kuzma et al. |
| 2015/0088212 A1 | 3/2015 | De Ridder |
| 2015/0094734 A1 | 4/2015 | Staunton et al. |
| 2015/0094791 A1 | 4/2015 | Edgell et al. |
| 2015/0120634 A1 | 4/2015 | Tateno |
| 2015/0126120 A1 | 5/2015 | Chen |
| 2015/0148878 A1 | 5/2015 | Yoo et al. |
| 2015/0151114 A1 | 6/2015 | Black et al. |
| 2015/0151126 A1 | 6/2015 | Kishawi et al. |
| 2015/0165226 A1 | 6/2015 | Simon et al. |
| 2015/0174411 A1 | 6/2015 | Ranu |
| 2015/0182784 A1 | 7/2015 | Barriskill et al. |
| 2015/0188592 A1 | 7/2015 | Solondz |
| 2015/0190200 A1 | 7/2015 | Courtine et al. |
| 2015/0190634 A1 | 7/2015 | Rezai et al. |
| 2015/0196231 A1 | 7/2015 | Ziaie et al. |
| 2015/0196241 A1 | 7/2015 | Yekutieli |
| 2015/0200561 A1 | 7/2015 | Lee et al. |
| 2015/0217120 A1 | 8/2015 | Nandra et al. |
| 2015/0224326 A1 | 8/2015 | Toth et al. |
| 2015/0231326 A1 | 8/2015 | Milner et al. |
| 2015/0231396 A1 | 8/2015 | Burdick et al. |
| 2015/0246216 A1 | 9/2015 | Barker |
| 2015/0265830 A1 | 9/2015 | Simon et al. |
| 2015/0268845 A1 | 9/2015 | Endo |
| 2015/0320632 A1 | 11/2015 | Vallery et al. |
| 2015/0328462 A1 | 11/2015 | Griffith |
| 2015/0343199 A1 | 12/2015 | Wechter et al. |
| 2015/0343205 A1 | 12/2015 | Howard et al. |
| 2016/0001096 A1 | 1/2016 | Mishelevich |
| 2016/0005538 A1 | 1/2016 | Koyanagi et al. |
| 2016/0030737 A1 | 2/2016 | Gerasimenko et al. |
| 2016/0030748 A1 | 2/2016 | Edgerton et al. |
| 2016/0030750 A1 | 2/2016 | Bokil et al. |
| 2016/0045727 A1 | 2/2016 | Rezai et al. |
| 2016/0045731 A1 | 2/2016 | Simon et al. |
| 2016/0067477 A1 | 3/2016 | Dubuclet |
| 2016/0074663 A1 | 3/2016 | De Ridder |
| 2016/0082261 A1 | 3/2016 | Moffitt et al. |
| 2016/0121109 A1 | 5/2016 | Edgerton et al. |
| 2016/0121114 A1 | 5/2016 | Simon et al. |
| 2016/0121116 A1 | 5/2016 | Simon et al. |
| 2016/0121121 A1 | 5/2016 | Mashiach |
| 2016/0136477 A1 | 5/2016 | Bucher et al. |
| 2016/0143588 A1 | 5/2016 | Hoitink et al. |
| 2016/0144167 A1 | 5/2016 | Bakker et al. |
| 2016/0144184 A1 | 5/2016 | Marnfeldt |
| 2016/0157389 A1 | 6/2016 | Hwang |
| 2016/0166828 A1 | 6/2016 | Yu |
| 2016/0175586 A1 | 6/2016 | Edgerton et al. |
| 2016/0197488 A1 | 7/2016 | Hada et al. |
| 2016/0213918 A1 | 7/2016 | Howard et al. |
| 2016/0220813 A1 | 8/2016 | Edgerton et al. |

(56)  References Cited

U.S. PATENT DOCUMENTS

| | | |
|---|---|---|
| 2016/0228706 A1 | 8/2016 | Hershey et al. |
| 2016/0235977 A1 | 8/2016 | Lu et al. |
| 2016/0250461 A1 | 9/2016 | Dubuclet |
| 2016/0263376 A1 | 9/2016 | Yoo et al. |
| 2016/0271413 A1 | 9/2016 | Vallejo et al. |
| 2016/0279418 A1 | 9/2016 | Courtine et al. |
| 2016/0279429 A1 | 9/2016 | Hershey et al. |
| 2016/0291848 A1 | 10/2016 | Hall et al. |
| 2016/0310739 A1 | 10/2016 | Burdick et al. |
| 2016/0339239 A1 | 11/2016 | Yoo et al. |
| 2016/0367827 A1 | 12/2016 | Tahmasian |
| 2017/0007320 A1 | 1/2017 | Levin et al. |
| 2017/0007831 A1 | 1/2017 | Edgerton et al. |
| 2017/0014620 A9 | 1/2017 | Staunton et al. |
| 2017/0014622 A1 | 1/2017 | Bozung et al. |
| 2017/0065814 A1 | 3/2017 | Howard et al. |
| 2017/0079598 A1 | 3/2017 | Stolen et al. |
| 2017/0098951 A1 | 4/2017 | Olgun et al. |
| 2017/0098962 A1 | 4/2017 | Desrosiers |
| 2017/0118722 A1 | 4/2017 | Hong et al. |
| 2017/0128729 A1 | 5/2017 | Netoff et al. |
| 2017/0156662 A1 | 6/2017 | Goodall et al. |
| 2017/0157389 A1 | 6/2017 | Tai et al. |
| 2017/0157396 A1 | 6/2017 | Dixon et al. |
| 2017/0161454 A1 | 6/2017 | Grill et al. |
| 2017/0165497 A1 | 6/2017 | Lu |
| 2017/0173326 A1 | 6/2017 | Bloch et al. |
| 2017/0189686 A1 | 7/2017 | Steinke et al. |
| 2017/0239486 A1 | 8/2017 | Suryavanshi |
| 2017/0246450 A1 | 8/2017 | Liu et al. |
| 2017/0246452 A1 | 8/2017 | Liu et al. |
| 2017/0266455 A1 | 9/2017 | Steinke |
| 2017/0274209 A1 | 9/2017 | Edgerton et al. |
| 2017/0291023 A1 | 10/2017 | Kuzma et al. |
| 2017/0296837 A1 | 10/2017 | Jin |
| 2017/0338570 A1 | 11/2017 | Myers |
| 2017/0348523 A1 | 12/2017 | Rubehn et al. |
| 2017/0348532 A1 | 12/2017 | Moffitt et al. |
| 2017/0354819 A1 | 12/2017 | Bloch et al. |
| 2017/0361093 A1 | 12/2017 | Yoo et al. |
| 2017/0361115 A1 | 12/2017 | Aghassian et al. |
| 2018/0008826 A1 | 1/2018 | Dimarco |
| 2018/0028812 A1 | 2/2018 | Vallejo et al. |
| 2018/0056078 A1 | 3/2018 | Kashyap et al. |
| 2018/0083473 A1 | 3/2018 | Menegoli et al. |
| 2018/0085582 A1 | 3/2018 | Calle et al. |
| 2018/0085583 A1 | 3/2018 | Zhang et al. |
| 2018/0093093 A1 | 4/2018 | Courtine et al. |
| 2018/0104479 A1 | 4/2018 | Grill et al. |
| 2018/0110992 A1 | 4/2018 | Parramon et al. |
| 2018/0117334 A1 | 5/2018 | Jung |
| 2018/0125416 A1 | 5/2018 | Schwarz et al. |
| 2018/0125419 A1 | 5/2018 | Yun et al. |
| 2018/0126154 A1 | 5/2018 | Dubuclet |
| 2018/0126155 A1 | 5/2018 | Mclaughlin et al. |
| 2018/0133480 A1 | 5/2018 | Annoni et al. |
| 2018/0133481 A1 | 5/2018 | Von Zitzewitz et al. |
| 2018/0153474 A1 | 6/2018 | Aeschlimann et al. |
| 2018/0178008 A1 | 6/2018 | Bouton et al. |
| 2018/0185632 A1 | 7/2018 | Staunton et al. |
| 2018/0185642 A1 | 7/2018 | Lu |
| 2018/0185648 A1 | 7/2018 | Nandra et al. |
| 2018/0193655 A1 | 7/2018 | Zhang et al. |
| 2018/0214694 A1 | 8/2018 | Parramon |
| 2018/0221620 A1 | 8/2018 | Metzger |
| 2018/0221651 A1 | 8/2018 | Chang et al. |
| 2018/0228421 A1 | 8/2018 | Saab |
| 2018/0229037 A1 | 8/2018 | Edgerton et al. |
| 2018/0229038 A1 | 8/2018 | Burdick et al. |
| 2018/0236240 A1 | 8/2018 | Harkema et al. |
| 2018/0256906 A1 | 9/2018 | Pivonka et al. |
| 2018/0272125 A1 | 9/2018 | Sandhu |
| 2018/0272132 A1 | 9/2018 | Subbaroyan et al. |
| 2018/0280693 A1 | 10/2018 | Edgerton et al. |
| 2018/0280706 A1 | 10/2018 | Maile et al. |
| 2018/0289971 A1 | 10/2018 | Yeh et al. |
| 2018/0294547 A1 | 10/2018 | Park et al. |
| 2018/0318576 A1 | 11/2018 | Bozung et al. |
| 2018/0326220 A1* | 11/2018 | Kaula ............... A61N 1/37235 |
| 2018/0337547 A1 | 11/2018 | Menegoli et al. |
| 2018/0353755 A1 | 12/2018 | Edgerton et al. |
| 2018/0361146 A1 | 12/2018 | Gerasimenko et al. |
| 2018/0367187 A1 | 12/2018 | Mcfarthing |
| 2018/0369574 A1 | 12/2018 | Dubuclet et al. |
| 2018/0369575 A1 | 12/2018 | Dubuclet et al. |
| 2018/0369576 A1 | 12/2018 | Dubuclet et al. |
| 2019/0001122 A1 | 1/2019 | Ganty et al. |
| 2019/0001139 A1 | 1/2019 | Mishra et al. |
| 2019/0009094 A1 | 1/2019 | Zhang et al. |
| 2019/0017983 A1 | 1/2019 | Smith |
| 2019/0022371 A1 | 1/2019 | Chang et al. |
| 2019/0027257 A1 | 1/2019 | Ghogawala |
| 2019/0033622 A1 | 1/2019 | Olgun et al. |
| 2019/0160294 A1 | 5/2019 | Peterson et al. |
| 2019/0167980 A1 | 6/2019 | Peterson |
| 2019/0167987 A1 | 6/2019 | Lu et al. |
| 2019/0192852 A1 | 6/2019 | De Ridder |
| 2019/0192864 A1 | 6/2019 | Koop et al. |
| 2019/0240468 A1 | 8/2019 | Yun et al. |
| 2019/0247650 A1 | 8/2019 | Tran |
| 2019/0262609 A1 | 8/2019 | Brill et al. |
| 2019/0269917 A1 | 9/2019 | Courtine et al. |
| 2019/0299006 A1 | 10/2019 | Marnfeldt |
| 2019/0321639 A1 | 10/2019 | Rao et al. |
| 2019/0336760 A1 | 11/2019 | Shah |
| 2019/0344070 A1 | 11/2019 | Molnar et al. |
| 2019/0344075 A1 | 11/2019 | Bloch et al. |
| 2019/0358454 A1 | 11/2019 | Lin et al. |
| 2019/0374776 A1 | 12/2019 | Mishra et al. |
| 2019/0374777 A1 | 12/2019 | Burdick et al. |
| 2019/0381313 A1 | 12/2019 | Lu |
| 2019/0381328 A1 | 12/2019 | Wechter et al. |
| 2019/0381382 A1 | 12/2019 | Wu |
| 2020/0009385 A1 | 1/2020 | Shah |
| 2020/0060602 A1 | 2/2020 | Wagner et al. |
| 2020/0061378 A1 | 2/2020 | Ganguly et al. |
| 2020/0086116 A1 | 3/2020 | Formento et al. |
| 2020/0121544 A1 | 4/2020 | George et al. |
| 2020/0139126 A1 | 5/2020 | Napadow et al. |
| 2020/0144846 A1 | 5/2020 | Shin |
| 2020/0147382 A1 | 5/2020 | Caban et al. |
| 2020/0155019 A1 | 5/2020 | Esteller et al. |
| 2020/0155865 A1 | 5/2020 | Lu |
| 2020/0228901 A1 | 7/2020 | Baek |
| 2020/0360697 A1 | 11/2020 | Paoles et al. |
| 2020/0398068 A1 | 12/2020 | Agnihotri et al. |
| 2021/0069052 A1 | 3/2021 | Burke |
| 2021/0093865 A1 | 4/2021 | Vallejo et al. |
| 2021/0121692 A1 | 4/2021 | Edgerton et al. |
| 2021/0153942 A1 | 5/2021 | Scheltienne et al. |
| 2021/0154481 A1 | 5/2021 | Scheltienne et al. |
| 2021/0170177 A1 | 6/2021 | Minassian et al. |
| 2021/0170178 A1 | 6/2021 | Wagner et al. |
| 2021/0187278 A1 | 6/2021 | Lu |
| 2021/0213292 A1 | 7/2021 | Minassian et al. |
| 2021/0236837 A1 | 8/2021 | Lu |
| 2021/0275810 A1 | 9/2021 | Caban |
| 2021/0290955 A1 | 9/2021 | Brouns et al. |
| 2021/0299441 A1 | 9/2021 | Edgerton et al. |
| 2021/0378991 A1 | 12/2021 | Lu |
| 2021/0402186 A1 | 12/2021 | Edgerton et al. |
| 2022/0016420 A1 | 1/2022 | Lo et al. |
| 2022/0111208 A1 | 4/2022 | Phillips et al. |
| 2022/0125374 A1 | 4/2022 | Courtine et al. |
| 2022/0134108 A1 | 5/2022 | Dinsmoor et al. |
| 2022/0143407 A1 | 5/2022 | Zhuang et al. |
| 2022/0161042 A1 | 5/2022 | Lu et al. |
| 2022/0176130 A1 | 6/2022 | Wu et al. |
| 2022/0184386 A1 | 6/2022 | Courtine et al. |
| 2022/0233848 A1 | 7/2022 | Gad et al. |
| 2022/0313993 A1 | 10/2022 | Gerasimenko et al. |
| 2022/0409899 A1 | 12/2022 | Ganty et al. |
| 2023/0045403 A1 | 2/2023 | Robison et al. |
| 2023/0053053 A1 | 2/2023 | Delattre et al. |

(56)             References Cited

U.S. PATENT DOCUMENTS

| | | |
|---|---|---|
| 2023/0186201 A1 | 6/2023 | Cella et al. |
| 2023/0281527 A1 | 9/2023 | Cella et al. |
| 2024/0001116 A1 | 1/2024 | Edgerton et al. |
| 2024/0050746 A1 | 2/2024 | Angeli et al. |
| 2024/0335666 A1 | 10/2024 | Murphy |
| 2024/0374541 A1 | 11/2024 | Lu et al. |
| 2024/0424291 A1 | 12/2024 | Ganty et al. |
| 2024/0424302 A1 | 12/2024 | Dumeny |
| 2025/0025689 A1 | 1/2025 | Lo et al. |
| 2025/0032799 A1 | 1/2025 | Weijand et al. |

FOREIGN PATENT DOCUMENTS

| | | |
|---|---|---|
| CA | 2823592 A1 | 7/2012 |
| CA | 2856202 A1 | 5/2013 |
| CA | 2864473 A1 | 5/2013 |
| CA | 3034123 A1 | 2/2018 |
| CN | 101227940 A | 7/2008 |
| CN | 101822223 A | 9/2010 |
| CN | 103263727 A | 8/2013 |
| CN | 104307098 A | 1/2015 |
| DE | 3830429 A1 | 3/1990 |
| DE | 202007015508 U1 | 3/2008 |
| EP | 0034145 A1 | 8/1981 |
| EP | 0236976 A1 | 9/1987 |
| EP | 0630987 A1 | 12/1994 |
| EP | 1127907 A2 | 8/2001 |
| EP | 1303332 A1 | 4/2003 |
| EP | 1575665 A1 | 9/2005 |
| EP | 1675648 A1 | 7/2006 |
| EP | 1680182 A1 | 7/2006 |
| EP | 2130326 A1 | 12/2009 |
| EP | 2141851 A2 | 1/2010 |
| EP | 2160127 A1 | 3/2010 |
| EP | 2178319 A1 | 4/2010 |
| EP | 2192897 A1 | 6/2010 |
| EP | 2226114 A1 | 9/2010 |
| EP | 2243510 A2 | 10/2010 |
| EP | 2258496 A1 | 12/2010 |
| EP | 2361631 A1 | 8/2011 |
| EP | 2368401 A1 | 9/2011 |
| EP | 2387467 A1 | 11/2011 |
| EP | 2396995 A1 | 12/2011 |
| EP | 2397788 A1 | 12/2011 |
| EP | 2445990 A2 | 5/2012 |
| EP | 2471518 A2 | 7/2012 |
| EP | 2475283 A1 | 7/2012 |
| EP | 2486897 A2 | 8/2012 |
| EP | 2626051 A1 | 8/2013 |
| EP | 2628502 A1 | 8/2013 |
| EP | 2661307 A2 | 11/2013 |
| EP | 2665514 A2 | 11/2013 |
| EP | 2688642 A2 | 1/2014 |
| EP | 2810689 A1 | 12/2014 |
| EP | 2810690 A1 | 12/2014 |
| EP | 2868323 A1 | 5/2015 |
| EP | 2868343 A1 | 5/2015 |
| EP | 2966422 A1 | 1/2016 |
| EP | 2968940 A1 | 1/2016 |
| EP | 3184145 A1 | 6/2017 |
| EP | 3269424 A1 | 1/2018 |
| EP | 3323468 A1 | 5/2018 |
| EP | 3328481 A1 | 6/2018 |
| EP | 3381506 A1 | 10/2018 |
| EP | 3421081 A1 | 1/2019 |
| EP | 3285855 B1 | 6/2019 |
| EP | 3495019 A1 | 6/2019 |
| EP | 3527258 A1 | 8/2019 |
| EP | 3969100 B1 | 7/2023 |
| JP | H0326620 A | 2/1991 |
| JP | 3184145 B2 | 7/2001 |
| JP | 2002517283 A | 6/2002 |
| JP | 2002200178 A | 7/2002 |
| JP | 2004065529 A | 3/2004 |
| JP | 2007526798 A | 9/2007 |
| JP | 2008067917 A | 3/2008 |
| JP | 2008543429 A | 12/2008 |
| JP | 2009512516 A | 3/2009 |
| JP | 2011502586 A | 1/2011 |
| JP | 2011504112 A | 2/2011 |
| JP | 2012515060 A | 7/2012 |
| JP | 2013508119 A | 3/2013 |
| JP | 2014513562 A | 6/2014 |
| JP | 2014514043 A | 6/2014 |
| JP | 2016506255 A | 3/2016 |
| JP | 6132856 B2 | 5/2017 |
| JP | 2017104685 A | 6/2017 |
| JP | 2017523868 A | 8/2017 |
| JP | 2017525509 A | 9/2017 |
| JP | 2018524113 A | 8/2018 |
| KR | 101573840 B1 | 12/2015 |
| RU | 2130326 C1 | 5/1999 |
| RU | 2141851 C1 | 11/1999 |
| RU | 2160127 C1 | 12/2000 |
| RU | 2178319 C2 | 1/2002 |
| RU | 2192897 C2 | 11/2002 |
| RU | 2193441 C2 | 11/2002 |
| RU | 2001102533 A | 11/2002 |
| RU | 2226114 C1 | 3/2004 |
| RU | 2258496 C2 | 8/2005 |
| RU | 2361631 C2 | 7/2009 |
| RU | 2368401 C1 | 9/2009 |
| RU | 2387467 C1 | 4/2010 |
| RU | 2396995 C2 | 8/2010 |
| RU | 2397788 C2 | 8/2010 |
| RU | 2445990 C1 | 3/2012 |
| RU | 2471518 C2 | 1/2013 |
| RU | 2475283 C2 | 2/2013 |
| RU | 2661307 C1 | 7/2018 |
| WO | 8100458 A1 | 2/1981 |
| WO | 9409808 A1 | 5/1994 |
| WO | 9747357 A1 | 12/1997 |
| WO | 9908749 A1 | 2/1999 |
| WO | 0019912 A1 | 4/2000 |
| WO | 0209808 A1 | 2/2002 |
| WO | 0234331 A2 | 5/2002 |
| WO | 02092165 A1 | 11/2002 |
| WO | 03005887 A2 | 1/2003 |
| WO | 03026735 A2 | 4/2003 |
| WO | 03092795 A1 | 11/2003 |
| WO | 2003094749 A1 | 11/2003 |
| WO | 2004087116 A2 | 10/2004 |
| WO | 2005002663 A2 | 1/2005 |
| WO | 2005051306 A2 | 6/2005 |
| WO | 2005065768 A1 | 7/2005 |
| WO | 2005087307 A2 | 9/2005 |
| WO | 2006026850 A1 | 3/2006 |
| WO | 2006135751 A2 | 12/2006 |
| WO | 2006138069 A1 | 12/2006 |
| WO | 2007007057 A1 | 1/2007 |
| WO | 2007007058 A1 | 1/2007 |
| WO | 2007012114 A1 | 2/2007 |
| WO | 2007047852 A2 | 4/2007 |
| WO | 2007057508 A2 | 5/2007 |
| WO | 2007081764 A2 | 7/2007 |
| WO | 2007107831 A2 | 9/2007 |
| WO | 2008075294 A1 | 6/2008 |
| WO | 2008092785 A1 | 8/2008 |
| WO | 2008070807 A3 | 9/2008 |
| WO | 2008109862 A2 | 9/2008 |
| WO | 2008121891 A1 | 10/2008 |
| WO | 2009042217 A1 | 4/2009 |
| WO | 2009111142 A2 | 9/2009 |
| WO | 2010021977 A1 | 2/2010 |
| WO | 2010055421 A1 | 5/2010 |
| WO | 2010083308 A1 | 7/2010 |
| WO | 2010114998 A1 | 10/2010 |
| WO | 2010124128 A1 | 10/2010 |
| WO | 2011005607 A1 | 1/2011 |
| WO | 2011008459 A2 | 1/2011 |
| WO | 2011136875 A1 | 11/2011 |
| WO | 2012050200 A1 | 4/2012 |
| WO | 2012075195 A1 | 6/2012 |
| WO | 2012080964 A1 | 6/2012 |

(56) References Cited

FOREIGN PATENT DOCUMENTS

| | | | |
|---|---|---|---|
| WO | 2012094346 | A2 | 7/2012 |
| WO | 2012100260 | A2 | 7/2012 |
| WO | 2012103519 | A2 | 8/2012 |
| WO | 2012129574 | A2 | 9/2012 |
| WO | 2013049658 | A1 | 4/2013 |
| WO | 2013069004 | A1 | 5/2013 |
| WO | 2013071307 | A1 | 5/2013 |
| WO | 2013071309 | A1 | 5/2013 |
| WO | 2013117750 | A1 | 8/2013 |
| WO | 2013152124 | A1 | 10/2013 |
| WO | 2013179230 | A1 | 12/2013 |
| WO | 2013188965 | A1 | 12/2013 |
| WO | 2014005075 | A1 | 1/2014 |
| WO | 2014031142 | A1 | 2/2014 |
| WO | 2014089299 | A2 | 6/2014 |
| WO | 2014144785 | A1 | 9/2014 |
| WO | 2014149895 | A1 | 9/2014 |
| WO | 2014205356 | A2 | 12/2014 |
| WO | 2014209877 | A1 | 12/2014 |
| WO | 2015000800 | A1 | 1/2015 |
| WO | 2015048563 | A2 | 4/2015 |
| WO | 2015063127 | A1 | 5/2015 |
| WO | 2015106286 | A1 | 7/2015 |
| WO | 2015172894 | A1 | 11/2015 |
| WO | 2016005367 | A1 | 1/2016 |
| WO | 2016025913 | A1 | 2/2016 |
| WO | 2016029159 | A2 | 2/2016 |
| WO | 2016033369 | A1 | 3/2016 |
| WO | 2016033372 | A1 | 3/2016 |
| WO | 2016064761 | A1 | 4/2016 |
| WO | 2016110804 | A1 | 7/2016 |
| WO | 2016112398 | A1 | 7/2016 |
| WO | 2016172239 | A1 | 10/2016 |
| WO | 2017005661 | A1 | 1/2017 |
| WO | 2017011410 | A1 | 1/2017 |
| WO | 2017024276 | A1 | 2/2017 |
| WO | 2017035512 | A1 | 3/2017 |
| WO | 2017044904 | A1 | 3/2017 |
| WO | 2017058913 | A1 | 4/2017 |
| WO | 2017062508 | A1 | 4/2017 |
| WO | 2017117450 | A1 | 7/2017 |
| WO | 2017146659 | A1 | 8/2017 |
| WO | 2017188965 | A1 | 11/2017 |
| WO | 2018033591 | A2 | 2/2018 |
| WO | 2018039296 | A2 | 3/2018 |
| WO | 2018039458 | A1 | 3/2018 |
| WO | 2018063879 | A1 | 4/2018 |
| WO | 2018093765 | A1 | 5/2018 |
| WO | 2018106843 | A1 | 6/2018 |
| WO | 2018140531 | A1 | 8/2018 |
| WO | 2018148844 | A1 | 8/2018 |
| WO | 2018217791 | A1 | 11/2018 |
| WO | 2019211314 | A1 | 11/2019 |
| WO | 2020028088 | A1 | 2/2020 |
| WO | 2020041502 | A1 | 2/2020 |
| WO | 2020041633 | A1 | 2/2020 |
| WO | 2020236946 | A1 | 11/2020 |
| WO | D215131-0001 | | 7/2022 |
| WO | 2022221442 | A1 | 10/2022 |

OTHER PUBLICATIONS

Widmer, C. et al., "Inferring latent task structure for multitask learning by multiple kernel learning", BMC Bioinformatics, (2010), vol. 11, pp. 1-8.

Wiley, J. D. et al., "Analysis and Control of the Current Distribution under Circular Dispersive Electrodes", Biomedical Engineering, IEEE Transactions on BME, (1982), vol. 29, No. 5, pp. 381-385.

Winter, D. et al., "An integrated EMG/biomechanical model of upper body balance and posture during human gait", Progress in Brain Research, (1993), vol. 97, Ch. 32, pp. 359-367.

Wirz, M. et al., "Effectiveness of automated locomotor training in patients with chronic incomplete spinal cord injury: a multicenter trial", Archives of Physical Medicine and Rehabilitation, (2005), vol. 86, No. 4, pp. 672-680.

Yakovenko, S. et al., "Spatiotemporal Activation of Lumbosacral Motoneurons in the Locomotor Step Cycle", Journal of Neurophysiology, (2002), vol. 87, No. 3, pp. 1542-1553.

YouTube video entitled: "How to Round Corners in Illustrator," uploaded Sep. 6, 2017 by user "Mohamed Achraf" [retrieved on Jul. 7, 2022]. Retrieved from the Internet: <URL:https://www.youtube.com/watch?v=q8Cyd0sqY6A>, 3 pages.

Zhang, T. C. et al., "Mechanisms and models of spinal cord stimulation for the treatment of neuropathic pain", Brain Research, (2014), vol. 1569, pp. 19-31.

Zorner, B. et al., "Profiling locomotor recovery: comprehensive quantification of impairments after CNS damage in rodents", Nature Methods, (2010), vol. 7, No. 9, pp. 701-708.

Communication Pursuant to Rule 114(2) EPC in counterpart European Patent Application No. 12847885.6 mailed Mar. 27, 2015, 28 pages.

Communication Regarding Extended European Search Report in counterpart European Patent Application No. 24153829.7 mailed May 22, 2024, 8 pages.

Cotton, D. P. J. et al., "A Multifunctional Capacitive Sensor for Stretchable Electronic Skins", IEEE Sensors Journal, IEEE Service Center, New York, NY, US, (2009), vol. 9, No. 12, pp. 2008-2009.

Coursera, "What is Machine Learning? Definition, Types, and Examples," Coursera, May 20, 2025. Retrieved from the Internet: <URL:https://www.coursera.org/articles/what-is-machine-learning>, 12 pages.

Courtine, G. et al., "Can experiments in nonhuman primates expedite the translation of treatments for spinal cord injury in humans?", Nature Medicine, (2007), vol. 13, No. 5, pp. 561-566.

Courtine, G. et al., "Modulation of multisegmental monosynaptic responses in a variety of leg muscles during walking and running in humans", Journal of Physiology, (2007), vol. 582, No. 3, pp. 1125-1139.

Courtine, G. et al., "Recovery of supraspinal control of stepping via indirect propriospinal relay connections after spinal cord injury", Nature Medicine, (2008), vol. 14, No. 1, pp. 69-74.

Courtine, G. et al., "Transformation of nonfunctional spinal circuits into functional states after the loss of brain input", Nature Neuroscience, (2009), vol. 12, No. 10, pp. 1333-1342.

Cowley, K. et al., "Propriospinal neurons are sufficient for bulbospinal transmission of the locomotor command signal in the neonatal rat spinal cord", The Journal of Physiology, (2008), vol. 586, No. 6, pp. 1623-1635.

Cyganowski, A et al., "Stretchable electrodes for neuroprosthetic interfaces", Sensors, 2012 IEEE, Taipei, (2012), pp. 1-4.

Dani, V. et al., "Stochastic Linear Optimization Under Bandit Feedback", In Proceedings of the 21st Annual Conference on Learning Theory (COLT), (2008), No. 101, pp. 1-15.

Danner, S. et al., "Human Spinal locomotor control is based on flexibly organized burst generators", Brain: A Journal of Neurology, (2015), vol. 138, No. 3, pp. 577-588.

Danner, S. M. et al., "Body Position Influences Which neural structures are recruited by lumbar transcutaneous spinal cord stimulation", PLoS ONE, (2016), vol. 11, No. 1, pp. 1-13.

Danner, S. M. et al., "Can the Human Lumbar Posterior cols. be Stimulated by Transcutaneous Spinal Cord Stimulation? A modeling study", Europe PMC funders author manuscripts, Artificial Organs, (2011), vol. 35, No. 3, pp. 257-262.

Decision to Refuse a European Patent Application in counterpart European Patent Application No. 15834593.4 mailed Oct. 28, 2021, 24 pages.

Definition of "Insert", Dictionary [online], Oxford English Dictionary, 2020 [retrieved on Dec. 15, 2022], 2 pages.

Desantana, J. M. et al., "Effectiveness of Transcutaneous Electrical Nerve Stimulation for Treatment of Hyperalgesia and Pain", Current Rheumatology Reports, (2008), vol. 10, pp. 492-499.

Dimitrijevic, M. M. et al. "Evidence for a Spinal Central Pattern Generator in Humans", Annals New York Academy Sciences, (1998), vol. 860, No. 1, pp. 360-376.

(56)  References Cited

OTHER PUBLICATIONS

Dimitrijevic, M. M. et al., "Clinical Elements for the Neuromuscular Stimulation and Functional Electrical Stimulation protocols in the Practice of Neurorehabilitation", Artificial Organs, vol. 26, No. 4, (2002), pp. 256-259.

Dimitrijevic, M. R. et al., "Electrophysiological characteristics of H-reflexes elicited by percutaneous stimulation of the cauda equina", Abstract No. 4927, 34th Annual Meeting of the Society for Neuroscience, San Diego, CA (2004), 1 page.

Dominici, N. et al. "Versatile robotic interface to evaluate, enable and train locomotion and balance after neuromotor disorders", Nature Medicine, (2012), vol. 18, No. 7, pp. 1-8.

Drew, T. et al., "Cortical mechanisms involved in visuomotor coordination during precision walking", Brain Research Reviews, (2008), vol. 57, No. 1, pp. 199-211.

Drummond, G. B. et al., "Thoracic impedance used for measuring chest wall movement in postoperative patients", British Journal of Anaesthesia, (1996), vol. 77, No. 3, pp. 327-332.

Dubinsky, R. M. et al., "Assessment: Efficacy of transcutaneous electric nerve stimulation in the treatment of pain in neurologic disorders (an evidenced-based review)", Report of the Therapeutics and Technology Assessment Subcommittee of the American Academy of Neurology, Neurology, (2010), vol. 74, No. 2, pp. 173-176.

Dunne, L. et al., "Initial development and testing of a novel foam-based pressure sensor for wearable sensing", Journal of NeuroEngineering and Rehabilitation, (2005), vol. 2, No. 4, pp. 1-7.

Duschau-Wicke, A. et al., "Patient-cooperative control increases active participation of individuals with SCI during robot-aided gait training", Journal of NeuroEngineering and Rehabilitation, (2010), vol. 7, No. 43, pp. 1-13.

Edgerton, V. et al., "Robotic Training and Spinal Cord Plasticity", Brain Research Bulletin, (2009), vol. 78, No. 1, pp. 4-12.

Edgerton, V. et al., "Training Locomotor Networks", Brain Research Reviews, (2008), vol. 57, No. 1, pp. 241-254.

Edgerton, V. R. et al., "Epidural stimulation of the spinal cord in spinal cord injury: current status and future challenges", Expert Review of Neurotherapeutics, (2011), vol. 11, No. 10, pp. 1351-1353.

EPO Communication and Supplementary European Search Report in counterpart European Patent Application No. 17745012.9 mailed Aug. 13, 2019, 8 pages.

European Opposition filed in counterpart European Patent Application No. 17826212.7 mailed Dec. 2, 2022, 56 pages.

European Reply to Communication in counterpart European Patent Application No. 12847885.6 mailed Oct. 24, 2016, 4 pages.

Extended European Search Report in counterpart European Patent Application No. 14765477.6 mailed Nov. 8, 2016, 10 pages.

Extended European Search Report in counterpart European Patent Application No. 14849355.4 mailed May 10, 2017, 7 pages.

Extended European Search Report in counterpart European Patent Application No. 15834593.4 mailed Apr. 4, 2018, 7 pages.

Extended European Search Report in counterpart European Patent Application No. 15836927.2 mailed Mar. 1, 2018, 9 pages.

Extended European Search Report in counterpart European Patent Application No. 16825005.8 mailed Feb. 19, 2019, 8 pages.

Extended European Search Report in counterpart European Patent Application No. 16833973.7 mailed Dec. 13, 2018, 6 pages.

Extended European Search Report in counterpart European Patent Application No. 18173218.1 mailed Jan. 7, 2019, 6 pages.

Extended European Search Report in counterpart European Patent Application No. 18744685.1 mailed Sep. 7, 2020, 8 pages.

Extended European Search Report in counterpart European Patent Application No. 19201998.2 mailed Apr. 21, 2020, 7 pages.

Extended European Search Report in counterpart European Patent Application No. 19211738.0 mailed May 27, 2020, 8 pages.

Extended European Search Report in counterpart European Patent Application No. 19851613.0 mailed Apr. 19, 2022, 9 pages.

Extended European Search Report in counterpart European Patent Application No. 19852797.0 mailed Apr. 19, 2022, 6 pages.

Extended European Search Report in counterpart European Patent Application No. 20020190.3 mailed Oct. 5, 2020, 7 pages.

Extended European Search Report in counterpart European Patent Application No. 20163794.9 mailed Sep. 18, 2020, 7 pages.

Extended European Search Report in counterpart European Patent Application No. 20164082.8 mailed Jul. 21, 2020, 7 pages.

Extended European Search Report in counterpart European Patent Application No. 20175385.2 mailed Jan. 22, 2021, 8 pages.

Extended European Search Report in counterpart European Patent Application No. 21166801.7 mailed Aug. 17, 2021, 11 pages.

Extended European Search Report in counterpart European Patent Application No. EP12847885.6 mailed May 6, 2015, 7 pages.

Levine, A. et al., "Identification of cellular node for motor control pathways", Nature Neuroscience, (2014), vol. 17, No. 4, pp. 586-593.

Liu, J. et al., "Stimulation of the parapyramidal region of the neonatal rat brain stem produces locomotor-like activity involving spinal 5-HT7 and 5-HT2A receptors", Journal of Neurophysiology, (2005), vol. 94, No. 2, pp. 1392-1404.

Lizotte, D. et al., "Automatic gait optimization with Gaussian process regression", In IJCAI, (2007), vol. 7, pp. 944-949.

Lovely, R. et al., "Effects of Training on the Recovery of Full-Weight-Bearing Stepping in the Adult Spinal Cat", Experimental Neurology, (1986), vol. 92, No. 2, pp. 421-435.

Lozano, A. et al., "Probing and Regulating Dysfunctional Circuits Using Deep Brain Stimulation", Neuron, (2013), vol. 77, No. 3, pp. 406-424.

Lu, D. et al., "Engaging cervical spinal cord networks to re-enable volitional control of hand function in tetraplegic patients", Neurorehabilitation and Neural Repair, (2016), vol. 30, No. 10, pp. 951-962.

McIntyre, C. et al., "Modeling the Excitability of Mammalian Nerve Fibers: Influence of Afterpotentials on the Recovery Cycle", Journal of Neurophysiology, (2002), vol. 87, No. 2, pp. 995-1006.

Meacham, K. W. et al., "A lithographically-patterned, elastic multi-electrode array for surface stimulation of the spinal cord", Biomed Microdevices, (2008), vol. 10, pp. 259-269.

Metzger, C. et al., "Flexible-foam-based capacitive sensor arrays for object detection at law cost", Applied Physics Letters, American Institute of Physics, (2008), vol. 92, No. 1, pp. 13506-1-13506-3.

Minassian, K. et al., "Human lumbar cord circuitries can be activated by extrinsic tonic input to generate locomotor- like activity", Human Movement Science, (2007), vol. 26, No. 2, pp. 275-295.

Minassian, K. et al., "Human Lumbar Cord Model of the Locomotor Central Pattern Generator", Second Congress International Society of Intraoperative Neurophysiology (ISIN), (2009), pp. 11-13.

Minassian, K. et al., "Mechanisms of rhythm generation of the human lumbar spinal cord in repose to tonic stimulation without and with step-related sensory feedback", Biomedical Technology, (2013), vol. 58, (Suppl. 1), pp. 1-3.

Minassian, K. et al., "Neuromodulation of lower limb motor control in restorative neurology", Clinical Neurology and Neurosurgery, (2012), vol. 114, No. 5, pp. 489-497.

Minassian, K. et al., "Neurophysiology of the human lumbar locomotor pattern generator", Proceedings 10th Vienna International Workshop on Functional Electrical Stimulation, Center for Medical Physics and Biomedical Engineering, (2010), pp. 259-261.

Minassian, K. et al., "Peripheral and Central Afferent Input to the Lumbar Cord", Biocybernetics and Biomedical Engineering, (2005), vol. 25, No. 3, pp. 11-29.

Minassian, K. et al., "Posterior root-muscle reflex", Second Congress International Society of Intraoperative Neurophysiology (ISIN), Dubrovnik, Croatia, (2009), pp. 77-80.

Minassian, K. et al., "Posterior root-muscle reflexes elicited by transcutaneous stimulation of the human lumbosacral cord", Muscle and Nerve, (2007), vol. 35, No. 3, pp. 327-336.

Minassian, K. et al., "Stepping-like movements in humans with complete spinal cord injury induced by epidural stimulation of the lumbar cord: electromyographic study of compound muscle action potentials", Spinal Cord, (2004), vol. 42, No. 7, pp. 401-416.

Minassian, K. et al., "Transcutaneous spinal cord stimulation", International Society for Restoration Neurology, (2011), pp. 1-6.

(56)         References Cited

OTHER PUBLICATIONS

Minassian, K. et al., "Transcutaneous stimulation of the human lumbar spinal cord: Facilitating locomotor output in spinal cord injury", Society for Neuroscience, Conference Proceedings, Neuroscience 2010, San Diego, CA, Abstract Viewer/ Itinerary Planner No. 286.19, Abstract & Poster attached, (2010), 2 pages.

Minev, I. R. et al., "Electronic dura mater for long-term multimodal neural interfaces—with supplementary materials", Science, (2015), vol. 347, No. 6218, pp. 1-64.

Minev, I. R. et al., "Evaluation of an Elastomer Based Gold Microelectrode Array for Neural Recording Applications", Proceedings of the 5th International IEEE/EMBS Conference on Neural Engineering, Cancun, Mexico, (2011), pp. 482-485.

Minev, I. R. et al., "High sensitivity recording of afferent nerve activity using ultra- compliant microchannel electrodes: an acute in vivo validation", Journal of Neural Engineering, (2012), vol. 9, No. 2, pp. 1-7.

Minoux, M., "Accelerated greedy algorithms for maximizing submodular set functions", Optimization Techniques, LNCS, (1978), pp. 234-243.

Moraud, E. et al., "Mechanisms Underlying the Neuromodulation of Spinal Circuits for Correcting Gait and Balance Deficits after Spinal Cord Injury", Neuron, (2016), vol. 89, No. 4, pp. 814-828.

Murg, M. et al., "Epidural electric stimulation of posterior structures of the human lumbar spinal cord: 1. Muscle twitches—a functional method to define the site of stimulation", Spinal Cord, (2000), vol. 38, No. 7, pp. 394-402.

Musienko, P. et al., "Combinatory Electrical and Pharmacological Neuroprosthetic Interfaces to Regain Motor Function After Spinal Cord Injury", IEEE Transactions on Biomedical Engineering, (2009), vol. 56, No. 11, pp. 2707-2711.

Musienko, P. et al., "Controlling specific locomotor behaviors through multidimensional monoaminergic modulation of spinal circuitries", The Journal of Neuroscience, (2011), vol. 31, No. 25, pp. 9264-9278.

Musienko, P. et al., "Multi-system neurorehabilitative strategies to restore motor functions following severe spinal cord injury", Experimental Neurology, (2012), vol. 235, No. 1, pp. 100-109.

Musselman, K. et al., "Spinal Cord Injury Functional Ambulation Profile: A New Measure of Walking Ability", Neurorehabilitation and Neural Repair, (2011), vol. 25, No. 3, pp. 285-293.

Nandra, M. et al., "Microelectrode Implants for Spinal Cord Stimulation in Rats", Doctor of Philosophy Thesis, California Institute of Technology, (2014), pp. 1-104.

Nandra, M. S. et al., "A parylene-based microelectrode array implant for spinal cord stimulation in rats", Conference Proceedings IEEE Engineering in Medicine and Biology Society, (2011), pp. 1007-1010.

Nandra, M. S. et al., "A wireless microelectrode implant for spinal cord stimulation and recording in rats", Presentation Abstract, (2013), pp. 1-104.

Needle, A. R. et al., "Brain Regulation of muscle tone in healthy and functionally unstable ankles", Journal of Sport Rehabilitation, (2013), vol. 22, No. 3, pp. 202-211.

Nessler, J. et al., "A Robotic Device for Studying Rodent Locomotion After Spinal Cord Injury", IEEE Transactions on Neural Systems and Rehabilitation Engineering, (2005), vol. 13, No. 4, pp. 497-506.

Niu, T. et al., "A Proof-of-Concept Study of Transcutaneous Magnetic Spinal Cord Stimulation for Neurogenic Bladder", Scientific Reports, (2018), vol. 8, No. 1, pp. 1-12.

Park, K. J. et al., "Continuous "Over and Over" Suture for Tricuspid Ring Annuloplasty", Korean Journal of Thoracic and Cardiovascular Surgery, (2012), vol. 45, No. 1, pp. 19-23.

Peachpit, "Working with Basic Shapes in Adobe Illustrator CC (2014 release)," PeachPit, Nov. 3, 2014 [retrieved on Feb. 6, 2024]. Retrieved from the Internet: <URL: https://www.peachpit.com/articles/article.aspx?p=2253413&seqNum=3>.

Pearson, K. G., "Generating the walking gait: role of sensory feedback", Progress in Brain Research, (2004), vol. 143, Chapter 12, pp. 123-129.

Pellinen, D.S. et al., "Multifunctional Flexible Parylene-Based Intracortical Microelectrodes", Proceedings of the 2005 IEEE: Engineering in Medicine and Biology 27th Annual Conference, (2005), pp. 5272-5275.

Pflug, H. et al., "Parallel Resonant Inductive Wireless Power Transfer", IEEE, Proceedings of Wireless Power Week 2019, London, United Kingdom (2019), pp. 182-187.

Phillips, A. A. et al., "Contemporary Cardiovascular Concerns after Spinal Cord Injury: Mechanisms, Maladaptations, and Management", Journal of Neurotrama, (2015), vol. 32, No. 24, pp. 1927-1942.

Phillips, A. et al., "Perturbed and spontaneous regional cerebral blood flow responses to changes in blood pressure secondary high-level spinal cord injury: the effect of midodrine", Journal of Applied Physiology, (2014), vol. 116, No. 6, pp. 645-653.

Phillips, A. et al., "Regional neurovascular coupling and cognitive performance in those with low blood pressure secondary to high-level spinal cord injury: improved by alpha-1 agonist midodrine hydrochloride", Journal of Cerebral Blood Flow & Metabolism, (2014), vol. 34, No. 5, pp. 794-801.

Pratt, G. et al., "Stiffness Isn't Everything", Proceedings of the Fourth International Symposium on Experimental Robotics, (1995), pp. 1-6.

Pratt, J. et al., "Series elastic actuators for high fidelity force control", Industrial Robot: An International Journal, (2002), vol. 29, No. 3, pp. 234-241.

Prochazka, A. et al., "Ensemble firing of muscle afferents recorded during normal locomotion in cats", The Journal of Physiology, (1998), vol. 507, No. 1, pp. 293-304.

Prochazka, A. et al., "Models of ensemble firing of muscle spindle afferents recorded during normal locomotion in cats", The Journal of Physiology, (1998), vol. 507, No. 1, pp. 277-291.

Pudo, D. et al., "Estimating Intensity Fluctuations in High Repetition Rate Pulse Trains Generated Using the Temporal Talbot Effect", IEEE Photonics Technology Letters, (2006), vol. 18, No. 5, pp. 658-660.

Purves, D. et al., "Autonomic Regulation of the Bladder", Neuroscience, 2nd edition, Chapter Twenty-One, Sunderland, (MA), (2022), pp. 1-5.

Rasmussen, C. E. et al., "Gaussian Processes for Machine Learning (GPML) Toolbox", The Journal of Machine Learning Research, (2010), vol. 11, pp. 3011-3015.

Rasmussen, C. E. et al., "Gaussian Processes for Machine Learning", The MIT Press, Cambridge, Massachusetts, (2006), pp. 1-266.

Rasmussen, C. E., "Gaussian Processes in Machine Learning", LNAI, (2003), vol. 3176, pp. 63-71.

Rattay, F. et al., "Epidural electrical stimulation of posterior structures of the human lumbosacral cord: 2. Quantitative analysis by computer modeling", Spinal Cord, (2000), vol. 38, No. 8, pp. 473-489.

Reinkensmeyer, D. et al., "Tools for understanding and optimizing robotic gait training", Journal of Rehabilitation Research & Development, (2006), vol. 43, No. 5, pp. 657-670.

Rejc, E. et al., "Effects of Lumbosacral Spinal Cord Epidural Stimulation for Standing after Chronic Complete Paralysis in Humans", PLoS One, (2015), vol. 10, No. 7, pp. 1-20.

Robbins, H., "Some Aspects of the Sequential Design of Experiments", Bulletin of the American Mathematical Society, (1952), vol. 58, pp. 527-535.

Robinson, A. et al., "Hybrid stretchable circuits on silicone substrate", Journal of Applied Physics, (2014), vol. 115, No. 14, pp. 143511-1-143511-5.

Rodger, D. C. et al., "High Density Flexible Parylene-Based Multielectrode Arrays for Retinal and Spinal Cord Stimulation", Proc. of the 14th International Conference on Solid-State Sensors, Actuators and Microsystems, (2007), pp. 1385-1888.

Rosenzweig, E. et al., "Extensive Spontaneous Plasticity of Corticospinal Projections After Primate Spinal Cord Injury—with supplementary materials", Nature Neuroscience, (2010), vol. 13, No. 12, pp. 1505-1510.

(56)                    References Cited

OTHER PUBLICATIONS

Roy, F. D. et al., "Effect of percutaneous stimulation at different spinal levels on the activation of sensory and motor roots", Experimental Brain Research, (2012), vol. 223, pp. 281-289.

Rubinstein et al., "Current Density Profiles of Surface Mounted and Recessed Electrodes for Neural Prostheses", Biomedical Engineering, IEEE Transactions on BME, (1987), vol. 34, No. 11, pp. 864-875.

Ryzhov, I. O. et al., "The knowledge gradient algorithm for a general class of online learning problems", Operations Research, (2012), vol. 60, No. 1, pp. 1-47.

Sayenko, D. et al., "Neuromodulation of evoked muscle potentials induced by epidural spinal-cord stimulation in paralyzed individuals", Journal of Neurophysiology, (2014), vol. 111, No. 5, pp. 1088-1099.

Sayenko, D. G. et al., "Spinal segment-specific transcutaneous stimulation differentially shapes activation pattern among motor pools in humans", Journal of Applied Physiology, (2015), vol. 118, No. 11, pp. 1364-1374.

Schmidlin, E. et al., "Behavioral Assessment of Manual Dexterity in Non-Human Primates", Journal of Visualized Experiments, (2011), vol. 57, No. e3258, pp. 1-11.

Seifert, H. M. et al., "Restoration of Movement Using Functional Electrical Stimulation and Bayes' Theorem", The Journal of Neuroscience, (2002), vol. 22, No. 21, pp. 9465-9474.

Shafik, A. et al., "Extrapelvic cavernous nerve stimulation in erectile dysfunction. Human Study", Andrologia, (1996), vol. 28, No. 3, pp. 151-156.

Shafik, A. et al., "Magnetic stimulation of the cavernous nerve for the treatment of erectile dysfunction in humans", International Journal of Impotence Research, (2000), vol. 12, No. 3, pp. 137-141.

Shamir, R. et al., "Machine learning approach to optimizing combined stimulation and medication therapies for Parkinson's disease—with supplementary materials", Brain Stimulation, (2015), vol. 8, No. 6, pp. 1025-1032.

Sharpe, A. et al., "Upper-limb muscles responses to epidural, subdural and intraspinal stimulation of the cervical spinal cord", Journal of Neural Engineering, (2014), vol. 11, No. 1, pp. 1-16.

Sherman, J. et al., "Measurements of the normal cervical spinal cord on MR Imaging", American Journal of Neuroradiology, (1990), vol. 11, No. 2, pp. 369-372.

Srinivas, N. et al., "Gaussian process optimization in the bandit setting: No. regret and experimental design", in Proceedings of the 27th International Conference on Machine Learning, (2010), pp. 1-17.

Steward, O. et al., "False Resurrections: Distinguishing Regenerated from Spared Axons in the Injured Central Nervous System", The Journal of Comparative Neurology, (2003), vol. 459, No. 1, pp. 1-8.

Stienen, A. et al., "Analysis of reflex modulation with a biologically realistic neural network", Journal of Computer Neuroscience, (2007), vol. 23, pp. 333-348.

Sun, F. et al., "Sustained axon regeneration induced by co-deletion of PTEN and SOCS3—with supplementary material", Nature, (2011), vol. 480, No. 7377, pp. 372-375.

Suzuki, T. et al., "A 3D flexible parylene probe array for multichannel neural recording", IEEE Neural Engineering, (2003), pp. 154-156.

Szava, Z. et al., "Transcutaneous electrical spinal cord stimulation: Biophysics of a new rehabilitation method after spinal cord injury", VDM Publishing, Saarbrucken, Germany, (2011), pp. 1-95.

Takeoka, A. et al., "Muscle Spindle Feedback Directs Locomotor Recovery and Circuit Reorganization after Spinal Cord Injury", Cell, (2014), vol. 159, No. 7, pp. 1626-1639.

Takeuchi, S. et al., "3D flexible multichannel neural probe array", Journal of Micromechanics and Microengineering, (2004), vol. 14, No. 1, pp. 104-107.

Tanabe, S. et al., "Effects of transcutaneous electrical stimulation combined with locomotion-like movement in the treatment of post-stroke gait disorder: a single-case study", (2008), vol. 30, No. 5, pp. 411-416.

Temel, Y. et al., "Case Report—Deep brain stimulation of the thalamus can influence penile erection", International Journal of Impotence Research, (2004), vol. 16, No. 1, pp. 91-94.

Tenne, Y. et al., "Computational Intelligence in Expensive Optimization Problems", Adaptation, Learning, and Optimization, Springer, Berlin Heidelberg, (2010), vol. 2, pp. 131-162.

Timoszyk, W. et al., "Hindlimb loading determines stepping quantity and quality following spinal cord transection", Brain Research, (2005), vol. 1050, No. 1-2, pp. 180-189.

Troni, W. et al., "A methodological reappraisal of non invasive high voltage electrical stimulation of lumbosacral nerve roots", Clinical Neurophysiology, (2011), vol. 122, No. 10, pp. 2071-2080.

Tungjitkusolmun, S. et al., "Finite element analyses of uniform current density electrodes for radio-frequency cardiac ablation", IEEE Transactions on Biomedical Engineering, (2000), vol. 47, No. 1, pp. 32-40.

Valchinov, E. S. et al., "An active electrode for biopotential recording from small localized bio-sources", BioMedical Engineering OnLine, (2004), vol. 3, No. 25, pp. 1-14.

Vallery, H. et al., "Compliant Actuation of Rehabilitation Robots", IEEE Robotics & Automation Magazine, (2008), vol. 15, No. 3, pp. 60-69.

Van Den Brand, R. et al., "Restoring Voluntary Control of Locomotion after Paralyzing Spinal Cord Injury", Science Magazine, (2012), vol. 336, No. 6085, pp. 1182-1185.

Wan, D. et al., "Life-threatening outcomes associated with autonomic dysreflexia: A clinical review", Journal of Spinal Cord Medicine, (2014), vol. 37, No. 1, pp. 2-10.

Wang, J. M. et al., "Gaussian process dynamical models for human motion", IEEE Transactions on Pattern Analysis and Machine Intelligence, (2007), vol. 30, No. 2, pp. 283-298.

Wang, T. et al., "Incidence of C5 nerve root palsy after cervical surgery—A meta-analysis for decade", Medicine, (2017), vol. 96, No. 45, pp. 1-14.

Ward, A. R. et al., "Sensory, motor, and pain thresholds for stimulation with medium frequency alternating current", Archives of Physical Medicine and Rehabilitation, (1998), vol. 79, No. 3, pp. 273-278.

Ward, A. R., "Electrical Stimulation Using Kilohertz-Frequency Alternating Current", Physical Therapy, (2009), vol. 89, No. 2, pp. 181-190.

Wei, P. et al., "Stretchable microelectrode array using room-temperature liquid alloy interconnects", Journal of Micromechanics and Microengineering, (2011), vol. 21, No. 054015, pp. 1-8.

Wenger, N. et al., "Closed-loop neuromodulation of spinal sensorimotor circuits controls refined locomotion after complete spinal cord injury", Science Translational Medicine, (2014), vol. 6, Issue 255, pp. 1-11.

Wenger, N. et al., "Spatiotemporal neuromodulation therapies engaging muscle synergies improve motor control after spinal cord injury - with supplementary material", Natural Medicine, (2016), vol. 22, No. 2, pp. 138-145.

Wenger, N. et al., "Supplementary Materials for Closed-loop neuromodulation of spinal sensorimotor circuits controls refined locomotion after complete spinal cord injury", Science Translational Medicine, (2014), vol. 6, Iss. 255, pp. 1-14.

Wernig, A. et al., "Laufband locomotion with body weight support improved walking in persons with severe spinal cord injuries", International Medical Society of Paraplegia, (1992), vol. 30, No. 4, pp. 229-238.

Wernig, A., "Ineffectiveness of Automated Locomotor Training", Archives of Physical Medicine and Rehabilitation, (2005), vol. 86, No. 12, pp. 2385-2386.

Extended European Search Report in counterpart European Patent Application No. 19211698.6 mailed May 28, 2020, 6 pages.

Feng, G. H. et al., "Universal concept for fabricating micron to millimeter sized 3-D parylene structures on rigid and flexible substrates", in Proc. IEEE 15th Internal Conference on Micro Electro Mechanical System, Kyoto, Japan, (2003), pp. 594-597.

(56)			References Cited

OTHER PUBLICATIONS

Fleshman, J. et al., "Electronic Architecture of Type-Identified a-Motoneurons in in the Cat Spinal Cord", Journal of Neurophysiology, (1988), vol. 60, No. 1, pp. 60-85.
Fong, A J. et al., "Recovery of control of posture and locomotion after a spinal cord injury: solutions staring US in the face", Progress in Brain Research, Elsevier Amsterdam, Netherlands, (2009), vol. 175, Chapter 25, pp. 393-418.
Frey, M. et al., "A Novel Mechatronic Body Weight Support System", IEEE Transactions on Neural Systems and Rehabilitation Engineering, (2006), vol. 14, No. 3, pp. 311-321.
Fuentes, R. et al., "Spinal Cord Stimulation Restores Locomotion in Animal Models of Parkinson's Disease," Science, (2009), vol. 323, No. 5921, pp. 1578-1582.
Ganley, K. J. et al., "Epidural Spinal Cord Stimulation Improves Locomotor Performance in Low ASIA C, Wheelchair-Dependent, Spinal Cord-Injured Individuals: Insights from Metabolic Response", Topics in Spinal Cord Injury Rehabilitation, (2005), vol. 11, No. 2, pp. 50-63.
Gerasimenko, Y. et al., "Initiation and modulation of locomotor circuitry output with multisite transcutaneous electrical stimulation of the spinal cord in noninjured humans", Journal of Neurophysiology, (2015), vol. 113, No. 3, pp. 834-842.
Gerasimenko, Y. et al., "Noninvasive Reactivation of Motor Descending Control after Paralysis", Journal of Neurotrauma, (2015), vol. 32, No. 24, pp. 1968-1980.
Gerasimenko, Y. et al., "Novel and Direct Access to the Human Locomotor Spinal Circuitry", Journal of Neuroscience, (2010), vol. 30, No. 10, pp. 3700-3708.
Gerasimenko, Y. et al., "Spinal cord reflexes induced by epidural spinal cord stimulation in normal awake rats", Journal of Neuroscience Methods, (2006), vol. 157, No. 2, pp. 253-263.
Gerasimenko, Y. et al., "Transcutaneous electrical spinal-cord stimulation in humans", Annals of Physical and Rehabilitation Medicine, (2015), vol. 58, No. 4, pp. 225-231.
Gerasimenko, Y. P. et al., "Control of Locomotor Activity in Humans and Animals in the Absence of Supraspinal Influences", Neuroscience and Behavioral Physiology, (2002), vol. 32, No. 4, pp. 417-423.
Gerasimenko, Y. P. et al., "Epidural Spinal Cord Stimulation Plus Quipazine Administration Enable Stepping Complete Spinal Adult Rats", Journal of Neurophysiology, (2007), vol. 98, No. 5, pp. 2525-2536.
Gilja, V. et al., "A high-performance neural prosthesis enabled by control algorithm design—with supplementary materials", Nature Neuroscience, (2012), vol. 15, No. 12, pp. 1-56.
Ginsbourger, D. et al., "Kriging is well-suited to parallelize optimization", Computational Intelligence in Expensive Optimization Problems, Berlin, Heidelberg: Springer Berlin Heidelberg, (2010), Ch. 6, pp. 131-162.
Gittins, J.C., "Bandit Processes and Dynamic Allocation Indices", Journal of the Royal Statistical Society B, (1979), vol. 41, No. 2, pp. 148-164.
Giuliano, F. et al., "Neural Control of Erection", Physiology & Behavior, (2004), vol. 83, No. 2, pp. 189-201.
Graf, N. et al., "Electrochemically Stimulated Release from Liposomes Embedded in a Polyelectrolyte Multilayer", Advanced Functional Materials, (2011), vol. 21, No. 9, pp. 1666-1672.
Graz, I. et al., "Flexible ferroelectret field-effect transistor for large-area sensor skins and microphones", Applied Physics Letters, American Institute of Physics, (2006), vol. 89, No. 7, pp. 73501-1-73501-3.
Graz, I. et al., "Silicone substrate with in situ strain relief for stretchable thin-film transistors", Applied Physics Letters, AIP, American Institute of Physics, (2011), vol. 98, No. 12, pp. 124101-1-124101-3.
Guyatt, G. et al., "The 6-minute walk: a new measure of exercise capacity in patients with chronic heart failure", Canadian Medical Association Journal, (1985), vol. 132, No. 8, pp. 919-923.

Hagglund, M. et al., "Activation of groups of excitatory neurons in the mammalian spinal cord or hindbrain evokes locomotion", Nature Neuroscience, (2010), vol. 13, No. 2, pp. 246-252.
Harkema, S. et al., "Effect of Epidural stimulation of the lumbosacral spinal cord on voluntary movement, standing, and assisted stepping after motor complete paraplegia: a case study", Lancet, (2011), vol. 377, No. 9781, pp. 1938-1947.
Harkema, S. et al., "Human Lumbosacral Spinal Cord Interprets Loading During Stepping", Journal of Neurophysiology, (1997), vol. 77, No. 2, pp. 797-811.
Harkema, S. et al., "Normalization of Blood Pressure with Spinal Cord Epidural Stimulation After Severe Spinal Cord Injury", Frontiers in Human Neuroscience, (2018), vol. 12, pp. 1-11.
Harrison, P. et al., "Individual Excitatory Post-Synaptic Potentials Due to Muscle Spindle la Afferents in Cat Triceps Surae Motoneurones", The Journal Physiology, (1981), vol. 312, No. 1, pp. 455-470.
Hashtrudi-Zaad, K. et al., "On the Use of Local Force Feedback for Transparent Teleoperation", Proceedings of the 1999 IEEE International Conference on Robotics and Automation, (1999), vol. 3, pp. 1863-1869.
Health Journalism Glossary: Bidirectional, Definition [online], Association of Health Care Journalists, 2024. Retrieved from the Internet: <URL:https://healthjournalism.org/glossary-terms/bidirectional/>, 3 pages.
Hennig, P. et al., "Entropy search for information-efficient global optimization", Journal of Machine Learning Research (JMLR), (2012), vol. 13, No. 1, pp. 1809-1837.
Herman, R. et al., "Spinal cord stimulation facilitates functional walking in a chronic, incomplete spinal cord injured", Spinal Cord, (2002), vol. 40, No. 2, pp. 65-68.
Hidler, J. et al., "ZeroG: Overground gait and balance training system", Journal of Rehabilitation Research & Development, (2011), vol. 48, No. 4, pp. 287-298.
Hines, M. et al., "The NEURON Simulation Environment", Neural Computation, (1997), vol. 9, No. 6, pp. 1179-1209.
Hofstoetter, U. S. et al., "Modification of spasticity by transcutaneous spinal cord stimulation in individuals with incomplete spinal cord injury", The Journal of Spinal Cord Medicine, (2014), vol. 37, No. 2, pp. 202-211.
Hofstoetter, U.S. et al., "Effects of transcutaneous spinal cord stimulation on voluntary locomotor activity in an incomplete spinal cord injured individual", Biomedical Technology, (2013), vol. 58 (Suppl. 1), pp. 1-3.
Hofstoetter, U.S. et al., "Modification of Reflex Responses to Lumbar Posterior Root Stimulation by Motor Tasks in Healthy Subjects", Artificial Organs, (2008), vol. 32, No. 8, pp. 644-648.
Hofstotter, U.S. et al., "Model of spinal cord reflex circuits in humans: Stimulation frequency-dependence of segmental activities and their interactions", Second Congress International Society of Intraoperative Neurophysiology (ISIN), Dubrovnik, Croatia, (2009), pp. 1-149.
Hohenschurz-Schmidt, D. J. et al., "Linking Pain Sensation to the Autonomic Nervous System: The Role of the Anterior Cingulate and Periaqueductal Gray Resting-State Networks", Front Neuroscience, (2020), vol. 14, No. 147, pp. 1-15.
Hovey, C. et al., "The New Guide to Magnet Stimulation", The Magstim Company Ltd., (2006), pp. 1-45.
Hung, C. C. et al., "Transparent microprobe array fabricated by MEMS hot embossing technology for photodynamic therapy application", IEICE Electronics Express, (2010), vol. 7, No. 9, pp. 569-576.
Ichiyama, R. M. et al., "Hindlimb stepping movements in complete spinal rats induced by epidural spinal cord stimulation", Neuroscience Letters, (2005), vol. 383, No. 3, pp. 339-344.
International Search Report and Written Opinion issued in counterpart PCT Application No. EP2020/063564, mailed Sep. 11, 2020, 12 pages.
International Search Report and Written Opinion issued in counterpart PCT Application No. PCT/EP2017/083478, mailed May 3, 2018, 10 pages.
International Search Report and Written Opinion issued in counterpart PCT Application No. PCT/EP2018/082939, mailed Feb. 14, 2019, 11 pages.

(56) References Cited

OTHER PUBLICATIONS

International Search Report and Written Opinion issued in counterpart PCT Application No. PCT/EP2018/082942, mailed Feb. 14, 2019, 11 pages.
International Search Report and Written Opinion issued in counterpart PCT Application No. PCT/EP2020/053381, mailed May 12, 2020, 8 pages.
International Search Report and Written Opinion issued in counterpart PCT Application No. PCT/EP2020/063563, mailed Jul. 30, 2020, 14 pages.
International Search Report and Written Opinion issued in counterpart PCT Application No. PCT/US2012/064878 mailed Mar. 19, 2013, 11 pages.
International Search Report and Written Opinion issued in counterpart PCT Application No. PCT/US2014/029340 mailed Aug. 6, 2014, 11 pages.
International Search Report and Written Opinion issued in counterpart PCT Application No. PCT/US2014/057886 mailed Dec. 24, 2014, 6 pages.
International Search Report and Written Opinion issued in counterpart PCT Application No. PCT/US2015/011263 mailed May 19, 2015, 12 pages.
International Search Report and Written Opinion issued in counterpart PCT Application No. PCT/US2015/046378 mailed Dec. 1, 2015, 5 pages.
International Search Report and Written Opinion issued in counterpart PCT Application No. PCT/US2015/047268 mailed Dec. 8, 2015, 17 pages.
International Search Report and Written Opinion issued in counterpart PCT Application No. PCT/US2015/047272 mailed Dec. 3, 2015, 11 pages.
International Search Report and Written Opinion issued in counterpart PCT Application No. PCT/US2016/041802 mailed Sep. 12, 2016, 17 pages.
International Search Report and Written Opinion issued in counterpart PCT Application No. PCT/US2016/045898 mailed Dec. 5, 2016, 13 pages.
International Search Report and Written Opinion issued in counterpart PCT Application No. PCT/US2016/049129 mailed Dec. 5, 2016, 13 pages.
International Search Report and Written Opinion issued in counterpart PCT Application No. PCT/US2017/015435, mailed May 8, 2017, 9 pages.
International Search Report and Written Opinion issued in counterpart PCT Application No. PCT/US2018/015098 mailed Mar. 12, 2018, 9 pages.
International Search Report and Written Opinion issued in counterpart PCT Application No. PCT/US2018/033942 mailed Aug. 31, 2018, 8 pages.
International Search Report and Written Opinion issued in counterpart PCT Application No. PCT/US2019/047551 mailed Nov. 21, 2019, 9 pages.
International Search Report and Written Opinion issued in counterpart PCT Application No. PCT/US2019/047777 mailed Nov. 14, 2019, 15 pages.
International Search Report and Written Opinion issued in counterpart PCT Application No. PCT/US2020/033830 mailed Oct. 14, 2020, 10 pages.
International Search Report and Written Opinion issued in counterpart PCT Application No. PCT/US2022/024673 mailed Jun. 28, 2022, 8 pages.
International Search Report issued in counterpart PCT Application No. PCT/US2012/020112 mailed Jul. 30, 2012, 4 pages.
International Search Report issued in counterpart PCT Application No. PCT/US2012/022257 mailed Sep. 3, 2012, 4 pages.
International Search Report issued in counterpart PCT Application No. PCT/US2012/030624 mailed Oct. 31, 2012, 3 pages.
International Search Report issued in counterpart PCT Application No. PCT/US2012/064874 mailed Mar. 19, 2013, 4 pages.

Ivanenko, Y. P. et al., "Temporal Components of the Motor Patterns Expressed by the Human Spinal Cord Reflect Foot Kinematics", Journal of Neurophysiology, (2003), vol. 90, No. 5, pp. 3555-3565.
Iyer, P. C. et al., "Characterization of stimulus response curves obtained with transcranial magnetic stimulation from bilateral tibialis anterior muscles post stroke", Neuroscience Letters, (2019), vol. 713, pp. 1-15.
Jaman, R., "A retrospective cross-sectional survey of lumbo-sacral recorded at the D.U.T. Chiropractic Day Clinic (1995-2005)", (2014). Durban University of Technology, Master's Degree in Technology dissertation. Retrieved from the Internet: <URL: https://doi.org/10.51415/10321/221>, 94 pages.
Jarosiewicz, B. et al., "Supplementary Materials for Virtual typing by people with tetraplegia using a self-calibrating intracortical brain-computer interface", Science Translational Medicine, (2015), vol. 7, No. 313, pp. 1-26.
Jarosiewicz, B. et al., "Virtual typing by people with tetraplegia using a self-calibrating intracortical brain-computer interface", Science Translational Medicine, (2015), vol. 7, No. 313, pp. 1-11.
Jenny, A. B. et al., "Principles of Motor Organization of the Monkey Cervical Spinal Cord", The Journal of Neuroscience, (1983), vol. 3, No. 3, pp. 567-575.
Jilge, B. et al., "Initiating extension of the lower limbs in subjects with complete spinal cord injury by epidural lumbar cord stimulation", Experimental Brain Research, (2004), vol. 154, pp. 308-326.
Johnson, W. et al., "Application of a Rat Hindlimb Model: A Prediction of Force Spaces Reachable Through Stimulation of Nerve Fascicles", IEEE Transactions on Bio- Medical Engineering, (2011), vol. 58, No. 12, pp. 3328-3338.
Jones, D. R. et al., "Efficient Global Optimization of Expensive Black-Box Functions", Journal of Global Optimization, (1998), vol. 13, pp. 455-492.
Jones, K. et al., "Computer Simulation of the Responses of Human Motoneurons to Composite 1A EPSPS: Effects of Background Firing Rate", The Journal of Physiology, (1997), vol. 77, No. 1, pp. 405-420.
Jonic, S. et al., "Three machine learning techniques for automatic determination of rules to control locomotion", IEEE Transactions on Biomedical Engineering, (1999), vol. 46, No. 3, pp. 300-310.
Kakulas, A. B., "A Review of the Neuropathology of Human Spinal Cord Injury with Emphasis on Special Features", Proceedings of the Donald Munro Memorial Lecture at the American Paraplegia Society 44th Annual Conference, Las Vegas, NV, Spinal Cord, (1999), vol. 22, No. 2, pp. 119-124.
Kapetanakis, S. et al., "Cauda Equina Syndrome Due to Lumbar Disc Herniation: a Review of Literature", Folia Medica, (2017), vol. 59, No. 4, pp. 377-386.
Kim, W. S. et al., "Ultra-sensitive Flexible Pressure Sensor with Stamped Polyurethane Rubber", 2011 11th IEEE Conference on Nanotechnology, (2011), pp. 1607-1610.
Kim, Y. et al., "Electrical behavior of defibrillation and pacing electrodes", Proceedings of the IEEE, (2002), vol. 84, No. 3, pp. 446-456.
Kirazh, O. et al., "Anatomy of the spinal dorsal root entry zone: its clinical significance", Acta Neurochirurgica, (2014), vol. 156, pp. 2351-2358.
Kirkwood, P., "Neuronal Control of Locomotion: From Mollusc to Man", G.N. Orlovsky, T.G. Deliagina and S. Grillner. Oxford University Press, Oxford, 1999. ISBN 0198524056 (Hbk), 322 pp., Clinical Neurophysiology, vol. 111, (2000): 1524-1525.
Kitano, K. et al., "Spinal reflex in human lower leg muscles evolved by transcutaneous spinal cord stimulation", Journal of Neuroscience Methods, (2009), vol. 180, No. 1, pp. 111-115.
Kleinberg, R. et al., "Multi-armed bandits in metric spaces", In STOC, Computer and Automation Research Institute of the Hungarian Academy of Sciences, Budapest, Hungary, (2008), pp. 1-26.
Kocsis, L. et al., "Bandit Based Monte-Carlo Planning", European Conference on Machine Learning, Springer, Berlin, Heidelberg, (2006), pp. 282-293.
Kondo, T. et al., "Laser monitoring of chest wall displacement", European Respiratory Journal, (1997), vol. 10, No. 8, pp. 1865-1869.

(56)　　　　References Cited

OTHER PUBLICATIONS

Krassioukov, A. et al., "A Systematic Review of the Management of Autonomic Dysreflexia Following Spinal Cord Injury", Archives of Physical Medicine and Rehabilitation, (2009), vol. 90, No. 4, pp. 682-695.
Krassioukov, A. et al., "A Systematic Review of the Management of Orthostatic Hypotension Following Spinal Cord Injury", Archives of Physical Medicine and Rehabilitation, (2009), vol. 90, No. 5, pp. 876-885.
Krause, A. et al., "Contextual Gaussian Process Bandit Optimization", in Advances in Neural Information Processing Systems (NIPS), (2011), pp. 1-9.
Krause, A. et al., "Near-optimal Nonmyopic Value of Information in Graphical Models", In UAI, (2005), pp. 1-8.
Krause, A. et al., "Near-Optimal Sensor Placements in Gaussian Processes: Theory, Efficient Algorithms and Empirical Studies", Journal of Machine Learning Research, (2008), vol. 9, pp. 235-284.
Krenn, M. et al., "Selectivity of transcutaneous stimulation of lumbar posterior roots at different spinal levels in humans", Biomedical Technology, (2013), vol. 58 (Suppl. 1), pp. 1-2.
Kwakkel, G. et al., "Effects of Robot-assisted therapy on upper limb recovery after stroke: A Systematic Review", Neurorehabilitation and Neural Repair, (2008), vol. 22, No. 2, pp. 111-121.
Lacour, S. et al., "Flexible and stretchable micro-electrodes for in vitro and in vivo neural interfaces", Medical & Biological Engineering & Computing, (2010), vol. 48, pp. 945-954.
Lacour, S. et al., "Stretchable gold conductors on elastomeric substrates", Applied Physics Letters, (2003), vol. 82, No. 15, pp. 2404-2406.
Ladenbauer, J. et al., "Stimulation of the human lumbar spinal cord with implanted and surface electrodes: a computer simulation study", IEEE Transactions on Neural Systems and Rehabilitation Engineering, (2010), vol. 18, No. 6, pp. 637-645.
Lavrov, I. et al., "Epidural Stimulation Induced Modulation of Spinal Locomotor Networks in Adult Spinal Rats", Journal of Neuroscience, (2008), vol. 28, No. 23, pp. 6022-6029.
Abernethy, J. et al., "Competing in the dark: An efficient algorithm for bandit linear optimization", Conference on Learning Theory, (2009), No. 110, pp. 1-13.
Ada, L. et al., "Mechanically assisted walking with body weight support results in more independent walking than assisted overground walking in non-ambulatory patients early after stroke: a systematic review", Journal of Physiotherapy, (2010), vol. 56, No. 3, pp. 153-161.
Alto, L. et al., "Chemotropic guidance facilitates axonal regeneration and synapse formation after spinal cord injury", Nature Neuroscience, (2009), vol. 12, No. 9, pp. 1106-1113.
Anderson, K., "Targeting recovery: priorities of the spinal cord-injured population", Journal of Neurotrauma, (2004), vol. 21, No. 10, pp. 1371-1383.
Andersson, K. E. et al., "CNS Involvement in Overactive Bladder—Pathophysiology and Opportunities for Pharmacological Intervention", Drugs, (2003), vol. 63, No. 23, pp. 2595-2611.
Angeli, C. et al., "Altering spinal cord excitability enables voluntary movements after chronic complete paralysis in humans", Brain: A Journal of Neurology, (2014), vol. 137, No. 5, pp. 1394-1409.
Anonymous, "Re: Round corners (fillet) in Illustrator CS6", in: Stack Exchange [online], Graphic Design, Jan. 22, 2018; 17:52 [retrieved on Feb. 6, 2024]. Retrieved from the Internet: <URL:https://graphicdesign.stackexchange.com/questions/104349/round-corners-fillet-in-illustrator-cs6>, 10 pages.
Anonymous, Lumbar Decompression Surgery: When it's used, Datasheet [online], National Health Service, 2022. Retrieved from the Internet: <URL:https://www.nhs.uk/conditions/lumbar-decompression-surgery/why-its-done/#:-:text=Cauda%equina%20syndrome%20a.is%20severe%20or%20getting%20worse, 2 pages.
Anonymous, Vital Signs, Datasheet [online], Cleveland Clinic [retrieved on Nov. 22, 2021]. Retrieved from the Internet: <URL:https://my.clevelandclinic.org/health/articles/10881-vital-signs, 19 pages.

Ateh, D. D. et al., "Polypyrrole-based conducting polymers and interactions with biological tissues", Journal of the Royal Society Interface, (2006), vol. 3, No. 11, pp. 741-752.
Auer, P. et al., "Finite-time analysis of the multiarmed bandit problem", Machine Learning, (2002), vol. 47, No. 2, pp. 235-256.
Auer, P., "Using confidence bounds for exploitation-exploration trade-offs", Journal of Machine Learning Research, (2002), vol. 3, pp. 397-422.
Axisa, F. et al., "Elastic and Conformable Electronic Circuits and Assemblies using MID in polymer", 6th International Conference on Polymers and Adhesives in Microelectronics and Photonics, IEEE Polytronic 2007 Conference, (2007), pp. 280-286.
Azimi, J. et al., "Batch Active Learning via Coordinated Matching", in Proceedings of the 29th International Conference on Machine Learning, (2012), pp. 1-8.
Azimi, J. et al., "Batch Bayesian Optimization via Simulation Matching", in Advances in Neural Information Processing Systems (NIPS), (2010), pp. 1-9.
Azimi, J. et al., "Hybrid Batch Bayesian Optimization", in Proceedings of the 29th International Conference on Machine Learning, (2012), pp. 1-12.
Barbeau, H. et al., "Recovery of locomotion after chronic spinalization in the adult cat", Brain Research, (1987), vol. 412, No. 1, pp. 84-95.
Bareyre, F. et al., "The injured spinal cord spontaneously forms a new intraspinal circuit in adult rats", Nature Neuroscience, (2004), vol. 7, No. 3, pp. 269-277.
Basso, D. et al., "MASCIS Evaluation of Open Field Locomotor Scores: Effects of Experience and Teamwork on Reliability", Journal of Neurotrauma, (1996), vol. 13, No. 7, pp. 343-359.
Bizzi, E. et al., "Modular organization of motor behavior", Zeitschrift für Naturforschung, (1998), vol. 53, No. 7-8, pp. 510-517.
Brochu, et al., "A Tutorial on Bayesian Optimization of Expensive Cost Functions, with Application to Active User Modeling and Hierarchical Reinforcement Learning", In TR-2009-23, UBC, (2009), pp. 1-49.
Brosamle, C. et al., "Cells of Origin, Course, and Termination Patterns of the Ventral, Uncrossed Component of the Mature Rat Corticospinal Tract", The Journal of Comparative Neurology, (1997), vol. 386, No. 2, pp. 293-303.
Bruckenstein, S. et al., "An experimental study of nonuniform current distribution at rotating disk electrodes", Journal of the Electrochemical Society, (1970), vol. 117, No. 8, pp. 1044-1048.
Bubeck, S. et al., "Online Optimization in X-Armed Bandits", Advances in Neural Information Processing Systems (NIPS), (2008), pp. 1-8.
Bubeck, S. et al., "Pure Exploration in Finitely-Armed and Continuous-Armed Bandits problems", in ALT, (2009), pp. 1-35.
Burke, R., "Group Ia Synaptic Input to Fast and Slow Twitch Motor Units of Cat Triceps Surae", The Journal of Physiology, (1968), vol. 196, No. 3, pp. 605-630.
Cai, L. et al., "Implications of Assist-As-Needed Robotic Step Training after a Complete Spinal Cord Injury on Intrinsic Strategies of Motor Learning", The Journal of Neuroscience, (2006), vol. 26, No. 41, pp. 10564-10568.
Capogrosso, M. et al., "A Brain-Spinal Interface Alleviating Gait Deficits after Spinal Cord Injury in Primates", Nature, (2016), vol. 539, No. 7628, pp. 284-288.
Capogrosso, M. et al., "A Computational Model for Epidural Electrical Stimulation of Spinal Sensorimotor Circuits", Journal of Neuroscience, (2013), vol. 33, No. 49, pp. 19326-19340.
Carhart, M. et al., "Epidural Spinal-Cord Stimulation Facilitates Recovery of Functional Walking Following Incomplete Spinal-Cord Injury", IEEE Transactions on Neural Systems and Rehabilitation Engineering, (2004), vol. 12, No. 1, pp. 32-42.
Chatagny, P. et al., "Distinction between hand dominance and hand preference in primates: a behavioral investigation of manual dexterity in nonhuman primates (macaques) and human subjects", Brain and Behavior, (2013), vol. 3, No. 5, pp. 575-595.
Colgate, E. et al., "An Analysis of Contact Instability in Terms of Passive Physical Equivalents", Proceedings of the 1989 IEEE International Conference on Robotics and Automation, Scottsdale, Arizona, (1989), pp. 404-409.

(56)                     References Cited

OTHER PUBLICATIONS

Communication Pursuant to Article 94(3) EPC in counterpart European Application No. 19209911.7 mailed Jul. 20, 2023, 5 pages.

Communication Pursuant to Article 94(3) EPC in counterpart European Application No. 19209911.7 mailed Mar. 1, 2023, 2 pages.

Communication Pursuant to Article 94(3) EPC in counterpart European Patent Application No. 12760696.0 mailed Nov. 9, 2017, 5 pages.

Communication Pursuant to Article 94(3) EPC in counterpart European Patent Application No. 12847885.6 mailed Apr. 15, 2016, 5 pages.

Communication Pursuant to Article 94(3) EPC in counterpart European Patent Application No. 12847885.6 mailed Feb. 16, 2017, 5 pages.

Communication Pursuant to Article 94(3) EPC in counterpart European Patent Application No. 12848368.2 mailed May 9, 2018, 5 pages.

Communication Pursuant to Article 94(3) EPC in counterpart European Patent Application No. 14765477.6 mailed Nov. 14, 2018, 5 pages.

Communication Pursuant to Article 94(3) EPC in counterpart European Patent Application No. 14765477.6 mailed Sep. 27, 2019, 6 pages.

Communication Pursuant to Article 94(3) EPC in counterpart European Patent Application No. 14849355.4 mailed Jul. 20, 2018, 6 pages.

Communication Pursuant to Article 94(3) EPC in counterpart European Patent Application No. 15834593.4 mailed Jul. 17, 2019, 4 pages.

Communication Pursuant to Article 94(3) EPC in counterpart European Patent Application No. 15834593.4 mailed Jul. 30, 2020, 5 pages.

Communication Pursuant to Article 94(3) EPC in counterpart European Patent Application No. 17826212.7 mailed Dec. 21, 2020, 7 pages.

Communication Pursuant to Article 94(3) EPC in counterpart European Patent Application No. 18807366.2 mailed Mar. 22, 2023, 4 pages.

Communication Pursuant to Article 94(3) EPC in counterpart European Patent Application No. 20160841.1 mailed Mar. 6, 2024, 5 pages.

Communication Pursuant to Article 94(3) EPC in counterpart European Patent Application No. 20726108.2 mailed Mar. 20, 2024, 4 pages.

Communication Pursuant to Article 94(3) EPC in counterpart European Patent Application No. 211660801.7 mailed Mar. 7, 2024, 6 pages.

Communication Pursuant to Article 94(3) EPC in counterpart European Patent Application No. 21166801.7 mailed Mar. 7, 2024, 6 pages.

Communication Pursuant to Article 94(3) EPC in counterpart European Patent Application No. 24153829.7 mailed Apr. 4, 2025, 5 pages.

Extended European Search Report in counterpart European Patent Application No. 23189900.6 dated Jan. 4, 2024, (7 pages).

Aching knee or sore back? New app helps doctors treat pain, medicalxpress.com. May 8, 2017, Retrieved from the Internet: <URL: https://medicalxpress.com/news/2017-05-aching-knee-sore-app-doctors. html>, 1 page.

Back pain and body posture infographic, Alamy.com. Apr. 11, 2017, Retrieved from the Internet: <URL:https://www.alamy.com/stock-photo-back-pain-and-body-posture-infographic-with-anatomical-illustrations-141494074.html?imageid=27CC5905-F123-4DSC-847A4C76D50631C1&p=313080&pn=1&searchId=526c9d4db7f91a3e259d7b785fa370c3&searchtype=0>, 2 pages.

Extended European Search Report in EP25165562.7, mailed Sep. 2, 2025, 9 pages.

Ichiyama et al. "Step training reinforces specific spinal locomotor circuitry in adult spinal rats." Journal of Neuroscience 28.29 (2008): 7370-7375.

Male and female muscle and skeletal systems, Shutterstock.com. Jan. 15, 2021, Retrieved from the Internet: <URL: https://www.shutterstock.com/image-illustration/male-female-muscle-skeletal-systems-xray-1895443960>, 2 pages.

Screenshots of the electric patient-reported outcome app final prototype, Researchgate.net. Oct. 2020, Retrieved from the Internet: <URL:https://www.researchgate.net/figure/Screenshots-of-the-electronic-patient-reported-outcome-app-final-prototype_fig>, 1 page.

* cited by examiner

100

Pulse Generator <u>200</u>

300

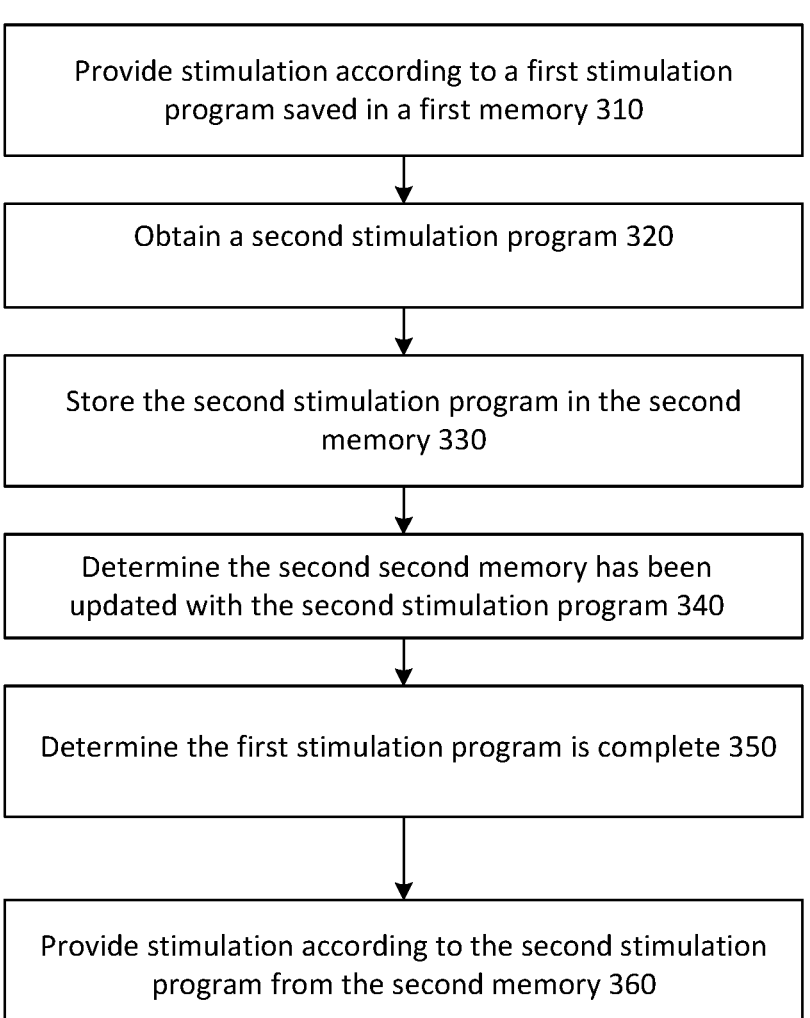

Provide stimulation according to a first stimulation program saved in a first memory 310

Obtain a second stimulation program 320

Store the second stimulation program in the second memory 330

Determine the second second memory has been updated with the second stimulation program 340

Determine the first stimulation program is complete 350

Provide stimulation according to the second stimulation program from the second memory 360

Receive a stimulation parameter
update 410

Store the stimulation parameter
update in a parameter memory 420

Access the parameter memory to read
the updated stimulation parameter
before generating a new pulse 430

Provide a next stimulation pulse according
to the updated stimulation parameter 440

NEUROMODULATION SYSTEM

TECHNICAL FIELD

The disclosed systems and methods concern updating stimulation settings for neuromodulation and/or neurostimulation systems. In particular, the disclosed systems and methods concern updating stimulation programs and/or parameters without interrupting the delivery of stimulation.

BACKGROUND

Neuromodulation and/or neurostimulation systems can address physical or neurological injuries, diseases, or conditions of a patient by providing stimulation to the patient. Conventional neurostimulation systems can be designed to provide stimulation according to a previously programmed configuration, either continuously or in response to satisfaction of a condition. Such designs may require that stimulation be stopped prior to updating stimulation settings (electrode configurations, amplitude, frequency, etc.).

SUMMARY

The disclosed systems and methods relate to a stimulation updating system. The stimulation updating system can include a pulse generator (e.g., an implanted or external pulse generator) configured with alternatively accessible program memories. The pulse generator can be configured to update a second program memory with a second stimulation program without interrupting the execution of a first stimulation program stored in a first program memory. Furthermore, in some embodiments, the pulse generator can be configured to support updating at least one stimulation parameter while performing stimulation.

Embodiments of the present disclosure include a neuromodulation system. The neuromodulation system can include an implantable pulse generator. The implantable pulse generator can be configured to provide neuromodulation to a patient based on a sequence of neuromodulation programs. The implantable pulse generator can include alternately accessible memories. A second memory of the alternately accessible memories can be configured for storing a second neuromodulation program while the implantable pulse generator provides neuromodulation according to a first neuromodulation program stored in a first memory of the memories.

Embodiments of the present disclosure include a method for providing neuromodulation according to a sequence of neuromodulation programs. The method can include an operation of receiving a second neuromodulation program in the sequence of neuromodulation programs. The second neuromodulation program can be received by the implantable pulse generator and during provision of neuromodulation according to a first neuromodulation program in the sequence of neuromodulation programs. The first neuromodulation program can be read from a first memory of the implantable pulse generator. The method can include an operation of storing the second neuromodulation program. The second neuromodulation program can be stored in a second memory of the implantable pulse generator. The method can include an operation of providing neuromodulation according to the second neuromodulation program stored in the second memory. The neuromodulation can be provided by the implantable pulse generator and upon completion of the provision of the neuromodulation according to the first neuromodulation program.

It is to be understood that both the foregoing general description and the following detailed description are exemplary and explanatory only and are not restrictive of the disclosed embodiments, as claimed.

BRIEF DESCRIPTION OF THE FIGURES

The drawings are not necessarily to scale or exhaustive. Instead, emphasis is generally placed upon illustrating the principles of the embodiments described herein. The accompanying drawings, which are incorporated in and constitute a part of this specification, illustrate several embodiments consistent with the disclosure and, together with the description, serve to explain the principles of the disclosure. In the drawings:

FIG. 3 depicts an exemplary process for providing updated stimulation programs without ceasing stimulation, according to some embodiments of the present disclosure.

DETAILED DESCRIPTION

Figure 1:
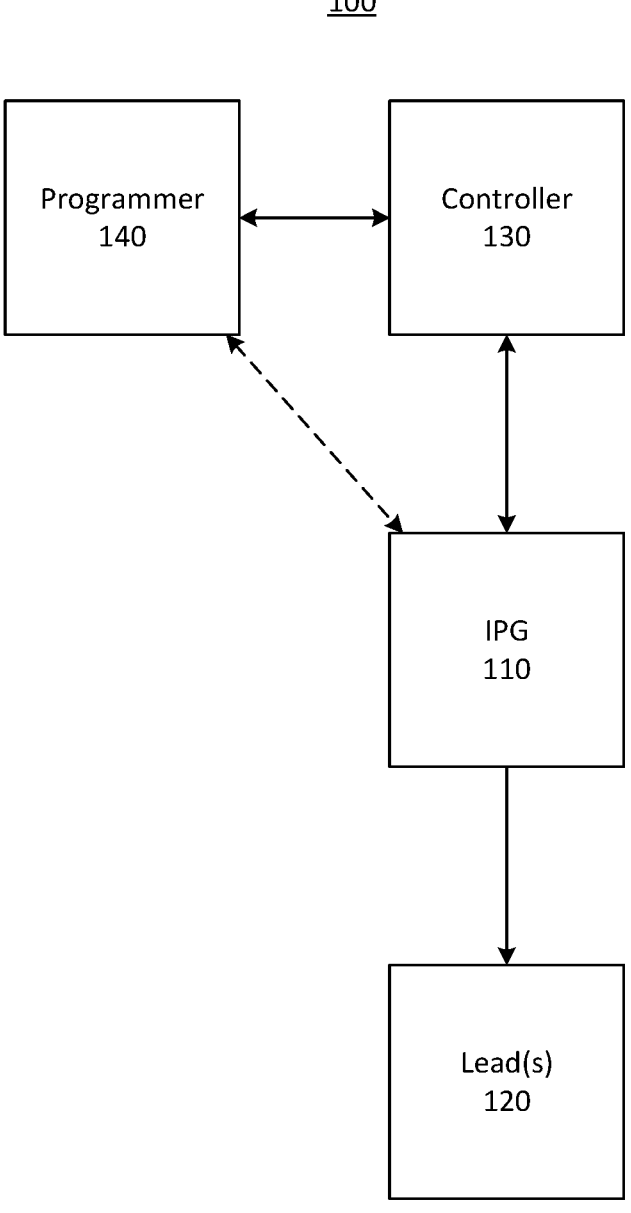
FIG. 1 depicts an exemplary system for providing stimulation to one or more patients, according to some embodiments of the present disclosure.

Reference will now be made in detail to exemplary embodiments, discussed with regards to the accompanying drawings. In some instances, the same reference numbers will be used throughout the drawings and the following description to refer to the same or like parts. Unless otherwise defined, technical or scientific terms have the meaning commonly understood by one of ordinary skill in the art. The disclosed embodiments are described in sufficient detail to enable those skilled in the art to practice the disclosed embodiments. It is to be understood that other embodiments may be utilized and that changes may be made without departing from the scope of the disclosed embodiments. Thus, the materials, methods, and examples are illustrative only and are not intended to be necessarily limiting.

Conventional neurostimulation systems may require that stimulation be stopped prior to updating stimulation parameters. However, this requirement may pose a problem for patients. Patients that rely on stimulation for the proper operation of nerves, organs, or other structures may be harmed when stimulation stops. Furthermore, stopping stimulation may interrupt patient activities (e.g., standing, locomotion, reaching and grasping, or the like) with potentially catastrophic consequences. Accordingly, updating stimulation settings may be a significant, potentially dangerous act for such patients. Patients may therefore choose to update stimulation settings infrequently, or only under clinician supervision, limiting the benefit provided by conventional neurostimulation systems.

Conventional neurostimulation systems may be unable to provide complicated patterns of stimulation. Implantable neurostimulators, in particular, can be limited to simple stimulation patterns by memory or processing constraints. As described herein, a neurostimulation system can address this problem using a programmer or controller in combination with an implantable neurostimulator. The programmer or controller can be programmed with one or more stimulator partitures. These stimulation partitures can include multiple channels of stimulation. The programmer or controller can select and provide the appropriate stimulation partiture to the implantable neurostimulator as needed. In this manner, the neurostimulation system can circumvent the memory or processing constraints of the implantable neurostimulator. However, this architecture may require that the implantable neurostimulator be able to update stimulation parameters while continuing to provide stimulation.

Emerging neurostimulation techniques can use complicated stimulation patterns to provide greater therapeutic benefits to patients. For example, such stimulation patterns can target individual leg muscles with different patterns of stimulation at different times in a gate cycle or stand-and-transfer motion. As an additional example, such stimulation patterns could enable bladder contractions while also mitigating autonomic dysreflexia triggered by a concomitant increase in bladder pressure. Conventional neurostimulation systems that cannot update stimulation parameters without ceasing stimulation may not support these beneficial emerging techniques.

The disclosed embodiments enable a neurostimulator to update stimulation parameters while continuing to provide stimulation. The disclosed embodiments can therefore benefit patients by preventing harms arising from cessation of stimulation and by enabling improved neurostimulation systems. The improved neurostimulation systems can support complicated stimulation patterns that provide greater therapeutic benefits.

Stimulation, as described herein, can include electrical stimulation. In some embodiments, stimulation can include optical, mechanical, or other suitable stimulation modalities.

Neuromodulation can include using stimulation to affect or control the operation or behavior of the nervous system, cardiac system, vascular system, gastrointestinal system, secretory system, musculature, or other excitable tissues. Neuromodulation can be used to restore function lost due to, mitigate the effects of, or compensate for injuries (e.g., spinal cord injury, stroke, or the like), diseases, disorders, or dysfunctions, including but not limited to Parkinson's Disease, Alzheimer's Disease, Huntington's Disease, Cerebral Palsy, Dystonia, Amyotrophic Lateral Sclerosis, Multiple Sclerosis. Particular applications of neuromodulation include, but are not limited to, spinal cord injuries, neurodegenerative disorders, pain, spasticity, movement disorders, epilepsy, ischaemia, cardiac disorders, bowel and bladder and sexual dysfunction, visual system disorders, auditory system disorders, and psychiatric disorders.

Consistent with disclosed embodiments, stimulation can be provided at various locations on or in the body of a patient. Stimulation can be provided to the central nervous system (e.g., within the brain and spinal cord), the peripheral nervous system, the secretory system, or the like. Stimulation can be configured to affect the sensory nervous system, the motor nervous system, the autonomic nervous system, the entric nervous system, or any combination of the forgoing. Stimulation can be provided to the spinal cord, spinal roots, dorsal root ganglions, or the like. Stimulation can be provided to particular tracts or lamina within the spinal cord. Stimulation can be provided to particular structures within the brain or brainstem, such as particular regions (e.g., thalamus, or the like), lobes (e.g., occipital lobe, or the like), or nuclei (e.g., globus pallidus or the like). Stimulation can be provided directly to muscles (e.g., using intramuscular electrodes, or the like) or sensory organs (e.g., the retina, the cochlea, carotid baroreceptors, or the like). The disclosed embodiments are not intended to be limited to any particular location or type of stimulation.

A patient, as described herein, can be the individual to whom stimulation is provided. A user, as described herein, can be the patient, a caregiver of the patient, or a service provider (e.g., a technician; a clinician, such as a doctor, nurse, rehabilitation specialist, physical therapist, or the like; or other service provider).

Stimulation parameters, as described herein, can include intensity, amplitude, duration, frequency, carrier frequency, pulse width, pulse ratio, electrode configuration, burst frequency or the like of the stimulation. In some embodiments, stimulation parameters can include inter-burst interval, number of stimulation pulses in a burst, inter-pulse interval, first phase stimulation amplitude, first phase stimulation duration, first phase pulse shape, or the like. In some embodiments, stimulation parameters can include inter-phase duration and the shapes, amplitudes, durations, or the like of any subsequent phases in a stimulation pulse (e.g., second phase stimulation amplitude, second phase stimulation duration, second phase stimulation pulse shape, or the like). In some embodiments, stimulation parameters can include the choice of stimulation contacts (e.g., which electrode is used on a multi-contact electrode), stimulation polarity (e.g., monopolar, bipolar, or the like), whether the stimulation phases are charge-balanced, whether the stimulation is current or voltage controlled, or the like.

A stimulation partiture can include an arrangement of stimulation parameters for multiple stimulation channels. The stimulation partiture can specify a temporal arrangement of the stimulation parameters. For example, stimulation according to a first set of stimulation parameters can be applied to a first stimulation channel according to a first schedule, while stimulation according to a second set of stimulation parameters can be applied to a second channel according to a second schedule.

A stimulation program can specify one or more sets of stimulation parameters, one or more stimulation partitures, or any combination of the foregoing. In some embodiments, the stimulation program can package the set(s) of stimulation programs or stimulation partiture(s) for provision to the patient as a single unit. In some embodiments, a stimulation program can be created, modified, or deleted using a programmer or controller, as described herein.

In some embodiments, a stimulation program can be designed and intended to provide a particular physiological effect or effects. For example, a stimulation program can include a stimulation partiture that specifies stimulation on channels corresponding to different muscles of the feet, legs, and trunk. The stimulation partiture can define sequences of stimulation times and/or stimulation amplitudes for these stimulation channels. In this example, when stimulation is provided according to the stimulation partiture by a stimulation engine through a suitably configured arrangement of leads to a paraplegic patient, the paraplegic patient may rise to a standing position from a seated position. As may be appreciated, such a positional change requires a complex combination of muscle activations.

In some embodiments, a sequence of stimulation programs can be designed and intended to collectively provide a particular physiological effect or effects. For example, a sequence of stimulation programs can be designed such that, when the stimulation programs are sequentially provided to and executed by a by a stimulation engine through a suitably configured arrangement of leads to a paraplegic patient, the paraplegic patient can rise from a sitting position (e.g., according to a first stimulation program in the sequence) and walk (e.g., according to one or more second stimulation programs in the sequence).

The physiological effect or effects can include locomotor activity, postural control, motor activities, voluntary voiding of the bladder and/or bowel, sexual function, and autonomic nervous system control. Locomotion activity can include activities that enable the patient to move from one location to another (e.g., walking, running, crawling, or the like). Motor activities can include voluntary motions, such as movements of the upper or lower limbs, neck, shoulders, hands, fingers (e.g., grasp, pinch, hold, or the like), feet, or the like. Postural control can include maintaining, achieving, or restoring a pose, posture, or balance at rest or in motion. Autonomic function control can include maintenance or control of the sympathetic, parasympathetic, or entric nervous system. For example, autonomic function control can include maintenance or control of pupil dilation, cardiovascular function (e.g., heart rate, blood pressure, or the like), respiratory and/or coughing function, or normalized metabolic processes.

FIG. 1 depicts an exemplary system 100 for providing stimulation to one or more patients, according to some embodiments of the present disclosure. System 100 can enable flexible, customizable provision of stimulation to the patient. For convenience of description, system 100 is described as providing electrical stimulation, but the disclosed embodiments are not so limited. Furthermore, the stimulation provided can be used for neuromodulation. System 100 can therefore provide neuromodulation stimulation.

In some embodiments, neuromodulation system 100 can include an implantable pulse generator (IPG) 110, leads 120, a controller 130, and a programmer 140. IPG 110 can be configured to generate the electrical signals that are provided to the patients through leads 120. Leads 120 can be the physical interface through which the stimulations are provided to the patient. Controller 130 can be a patient-facing computing device and can enable a patient or a user to enable, disable, trigger, halt, or adjust stimulation provided by IPG 110 in accordance with a predetermined stimulation program. Programmer 140 can be a user-facing computing device and can be configured to enable a user to create, modify, or delete stimulation programs (e.g., by creating, modifying, or deleting sets of stimulation programs or partitures specified by a stimulation program).

In various embodiments, programmer 140 and external controller 130 can be implemented using the same computing device. For example, such a device can have multiple accounts having different privileges, such as a patient account and a user account. In such embodiments, a patient account can provide the functionality of external controller 130, while a user account can provide the functionality of programmer 40.

In various embodiments, an implantable controller can be used in place of external controller 130. In some such embodiments, the implantable controller 130 and IPG 110 can be combined in a single device. Alternatively, the implantable controller 130 and IPG 110 can be in separate devices.

In some embodiments, IPG 110 can be communicatively connected with leads 120. For example, leads 120 can be electrically connected to IPG 110 using connectors, as described herein. In some embodiments, IPG 110 can be communicatively connected with controller 130. In some embodiments, IPG 110 can be communicatively connected with programmer 140. IPG 110 can be configured to receive stimulation programs or instructions from controller 130 or programmer 140 and provide stimulation pulses to the patients through leads 120 according to a stimulation program.

In various embodiments, an external pulse generator can be used in place of IPG 110. For example, an external pulse generator connected to percutaneous leads can be used to determine whether a patient is responsive to stimulation. If the patient is responsive, then the patient can be outfitted with an implantable stimulator. In some such embodiments, the external pulse generator can possess functionality of implantable pulse generator 110, as described herein. Alternatively, the external pulse generator can additionally include the capabilities of controller 130 (or programmer 140).

In some embodiments, the external pulse generator and one or more of the external controller and programmer can be implemented using a single device. For example, a single device can provide the functionality of the pulse generator and the external controller, or the pulse generator, external controller, and programmer. Alternatively, the external pulse generator, external controller, and programmer can be implemented using separate devices.

Consistent with disclosed embodiments, IPG 110 can be configured to provide stimulation signals on stimulation channels. In some embodiments, the stimulation channels can be independently controllable. IPG 110 can be configured to receive instructions or a stimulation program from at least one of controller 130 or programmer 140. Such instructions can include instructions to load a stimulation program (or to load parameters that specify a stimulation program) into a memory of IPG 110. The instructions can include instructions to modify a stimulation program or delete a stimulation program from a memory of IPG 110. The instructions can include instructions to enable or disable an output of IPG 110. The instructions can include instructions to start or cease stimulation according to a stimulation partiture.

For example, IPG 110 can receive (e.g., from controller 130 or programmer 140) a first stimulation program (or parameters specifying the stimulation program) corresponding to a component of a gait cycle. IPG 110 can provide stimulation to the patient according to the stimulation program. While providing stimulation according to the first stimulation program, IPG 110 can receive another stimulation program corresponding to the next component of the gait cycle. Upon completion of stimulation according to the first stimulation program, IPG 110 can provide stimulation according to the second stimulation program. As a result of the sequential execution of such stimulation programs, the patient can move, be moved, or be assisted in moving, through a gait cycle.

In some embodiments, IPG 110 can be configured for implantation into a patient. IPG 110 can include control circuitry, communication circuitry, a stimulation engine, and a connection component. The control circuitry can include at least one processor (e.g., a microprocessor, a microcontroller, an Application Specific Integrated Circuit, or another suitable processor) and at least one memory containing instructions that control the operation of IPG 110. In some embodiments, the communication circuitry can be configured to support wireless communication with controller 130 or programmer 140. In such embodiments, the communication circuitry can include an antenna (e.g., a radio-frequency antenna, such as an antenna coil, or the like), an optical link (e.g., an optical detector, or the like), or any other suitable communication components. In some embodiments, the communication circuitry can support wired communication with controller 130 or programmer 140. In such embodiments, communication circuitry can include suitable connectors and/or connectors for created wired percutaneous connections with other components of system 100. The connection component can enable IPG 110 to connect with leads (e.g., leads 120) to provide stimulation through the leads without unacceptable signal distortion or power loss. The disclosed embodiments are not limited to any particular interconnection architecture.

In some embodiments, IPG 110 can include a power source. In some embodiments, the power source can be configured to store power for operating IPG 110 within the device (e.g., a battery, a fuel cell, or another suitable power source). In some embodiments, the power source can be configured to obtain power from an external source (which can then be stored internally, in some embodiments). For example, IPG 110 can include a radiofrequency coil for receiving externally transmitted power.

In some embodiments, IPG 110 can include a stimulation engine. In some embodiments, the stimulation engine can be configured to convert control signals into stimulation signals that can be provided to the patient. In some embodiments, the control signals can be logic signals, an array or time series of digital data, or any other suitable control signal. For example, when the stimulation is electrical stimulation, the stimulation engine can be or include one or more amplifier (s). The input to the amplifier(s) can be nanowatt or microwatt control signals and the output of the amplifier can be milliwatt voltage-controlled or current controlled-stimulation signals. The stimulation engine can include outputs corresponding to the multiple stimulation channels of IPG 110.

In some embodiments, the components of IPG 110 can be contained inside a container. The container can be sealed (e.g., hermetically sealed) to prevent or reduce communication between the environment (e.g., the implantation site within the patient) and the interior of IPG 110. In some embodiments, the container can include an electrically conductive portion. The electrically conductive portion can serve, in some instances, as a return path for current, or as a ground reference for electrical stimulation.

In some embodiments, the neuromodulation system can provide stimulation to a patient using leads 120. Leads 120 can be the interface between implantable pulse generator 110 and the patient's tissue. Leads 120 can include connectors, wiring or cabling, and stimulation contacts. Connectors can be configured to interconnect with corresponding connectors on IPG 110. Wiring or cabling can convey stimulation signals from IPG 110 to the stimulation contacts. The particular implementation of the connectors, wiring or cabling, and stimulation contacts can depend on the stimulation modality. For example, when the stimulation is electrical stimulation, the stimulation contacts can be or include electrodes (which can have contact(s)). The wiring or cabling can provide electrical connectivity from IPG 110 to the electrodes. The leads 120 can be electrically connected or communicated with implantable pulse generator 110.

The disclosed embodiments are not limited to any particular electrode design. In some embodiments, leads 120 may have optimal electrode configuration on one end and implantable pulse generator 110 on the other end. In particular, leads 120 is not limited to the size, shape or number. The electrode can be configured to place directly on nerves, or the electrode can be configured to place next to the nerves. Suitable electrode designs can include array or microarray electrodes, paddle electrodes; lead electrodes including circumferential contact(s), side contact(s), or tip contact(s); cuff electrodes; wire or microwire electrodes; or any other suitable electrode design.

The disclosed embodiments are not limited to any electrodes designed for any particular purpose. Suitable electrodes include brain-computer interface electrodes, deep brain stimulation electrodes, cochlear stimulation electrodes, retinal stimulation electrodes, vagal stimulation electrodes, spinal cord stimulation electrodes, foramen stimulation electrodes, bladder or bowel control stimulation electrodes, intramuscular stimulation electrodes, efferent stimulation electrodes, afferent stimulation electrodes, autonomic stimulation electrodes, enteric stimulation electrodes, or electrodes designed for some other suitable purpose.

Consistent with disclosed embodiments, controller 130 can be configured to enable a patient or user to enable, disable, trigger, halt, or adjust stimulation provided by IPG 110. In some embodiments, controller 130 can be an external device, while IPG 110 is implanted in the patient. In some embodiments, controller 130 can have greater processing power, memory, power usage, or the like than IPG 110. In some embodiments, controller 130 can include input/output options that IPG 110 lacks, such as physical communication ports (e.g., USB, RS232, or ethernet ports, or the like) or a display.

Consistent with disclosed embodiments, controller 130 can extend the capabilities of IPG 110. In some embodiments, controller 130 can store one or more stimulation programs for use by IPG 110. In some embodiments, controller 130 can be configured with data or instructions governing the selection and provision of stimulation programs to IPG 110. For example, controller 130 can store execution conditions or relationships for stimulation programs. Controller 130 can provide stimulation programs to IPG 110 in response to, or in accordance with, these execution conditions or relationships. In this manner, controller 130 can circumvent memory or computational limitations of IPG 110.

Consistent with disclosed embodiments, controller 130 can be configured to provide instructions to IPG 110. These instructions can include instructions to IPG 110 to load a stimulation program, modify or delete a stimulation program, enable or disable a stimulation program of IPG 110, start or cease execution of a loaded stimulation program, or at any other appropriate trigger. For example, controller 130 can receive instructions from programmer 140 that define a set of stimulation programs corresponding to a gait cycle. The instructions can also specify an execution relationship: that these stimulation programs can be provided to IPG 110 in an appropriate sequence. Then, in response to some trigger (e.g., a patient interaction with an interface of controller 130), controller 130 can provide the stimulation programs to IPG 110 in the sequence. Controller 130 can provide the stimulation partitures such that the next stimulation partiture in the gait cycle is being loaded into IPG 110, while IPG 110 is providing stimulation according to the current stimulation program in the gait cycle.

Consistent with disclosed embodiments, controller 130 can receive instructions from programmer 140. The instructions can include instructions to load a stimulation program into a memory of controller 130. The instructions can include instructions to modify or delete a stimulation program from a memory of controller 130. In some embodiments, the instructions received from programmer 140 can define sets of stimulation parameters, programs and execution conditions or relationships among these stimulation programs.

As an additional example, controller 130 can receive instructions from programmer 140 that specify a stimulation program for mitigation of autonomic dysreflexia. The instructions can also specify an execution relationship: that this stimulation program be provided to IPG 110 if the blood pressure of the patient exceeds a certain threshold level.

In some embodiments, controller 130 can include a user interface. A patient can interact with the user interface to cause controller 130 to perform certain actions. In some embodiments, these actions can depend on the instructions received by controller 130 from programmer 140. For example, the patient can cause controller 130 to provide stimulation programs received from programmer 140 to IPG 110. In some embodiments, these actions can depend on the state of IPG 110. For example, the patient can cause controller 130 to instruct IPG 110 to execute (or cease execution of) a stimulation partiture loaded onto IPG 110. The disclosed embodiments are not limited to any particular user interface implementation. In some embodiments, the user interface can be or include a graphical user interface (e.g., a screen, touchscreen, or the like), an audio user interface, a mechanical user interface (e.g., pushbutton(s), switch(es) or the like), or other suitable user interfaces.

In some embodiments, controller 130 can be configured to maintain a communication link with IPG 110. In some embodiments, the communication link can be a wireless link. For example, the communication link can be a WiFi link, a Bluetooth link, an optical link, a wireless radiofrequency telemetry link, or any other suitable link. In some embodiments, the communication link can be a wired link. The communication link can be used to exchange data and/or instructions between controller 130 and IPG 110.

As may be appreciated, the communication link may fail due to interference, a change in the relative positions of controller 130 and IPG 110, the interposition of material between controller 130 and IPG 110, a hardware or software issue in either of controller 130 or IPG 110. The disclosed embodiments are not limited to any particular reason for such a failure.

In various embodiments, controller 130 or IPG 110 can be configured to detect a failure of the communication link between controller 130 and IPG 110. Controller 130 or IPG 110 can detect a failure of the communication link using a keepalive mechanism. For example, controller 130 can provide a keepalive message to IPG 110. IPG 110 can respond to receipt of a keepalive message with a confirmation message. Receipt of the confirmation message by controller 130 can indicate that the communication link remains active (and that IPG 110 is still working). Controller 130 can repeatedly provide keepalive messages to IPG 110 (e.g., periodically or according to a schedule). As may be appreciated, in some embodiments, IPG 110 can provide the keepalive message and controller 130 can provide the confirmation message.

In some embodiments, IPG 110 can be configured to determine that the communication link has failed when it does not receive a keepalive (or confirmation) message for a predetermined period of time. In some embodiments, the period of time can be between 0.1 seconds and 5 minutes. In various embodiments, the period of time can be between 0.1 seconds and 60 seconds. In some embodiments, IPG 110 can be configured to cease providing stimulation in response to a determination that the communication link has failed. For example, when controller 130 is configured to provide IPG 110 a keepalive message every second, IPG 110 has not received a keepalive message for three seconds, and the period of time is 3 seconds, then IPG 110 can stop providing stimulation.

In some embodiments, controller 130 can be configured to determine that the communication link has failed when it does not receive a keepalive (or confirmation) message for a predetermined period of time. In such embodiments, controller 130 can notify programmer device 140 that the communication link has failed (or that the stimulation has been stopped). In some embodiments, controller 130 can notify programmer device 140 that the communication link previously failed, should IPG 110 subsequently reestablish the communication link. For example, controller 130 can track the occurrence and duration of communication link failures and subsequently provide this information to programmer 140.

Consistent with disclosed embodiments, programmer 140 can be configured to enable a user to create or arrange stimulation programs for a patient. In some embodiments, creation of a stimulation program can include the selection or adjustment of spatial and temporal parameters for stimulation. Such selection or adjustment can include the selection or adjustment of stimulation channels used, the mapping stimulation channels to particular electrodes in the patient, or the timing of stimulation on different stimulation channels. Such selection or adjustment can further include the selection or adjustment of stimulation parameters. In some embodiments, creation of a stimulation partiture can involve using another stimulation partiture as a template or basis. The other stimulation program can be a default stimulation program, a stimulation program used by another patient, or a stimulation program previously used by the current patient. Creation of the stimulation program for the current patient can include obtaining and adjusting the other stimulation program. The other stimulation program can be obtained from another device (e.g., controller 130, IPG 110, a database, another programmer, or the like).

In some embodiments, arrangement of stimulation programs can include the creation of execution relationships among stimulation programs. In some instances, a user can interact with programmer 140 to create a sequence of stimulation programs that are executed sequentially by IPG 110. In some instances, a user can interact with programmer 140 to associate conditions with the execution of the stimulation program. In various embodiments, programmer 140 can associate stimulation programs with user interface elements of controller 130 (e.g., pushbuttons or toggles), such that a patient interaction with the user interface elements can cause execution of the stimulation program.

As may be appreciated, programmer 140 can provide instructions configuring controller 130. Such instructions can include stimulation partitures and execution relationships. Furthermore, in some embodiments, programmer 140 can provide instructions directly to IPG 110. These instructions can include instructions to IPG 110 to load a stimulation program, modify or delete a stimulation program, enable or disable a stimulation partiture of IPG 110, start or cease execution of a loaded stimulation program, or the like. In this manner, a user can interact with programmer 140 to determine appropriate stimulation programs for a patient. Once the stimulation programs are determined, the user can transmit the determined stimulation programs (and any execution relationships) to controller 130. The patient (or a user) can then interact with controller 130 to cause IPG 110 to provide the intended stimulation.

Figure 2:
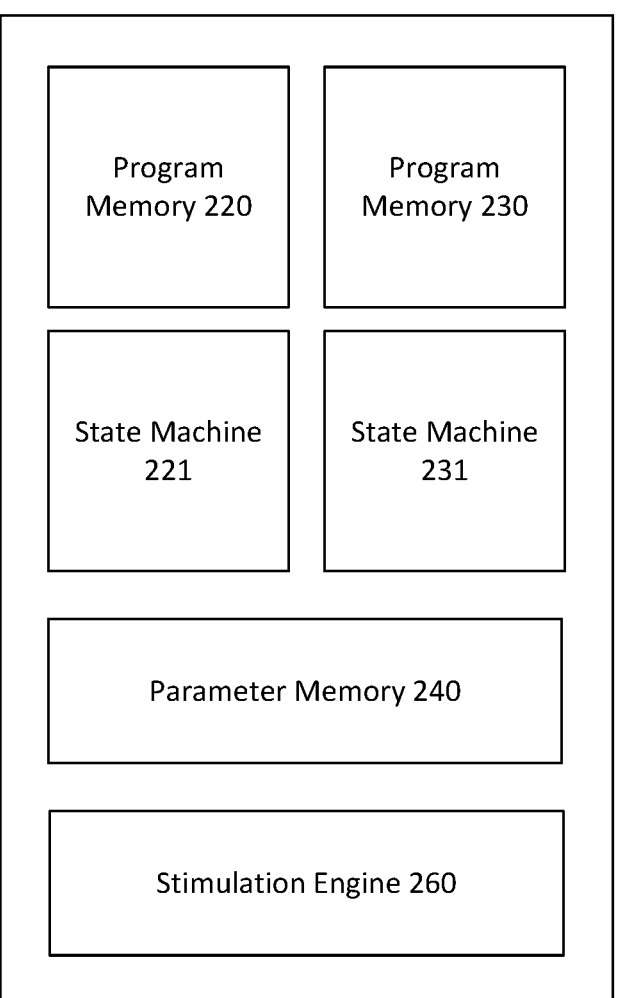
FIG. 2 depicts an exemplary schematic of a pulse generator, according to some embodiments of the present disclosure.

FIG. 2 depicts an exemplary schematic of a pulse generator 200, consistent with disclosed embodiments. Pulse generator 200 can be an external or implantable pulse generator, as described with regards to FIG. 1. In some embodiments, pulse generator 200 can be configured to include program memory 220 and program memory 230, state machine 221 and state machine 231, parameter memory 240 and stimulation engine 260. As may be appreciated, pulse generator 200 is not limited to two program memories and two state machines. Consistent with disclosed embodiments, program memory 220 and program memory 230 and state machine 221 and state machine 231 can enable pulse generator 200 to load a second stimulation program while executing the stimulation according to a first stimulation program. As may be appreciated, stimulation provided by pulse generator 200 can be used for neuromodulation.

In some embodiments, program memory 220, program memory 230 can be implemented using separate components (e.g., separate memory modules, or sets of memory modules). In some embodiments, program memory 220, program memory 230 can be implemented using separate logical areas in a unified memory (e.g., a single memory module). In such embodiments, the unified memory can be configured to support simultaneous reading and writing operations. Consistent with disclosed embodiments, each of program memory 220 and program memory 230 can be configured to store at least one stimulation program.

In some embodiments, program memory 220 and program memory 230 can be alternately accessible. In some embodiments, for example, when program memory 220 is available for writing, program memory 230 can be unavailable for writing. One or more stimulation programs can then be written to program memory 220. In some embodiments, later written stimulation programs can overwrite previously written stimulation program. When program memory 230 becomes available for writing, program memory 220 can become unavailable for writing. One or more stimulation programs can then be written to program memory 230. In some embodiments, later written stimulation programs can overwrite previously written stimulation program. In some embodiments, a program memory can be available for reading when the program memory is unavailable for writing. Consistent with disclosed embodiments, pulse generator 200 can read from one memory while writing to the other memory.

In some embodiments, state machines 221 and 231 can control reading and writing to memories 220 and 230, respectively. State machines 221 and 231 can include four or more states as described herein. The states can include a first state (e.g., "ready to update"), a second state (e.g., "updating"), a third state ("ready to execute"), and a fourth state ("executing"). The state machines can implement specific, allowable transitions between these states, as described herein. Consistent with disclosed embodiments, the state machines can be implemented using any suitable architecture. The disclosed embodiments are not limited to any particular programming language or hardware implementation.

Consistent with disclosed embodiments, state machine 221 can control memory 220 and state machine 231 can control memory 230. In some embodiments, when state machine 221 is in the fourth state (e.g., a first stimulation program stored in program memory 220 is being accessed), state machine 231 can be in the first state (e.g., program memory 230 is configured to receive and store a stimulation program). When a second stimulation program is received (e.g., as part of an update request), state machine 231 can transition to the second state (e.g., storing the second stimulation program). Once the second stimulation program is stored, state machine 231 can transition to the third state. When state machine 231 is in the third state, receipt of an execution instruction can cause state machine 231 to transition to the fourth state. In the fourth state, the second stimulation program can be queued up for outputting. Once the reading and outputting of the first stimulation program is finished, the second stimulation program can be output from program memory 230 without interrupting stimulation.

In some embodiments, when one state machine transitions from the second state to the third state, and the other state machine is already in the third state, the other state machine can transition to the first state. For example, state machine 231 can be in the third state (e.g., "ready to execute") and state machine 221 can be in the first state (e.g., "ready to update"). State machine 221 can receive an update request and transition to the second state (e.g., "updating"). When state machine 221 completes updating and transitions to state three, state machine 231 can transition to state one, unless state machine 231 has already transitioned to state four. If state machine 231 has already transitioned to state four, then state machine 231 can transition to state one once the second stimulation program has ceased executing.

In some embodiments, when one state machine is in the fourth state and the other state machine is not in the third state, completion of stimulation can cause the state machine in the fourth state to return to the third state. Receipt of additional execution requests can cause the state machine to return to the fourth state, retriggering stimulation. For example, state machine 231 can be in the fourth state and state machine 221 can be in the first state. Upon cessation of stimulation, state machine 231 can return to the third state. Should pulse generator 200 receive another execution request prior to cessation of stimulation, state machine 231 can return to the fourth state, retriggering stimulation.

In some embodiments, priorities can be associated with transitions between states. For example, the transitions involving updating (e.g., from state one to state two, or from state two to state three) can be lower priority that the transitions involving execution (e.g., from state three to state four, from state four to state four, or from state four to state one). In some embodiments, transitions involving updates can be implemented as application layer functions, while transitions involving execution can be implemented as high priority tasks.

In some embodiments, pulse generator 200 can be configured to include a parameter memory 240. Parameter memory 240 can enable pulse-to-pulse modification of the stimulation characteristics of a currently executing stimulation program. Parameter memory 240 can be configured to store neuromodulation parameters. When a neuromodulation pulse is generated, the characteristics of the neuromodulation pulses can depend on values stored in parameter memory 240. Parameter memory 240 can be accessible during provision of stimulation such that the stimulation parameter can be changed from pulse to pulse. For example, stimulation amplitude can be stored in parameter memory 240. When a pulse is output, the amplitude of the pulse can depend on the parameter stored in parameter memory 240. In response to data or instructions received from another device (e.g., controller 130 or programmer 140), amplitude parameters in parameter memory 240 can be modified or overwritten. In this manner, pulse to pulse changes in stimulation amplitude can be achieved. As may be appreciated, other stimulation parameters can be similarly updated pulse to pulse.

Consistent with disclosed embodiments, stimulation engine 260 can be configured to control storing and execution of stimulation programs. In some embodiments, stimulation engine 260 can be configured to assign stimulation programs received (e.g., from programmer 140 and/or controller 130) to program memory. In some embodiments, stimulation engine 260 can be configured to update the states of the state machines. In some embodiments, stimulation engine 260 can maintain a queue of simulation programs (or memories). Stimulation engine 260 can read from the memory associated with the stimulation program at the head of the queue, thereby jumping from one stimulation program to the another seamlessly, without ceasing stimulation. As described herein, the stimulation output can be provided to leads 120.

FIG. 3 depicts an exemplary process 300 for providing updated stimulation programs without ceasing stimulation, consistent with disclosed embodiments. As may be appreciated, stimulation provided according to the stimulation programs can be used for neuromodulation. For convenience of description, process 300 is described with reference to a pulse generator (e.g., IPG 110, pulse generator 200, or the like). The pulse generator can alternatively accessible memories. In some embodiments, the pulse generator can include two program memories (e.g., program memories 220 and 230), two state machines (e.g., state machines 221 and 231), and a stimulation engine (e.g., stimulation engine 260). However, this description is not intended to be limiting. In some embodiments, for example, process 300 can be performed using an external stimulator. Furthermore, the pulse generator can include additional memories, additional state machines, and/or additional stimulation engines.

Consistent with disclosed embodiments, process 300 can enable the pulse generator to receive stimulation programs (e.g., from an controller, such as controller 130, or a programmer, such as programmer 140) without ceasing stimulation. The received stimulation program can be stored in the currently accessible program memory. In response to an instruction to execute the newly stored stimulation program, the stimulation program can be queued up by the stimulation engine. Upon completion of stimulation according to the currently executing stimulation program, the stimulation engine can begin providing stimulation according to the newly stored stimulation program, without ceasing stimulation.

In step 310 of process 300, the pulse generator can provide stimulation to a patient, consistent with disclosed embodiments. The stimulation can be provided in accordance with a first stimulation program. The first stimulation program can be saved in a first program memory of the pulse generator.

In step 320 of process 300, the pulse generator can obtain a second stimulation program, consistent with disclosed embodiments. In some embodiments, obtaining the second stimulation program can include receiving an instruction to obtain the second stimulation program. The instruction can be received by the pulse generator from a device connected by a communication link to the pulse generator (e.g., controller 130, programmer 140, or the like). The instruction can indicate that the pulse generator should obtain a second stimulation program. In some embodiments, the instruction can further indicate that the pulse generator should provide stimulation according to the second stimulation program.

In some instances, the second stimulation program may have been created or modified using a programmer (e.g., programmer 140, or the like) or another device (e.g., controller, computer, smart phone, tablet, or the like). The second program may have been created or modified using a graphical user interface. In some embodiments, the second stimulation program can enable a different action, or a different series of actions, compared with the first stimulation program. In some embodiments, the second stimulation program can be set up with different parameters to do the same or similar actions as the first stimulation program.

In some embodiments, the instruction can be provided by the device in response to a user or patient input (e.g., an interaction with a graphical user interface to begin a stimulation program) or in accordance with execution conditions or relationships. For example, an execution condition can specify provision of the second stimulation program in response to a certain status of the patient (e.g., provision of a stimulation program configured to reduce blood pressure in response to detection of high patient blood pressure). As an additional example, an execution relationship can specify that the first stimulation program is one of a sequence of such programs and the second stimulation program is the next stimulation program in that sequence. The sequence of stimulation programs (which may include loops, conditionals, or other flow control instructions) can enable the patient to perform complicated actions (e.g., standing on a chair) or a series of repetitive actions (e.g., walking by enabling alternating leg movement).

In some embodiments, in response to the instruction, the pulse generator can retrieve the second stimulation program from the device (or another source). For example, the pulse generator can provide a response to the device requesting transmission of the second stimulation program. In various embodiments, the second stimulation program can be provided together with the command, or following the command. In such embodiments, the pulse generator may not provide a response to the command. In some embodiments, the second stimulation program can be or include the command. For example, provision of the second stimulation program can constitute a command to execute the second stimulation program.

Consistent with disclosed embodiments, the stimulation engine can store the obtained second stimulation program in the currently accessible second program memory. The pulse generator can continue to provide stimulation according to the first stimulation program while the second program memory is being updated.

In step 330 of process 300, the pulse generator can store the second neuromodulation program in the second program memory, consistent with disclosed embodiments. As described with regards to FIG. 2, the pulse generator can update the state machine for the second program memory, transitioning the state machine from the first state ("ready to update") to the second state ("updating").

In step 340 of process 300, the pulse generator can determine that the second program memory has been updated with the second stimulation program, consistent with disclosed embodiments. As may be appreciated, the update to the second program memory may not be completed until the second stimulation program has been fully received by the pulse generator. In some instances, depending on the data rate of the communication link between the device providing the stimulation program and the pulse generator, the second stimulation program may be received within a relatively short period of time. In other instances, additional time may be required for the second stimulation program to be received. Any suitable method can be used to determine that the update to the second program memory has been completed. In response to the completion of the update to the second program memory, the pulse generator can update the state machine for the second program memory, transitioning the second state machine from the second state ("updating") to the third state ("ready to execute").

In step 350 of process 300, the pulse generator can determine that stimulation according to the first stimulation program has completed, consistent with disclosed embodiments. In some embodiments, a number of repeats (e.g., a repeat value) can be specified for the first stimulation program. For example, an instruction specifying the number of repeats may have been received together with the first stimulation program. In some embodiments, repeats can be implemented using a queue that schedules stimulation. The queue can include multiple sequential references to the first stimulation program. As repeats are completed, they can be removed from the queue and stimulation providing according to the next referenced stimulation program. In some embodiments, the pulse generator can use counters to track the number of repeats remaining. As repeats are completed, the associated counter can be decremented. In such embodiments, stimulation according to the first stimulation program can be completed when no repeats remain, and the stimulation specified by the final repeat of the first stimulation program is completed. When no repeat is scheduled, stimulation can be complete when the stimulation specified by the first stimulation program is completed. For example, the first stimulation program can specify current-controlled 20 Hz stimulation for 30 seconds in alternating 1 second on, 1 second off bursts on two stimulation channels. The pulse generator can be configured to provide three repeats of this stimulation program. Stimulation according to the first stimulation program can therefore be complete when such stimulation has been provided for 90 seconds. Alternatively, when no repeats are specified, stimulation according to the first stimulation program can be complete when such stimulation has been provided for 30 seconds. Once the stimulation according to the first stimulation program has completed, the pulse generator can transition the first state machine from the fourth state ("executing") to the first state ("ready to update").

In some embodiments, the programmer or controller can be configured to track the number of repeats of the first stimulation program. For example, the controller or programmer can be configured with a counter for tracking a number of repeats of the first stimulation program. In some embodiments, the counter can be initialized to a repeat value. After each repeat, the counter can be decremented. In such embodiments, when a value of the counter is not zero, the programmer or controller can provide an execution request to the pulse generator. In response to the execution request, the pulse generator can provide stimulation according to the first stimulation program. Alternatively, the counter can be initialized to zero. After each repeat, the counter can be incremented. In such embodiments, when the value of the counter is less than the repeat value, the programmer or controller can provide an execution request to the pulse generator. In this manner, the programmer or controller can ensure that the stimulation is provided for the specified number of repeats.

In step 360 of process 300, the pulse generator can provide stimulation according to the second stimulation program, consistent with disclosed embodiments. In some embodiments, the pulse generator can access the second program memory to read the second stimulation program and provide an output as specified by the second memory. Upon the start of stimulation, the pulse generator can transition the second state machine from the third state ("ready-to-execute") to the fourth state ("executing").

In some embodiments, the pulse generator can maintain a queue for scheduling stimulation. The queue can include references to program memories. The pulse generator can access the referenced memory to obtain a stimulation program. The pulse generator can the provide stimulation according to the stimulation program. In some embodiments, the pulse generator can access stimulation programs in the order in which they are received by the pulse generator.

Figure 4:
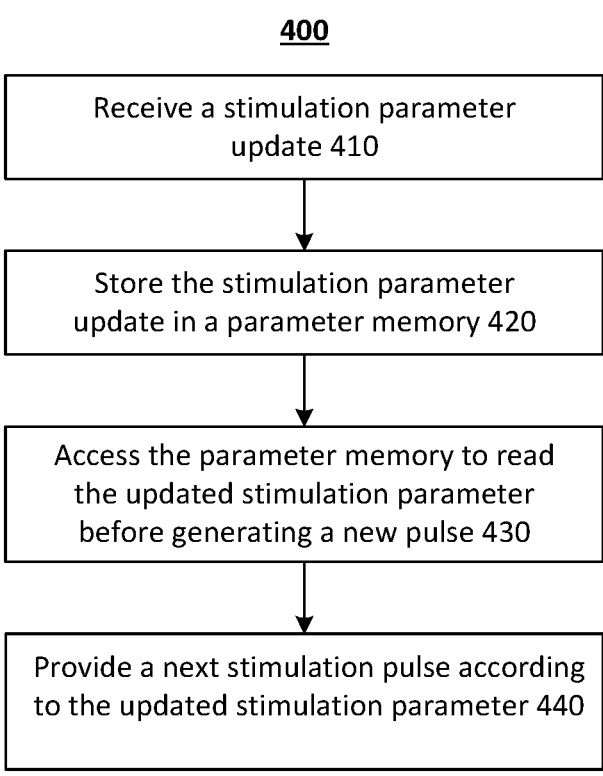
FIG. 4 depicts an exemplary process for updating stimulation parameters while a stimulation program is executing, according to some embodiments of the present disclosure.

FIG. 4 depicts an exemplary process 400 for updating stimulation parameters while a stimulation program is executing, consistent with disclosed embodiments. Process 400 can enable pulse-to-pulse changes in stimulation parameters without stopping stimulation. For convenience of description, the process 400 is described with reference to a pulse generator (e.g., IPG 110, pulse generator 200, or the like) that implements a parameter memory (e.g., parameter memory 240, or the like) and a stimulation engine (e.g., stimulation engine 260, or the like). As may be appreciated, this description is not intended to be limiting. Process 400 can be performed using other architectures, or other stimulation devices. The stimulation provided can be used for neuromodulation, consistent with disclosed embodiments.

In step 410 of process 400, the pulse generator can receive an instruction to update at least one stimulation parameter. The instruction can be received by the pulse generator from a device connected by a communication link to the pulse generator (e.g., controller 130, programmer 140, or the like). In some embodiments, the instruction can be provided by the device in response to a user or patient input (e.g., an interaction with a graphical user interface to increase a stimulation amplitude or change a stimulation frequency). In some embodiments, the instruction can be provided by the device after an initial configuration of the currently executing stimulation program.

In some embodiments, the instruction can specify a value for the stimulation parameter (e.g., a stimulation amplitude value). In some embodiments, the instruction can specify an intermediate value then can be used to generate one or more values of one or more stimulation parameters. For example, the instruction can specify an incremental change in the value of a stimulation parameter (e.g., increase pulse width 0.010 ms, or the like). As an additional example, the instruction can specify a value or incremental change for a stimulation parameter that is related (e.g., by rules or conditions) to multiple other stimulation parameters, such that changing the one stimulation parameter changes the other stimulation parameters. For example, increasing a current amplitude may increase a charge per phase. The pulse generator may be programmed with limits on charge per phase, such that an instruction increasing the current amplitude results in a concomitant decrease in the pulse duration, such that the charge per phase value remains within the limit. As an additional example, when current controlled stimulation is provided to multiple electrodes, an overall stimulus amplitude can be converted to a per-electrode stimulus amplitude.

In step 420 of process 400, the pulse generator can store the stimulation parameter in the parameter memory, consistent with disclosed embodiments. In some embodiments, storing the stimulation parameter can include storing a function of the value of the stimulation parameter. For example, the instruction can specify a first stimulation amplitude. The currently executing stimulation program can specify a second stimulation amplitude. In this example, storing the stimulation parameter can include storing a ratio of these stimulus amplitude values in the parameter memory, such that the product of the stored value and the second stimulation amplitude equals the first stimulation amplitude.

In step 430 of process 400, the pulse generator can access the parameter memory during the provision of stimulation according to a stimulation program. In some embodiments, the value of the stimulation parameter can be accessed prior to generating the next stimulation pulse. Consistent with disclosed embodiments, the pulse generator can determine the appropriate values for the next stimulation pulse based at least in part on the stimulation pulse value stored in the parameter memory. In some embodiments, the value stored in the parameter memory can replace the corresponding value stored in the program memory. For example, the stimulation program can specify a first pulse width and the value of the stimulation parameter can specify a second pulse width. The next stimulation pulse can then be generated using the second pulse width. In some embodiments, the value stored in the parameter memory can be combined with the corresponding value stored in the program memory to generate the value for the next stimulation pulse. For example, when the stored stimulation parameter is a ratio of a stimulation amplitude specified in the received instructions and the stimulation amplitude specified in the stimulation program, the next stimulation pulse can then be generated using the product of the stored stimulation parameter and the stimulation amplitude specified in the stimulation program.

In step 440 of process 400, the pulse generator can provide a next stimulation pulse based on the updated neuromodulation parameter. In this manner, the programmer or controller can provide an instruction to change the stimulation parameter and a corresponding change in the stimulation parameter can occur within a short period of time. In some embodiments, this period of time can be approximately equal to (or less than) the sum of the time required to communicate the instruction and the interpulse interval of the currently executing stimulation program. In some embodiments, the period of time required to change the stimulation can be less than 100 ms, less than 50 ms, less than 30 ms, or less.

Consistent with disclosed embodiments, a reset of all the updated parameters can be available via the user interface. In some embodiments, the reset command can reset the latest changes. In some embodiments, the reset command can reset several changes. In some embodiments, the reset command can reset the stimulation parameters back to the parameters specified in the currently executing stimulation program.

Figure 5:
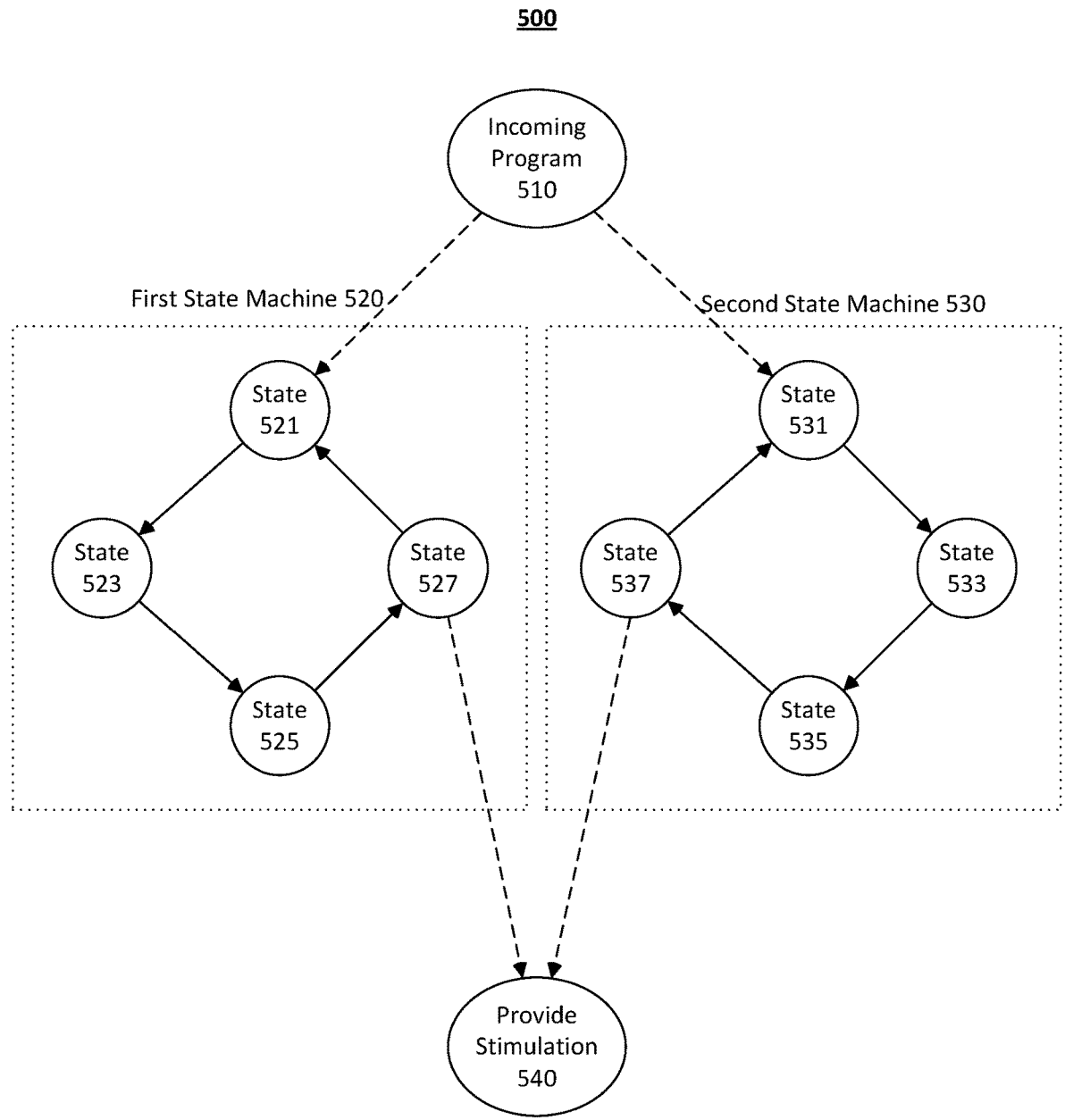
FIG. 5 depicts an exemplary logical diagram of state machines, according to some embodiments of the present disclosure.

FIG. 5 depicts an exemplary logical diagram 500 of state machines, consistent with disclosed embodiments. Diagram 500 shows the relationship between the state machines and an incoming stimulation program, and the relationship between the state machines and the stimulation provided. A pulse generator (e.g., IPG 110, pulse generator 200, or the like) can implement state machines consistent with diagram 500 to enable the pulse generator to receive and store a second stimulation program while providing output according to a first stimulation program. As may be appreciated, the stimulation provided can be used for neuromodulation.

Diagram 500 depicts an exemplary implementation including two state machines, first state machine 520 and second state machine 530. In some embodiments, each of these state machines can be associated with a program memory (e.g., program memory 220, 230). In some embodiments, each state machine can be configured with four states. As may be appreciated, the disclosed embodiments are not limited to state machines including four states. In some embodiments additional states may be included, or fewer states.

In some embodiments, when a state machine (e.g., state machine 520 or state machine 530) is in the first state (e.g., state 521 or state 531), the corresponding program memory can be accessible for writing. A pulse generator can obtain and load the stimulation program into the program memory in response to an update request. As described herein, the update request can specify or include the stimulation program. In response to the update request, the pulse generator can cause the state machine to transition to the second state (e.g., state 523, or state 533).

In some embodiments, the pulse generator can write the stimulation program to the corresponding program memory when the state machine is in the second state. Once the pulse generator has completed writing the stimulation program to the corresponding program memory, the pulse generator can cause the state machine to transition to the third state (e.g., state 525, or state 535).

In some embodiments, when the state machine is in the third state, the corresponding program memory can be accessible for reading. In response to an execution request, the pulse generator can cause the state machine to transition to the fourth state. The state machine can be in the fourth state (e.g., state 527, or state 537) when the stimulation program is read from the corresponding program memory. The pulse generator can be configured to provide stimulation 540 according to the stimulation program read from the corresponding program memory.

Consistent with disclosed embodiments, an incoming program 510 can be obtained from a device (e.g., controller 130 or programmer 140). In some embodiments, the incoming program can be stored in a program memory corresponding to a state machine in the first state (e.g., state 521 or state 531). In some embodiments, both state machines may be in the first state. In such embodiments, the pulse generator can store the incoming program in either program memory and update the corresponding state machine to the second state. In various embodiments, as described herein, state machines can possess additional transitions. These additional transitions can ensure that only one state machine can be in state one. For example, when a first state machine is in state one and the second state machine is in state four, the second state machine can transition back to state three, rather than transitioning to state one. In some embodiments, the additional transitions can ensure that only one state machine can be in state three. For example, when a first state machine is in state three and the second state machine is in state four, the second state machine can transition back to state one, rather than transitioning to state three. As an additional example, when a first state machine is in state three and the second state machine is in state two, the first state machine can transition to state one in response to the second state machine transitioning to state three.

In some embodiments, the pulse generator can maintain an incoming program queue. The incoming program queue can be configured to temporarily store stimulation programs until a program memory becomes available (e.g., the associated state machine transitions to state one). The contents of the incoming program queue can then be written to the program memory.

The architecture described herein can support rapid changes in stimulation parameters without requiring cessation of stimulation. Consistent with the disclosed embodiment, a latency between receiving an update request and providing stimulation in response to the request can be less than 100 milliseconds. In some embodiments, such a latent can be less than 50 milliseconds.

In some embodiments, the pulse generator can be configured to execute stimulation programs without requiring an express execution request. In such embodiments, a state machine in state three can automatically transition to state four, provided another state machine is not already in state four. For example, when first state machine 520 is in state 527, the pulse generator can provide stimulation according to a first stimulation program stored in a program memory corresponding to first state machine 520. Second state machine 530 can complete responding to an update request and transition to state 535. Upon completion of stimulation according to the first stimulation program, the first state machine 520 can transition to state 521, while second state machine 530 can transition to state 537. The pulse generator can then provide stimulation according to a second stimulation program stored in a program memory corresponding to second state machine 530.

In some embodiments, the pulse generator can be configured to repeat execution of stimulation programs. In such embodiments, a state machine in state four can automatically return to state four, provided another state machine is not in state three. In such embodiments, the pulse generator can be configured to repeat execution of the stimulation program until an execution stop request is received.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware, but systems and methods consistent with the present disclosure can be implemented with hardware and software. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

As used herein, unless specifically stated otherwise, the term "or" encompasses all possible combinations, except where infeasible. For example, if it is stated that a component may include A or B, then, unless specifically stated otherwise or infeasible, the component may include A, or B, or A and B. As a second example, if it is stated that a component may include A, B, or C, then, unless specifically stated otherwise or infeasible, the component may include A, or B, or C, or A and B, or A and C, or B and C, or A and B and C.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A neuromodulation system, comprising:
an implantable pulse generator configured to provide neuromodulation to a patient based on a sequence of neuromodulation programs, the implantable pulse generator comprising alternately accessible memories; and
wherein
a second memory of the memories is configured for receiving and storing a second neuromodulation program of the sequence of neuromodulation programs while the implantable pulse generator provides neuromodulation according to a first neuromodulation program of the sequence of neuromodulation programs, the first neuromodulation program stored in a first memory of the memories.

2. The neuromodulation system of claim 1, wherein the sequence of neuromodulation programs is configured to enable one or more functions selected from a group consisting of postural and/or locomotor activity, upper and/or lower limb activity, voluntary voiding of the bladder and/or bowel, sexual function, autonomic control of cardiovascular function, respiratory and/or coughing function, body temperature control, and normalized metabolic processes.

3. The neuromodulation system of claim 1, wherein:
the implantable pulse generator is further configured to receive the first neuromodulation program and the second neuromodulation program from a programmer that stores the sequence of neuromodulation programs.

4. The neuromodulation system of claim 3, further comprising:
a controller configured to maintain a communication link with the implantable pulse generator.

5. The neuromodulation system of claim 4, wherein:
the implantable pulse generator is further configured to cease providing the neuromodulation when the communication link fails for a period of time.

6. The neuromodulation system of claim 5, wherein the period of time is in a range of 0.1 second to 5 minutes.

7. The neuromodulation system of claim 5, wherein the period of time is in a range of 0.1 second to 60 seconds.

8. The neuromodulation system of claim 1, wherein:
the implantable pulse generator is further configured to:
receive, from the programmer, an update instruction specifying an update of a stimulation parameter;
store, in a parameter memory, the update of the stimulation parameter;
access, in the parameter memory during provision of the neuromodulation according to a first neuromodulation program, the update of the stimulation parameter; and
provide a next pulse of the neuromodulation based on the stimulation parameter.

9. The neuromodulation system of claim 8, wherein the stimulation parameter comprises at least one of intensity, amplitude, pulse width, pulse ratio, electrode configuration, frequency, carrier frequency, or burst frequency.

10. The neuromodulation system of claim 1, wherein the second memory of the memories is configured for storing the second neuromodulation program according to a second state machine associated with the second memory, wherein:

when the second state machine is in a first state, the second memory is accessible for writing the second neuromodulation program;

the second state machine is in a second state when the second neuromodulation program is being written to the second memory;

when the second state machine is in a third state, the second memory is accessible for reading the second neuromodulation program; and the second state machine is in a fourth state when the second neuromodulation program is being read from the second memory.

11. The neuromodulation system of claim 10, wherein:

the second state machine transitions from the first state to the second state in response to an update request;

the second state machine transitions from the second state to the third state upon completion of the update request; and the second state machine transitions from the third state to the fourth state in response to an execution request upon completion of the neuromodulation provided according to the first neuromodulation program.

12. The neuromodulation system of claim 11, wherein a latency between receiving an update request and providing stimulation according to the request is less than 100 milli-second.

13. The neuromodulation system of claim 11, wherein a latency between receiving an update request and providing stimulation according to the request is less than 50 milli-seconds.

14. The neuromodulation system of claim 10, wherein:

completion of the neuromodulation according to the first neuromodulation program depends upon a repeat value associated with the first neuromodulation program.

15. A method for providing neuromodulation according to a sequence of neuromodulation programs, comprising:

receiving, by the implantable pulse generator and during provision of neuromodulation according to a first neu-romodulation program in the sequence of neuromodu-lation programs, the first neuromodulation program read from a first memory of the implantable pulse generator, a second neuromodulation program in the sequence of neuromodulation programs;

storing, in a second memory of the implantable pulse generator, the second neuromodulation program; and providing, by the implantable pulse generator and upon completion of the provision of the neuromodulation according to the first neuromodulation program, neu-romodulation according to the second neuromodulation program stored in the second memory.

16. The method of claim 15, wherein the first neuromodu-lation program and the second neuromodulation program are received from a programmer that stores the sequence of neuromodulation programs.

17. The method of claim 15, wherein the method further comprises:

receiving, by the programmer from a user, an instruction corresponding to the sequence of neuromodulation programs;

providing, by the programmer in response to the receipt of the instruction, the first neuromodulation program, and wherein the instruction enables one or more functions selected from a group consisting of postural and/or locomotor activity, upper and/or lower limb activity, voluntary voiding of the bladder and/or bowel, sexual function, autonomic control of cardiovascular function, respiratory and/or coughing function, body temperature control, and normalized metabolic processes.

18. The method of claim 15, wherein the method further comprises:

a controller configured to maintain a communication link with the implantable pulse generator.

19. The method of claim 15, the method further com-prises:

ceasing provision of the neuromodulation, by the implant-able pulse generator, when the communication link fails for a period of time.

20. The method of claim 15, the method further com-prises:

receiving, by the implantable pulse generator and during the provision of the neuromodulation according to the first neuromodulation program, an update instruction specifying an update of a stimulation parameter;

storing, in a parameter memory, the update of the stimu-lation parameter;

accessing, in the parameter memory during provision of the neuromodulation according to a first neuromodu-lation program, the update of the stimulation param-eter; and providing, by the implantable pulse generator, a next pulse of the neuromodulation based on the stimulation parameter.

21. The method of claim 20, wherein the stimulation parameter comprises at least one of intensity, amplitude, pulse width, pulse ratio, electrode configuration, frequency, carrier frequency, or burst frequency.

22. The method of claim 15, wherein:

storing the second neuromodulation program comprises storing the second neuromodulation program according to a second state machine associated with the second memory, the second state machine configured to:

enable writing to the second memory when the second state machine is in a first state; and transition from the first state to a second state in response to an update request to write the second neuromodulation program to the second memory; and providing the neuromodulation according to the second neuromodulation program comprises accessing the sec-ond memory according to the second state machine, the second state machine configured to:

enable access to the second memory when the second state machine is in a third state; and transition from the third state to a fourth state in response to an execution request to provide neuro-modulation according to the second neuromodula-tion program.

23. The method of claim 21, wherein the execution request is provided based on a repeat value associated with the first neuromodulation program.

* * * * *